US011497692B2

(12) United States Patent
Akridge et al.

(10) Patent No.: US 11,497,692 B2
(45) Date of Patent: Nov. 15, 2022

(54) SYSTEMS AND METHODS FOR BLENDING SOLID-SHELL COSMETIC INGREDIENT CAPSULES AND BLENDABLE COSMETIC INGREDIENT CAPSULES

(71) Applicant: REA Innovations, Inc., Seattle, WA (US)

(72) Inventors: Robb Akridge, Seattle, WA (US); Gregory Calvin Peterson, Seattle, WA (US)

(73) Assignee: REA Innovations, Inc., Bainbridge Island, WA (US)

( * ) Notice: Subject to any disclaimer, the term of this patent is extended or adjusted under 35 U.S.C. 154(b) by 130 days.

(21) Appl. No.: 17/069,214

(22) Filed: Oct. 13, 2020

(65) Prior Publication Data

US 2021/0106508 A1   Apr. 15, 2021

Related U.S. Application Data

(63) Continuation-in-part of application No. 16/840,171, filed on Apr. 3, 2020.
(Continued)

(51) Int. Cl.
*A61K 8/11*   (2006.01)
*A61K 8/92*   (2006.01)
(Continued)

(52) U.S. Cl.
CPC ............... *A61K 8/11* (2013.01); *A45D 34/00* (2013.01); *A61K 8/92* (2013.01); *B01F 27/91* (2022.01);
(Continued)

(58) Field of Classification Search
CPC ......... A61K 8/92; A61K 8/11; A61K 2800/00
See application file for complete search history.

(56) References Cited

U.S. PATENT DOCUMENTS 3,167,602 A   1/1965   Bentov et al.
5,271,934 A   12/1993   Goldberg et al.
(Continued)

FOREIGN PATENT DOCUMENTS

CN   106693785 A   5/2017
CN   107855026 A   3/2018
(Continued)

OTHER PUBLICATIONS

English-language machine translation of Japanese Patent Application Publication No. JP 2007503418 A, Feb. 22, 2007.
(Continued)

*Primary Examiner* — Blessing M Fubara
(74) *Attorney, Agent, or Firm* — Kolitch Romano Dascenzo Gates LLC

(57) ABSTRACT

Cosmetic blending devices for producing a cosmetic liquid from a solid-shell cosmetic ingredient capsule. The cosmetic blending devices include a lid, a base, a blending element configured to blend the capsule, and a drive mechanism configured to actuate the blending element. The cosmetic blending device may include a thermal element configured to change a temperature of the capsule. The thermal element may melt the capsule. The solid-shell cosmetic ingredient capsule comprises a shell defining an enclosed inner volume, and cosmetic material included in the enclosed inner volume. Methods of using the cosmetic blending devices comprise placing the solid-shell cosmetic ingredient capsule into the cosmetic blending device and blending the capsule to produce the cosmetic liquid. Methods of forming the solid-shell cosmetic ingredient capsule comprise forming a portion of the shell, adding the cosmetic material to the portion of the shell, and forming the remaining portion of the shell.

23 Claims, 15 Drawing Sheets

Related U.S. Application Data

(60) Provisional application No. 62/915,329, filed on Oct. 15, 2019.

(51) Int. Cl.
*B29B 13/02* (2006.01)
*B29D 22/00* (2006.01)
*A45D 34/00* (2006.01)
*B01F 27/91* (2022.01)
*B01F 35/90* (2022.01)
*B01F 101/21* (2022.01)

(52) U.S. Cl.
CPC .............. *B01F 35/90* (2022.01); *B29B 13/02* (2013.01); *B29D 22/003* (2013.01); *A45D 2200/051* (2013.01); *A61K 2800/87* (2013.01); *B01F 2035/99* (2022.01); *B01F 2101/21* (2022.01)

(56) References Cited

U.S. PATENT DOCUMENTS

| | | | |
|---|---|---|---|
| 5,672,359 | A | 9/1997 | Digenis et al. |
| 5,744,146 | A | 4/1998 | Peters et al. |
| 6,280,781 | B1 | 8/2001 | Lande |
| 6,391,288 | B1 | 5/2002 | Miyazawa et al. |
| 7,066,640 | B2 | 6/2006 | Sands |
| 7,421,941 | B2 | 9/2008 | Kim |
| 7,622,132 | B2 | 11/2009 | Lee et al. |
| 7,967,499 | B2 | 6/2011 | Tague et al. |
| 8,529,118 | B2 | 9/2013 | Davis et al. |
| 8,931,401 | B2 | 1/2015 | Cheung |
| 9,033,605 | B2 | 5/2015 | Gueret |
| 9,278,800 | B2 | 3/2016 | Seo et al. |
| 9,468,339 | B2 | 10/2016 | Conti et al. |
| 9,717,319 | B2 | 8/2017 | Ebeling |
| 10,076,175 | B2 | 9/2018 | Wee |
| 2002/0044991 | A1 | 4/2002 | Auweter et al. |
| 2002/0048553 | A1 | 4/2002 | Baumgartner |
| 2004/0219268 | A1* | 11/2004 | Hogoy ................. A23K 20/163 264/4.1 |
| 2005/0067726 | A1 | 3/2005 | Yan et al. |
| 2006/0147390 | A1 | 7/2006 | Schreiber et al. |
| 2006/0292193 | A1 | 12/2006 | Lee et al. |
| 2007/0172565 | A1 | 7/2007 | Kaiser et al. |
| 2008/0089913 | A1 | 4/2008 | Kallmayer et al. |
| 2009/0181254 | A1 | 7/2009 | White et al. |
| 2009/0317431 | A1 | 12/2009 | Schaefer et al. |
| 2010/0089414 | A1 | 4/2010 | Wyatt et al. |
| 2011/0052680 | A1 | 3/2011 | Hendrickson et al. |
| 2011/0097133 | A1 | 4/2011 | Duru et al. |
| 2011/0111020 | A1 | 5/2011 | Yan et al. |
| 2011/0180445 | A1 | 7/2011 | Hurwitz |
| 2011/0223224 | A1 | 9/2011 | Mathonnet et al. |
| 2014/0106032 | A1 | 4/2014 | Dardelle et al. |
| 2014/0227330 | A1 | 8/2014 | Kallmayer et al. |
| 2016/0095416 | A1 | 4/2016 | Kim |
| 2016/0270511 | A1 | 9/2016 | Wee |
| 2016/0367449 | A1 | 12/2016 | Son et al. |
| 2017/0042774 | A1 | 2/2017 | Shimizu et al. |
| 2017/0049139 | A1 | 2/2017 | Tsutsumi et al. |
| 2017/0304789 | A1 | 10/2017 | Tourel et al. |
| 2018/0303220 | A1 | 10/2018 | Wee Eng Jin |
| 2019/0070078 | A1* | 3/2019 | Akridge ................. A45D 34/00 |
| 2019/0314774 | A1 | 10/2019 | Gros et al. |

FOREIGN PATENT DOCUMENTS

| | | |
|---|---|---|
| DE | 19735539 B8 | 9/2010 |
| EP | 0389700 A1 | 10/1990 |
| EP | 0594820 B1 | 1/2000 |
| EP | 0757529 B1 | 6/2000 |
| EP | 2265159 B1 | 10/2011 |
| EP | 2315543 B1 | 11/2012 |
| EP | 2543293 A1 | 1/2013 |
| EP | 3076837 B1 | 2/2019 |
| JP | 2007503418 A | 2/2007 |
| JP | 2014015410 A | 1/2014 |
| JP | 2014037397 A | 2/2014 |
| JP | 5472785 B2 | 4/2014 |
| KR | 96-009639 B1 | 7/1996 |
| KR | 10-2013-0079244 A | 7/2013 |
| KR | 10-1309511 B1 | 9/2013 |
| KR | 10-2014-0011550 A | 1/2014 |
| KR | 10-2008935 B1 | 8/2019 |
| WO | WO 2008/143372 A1 | 11/2008 |
| WO | WO 2011/000418 A1 | 1/2011 |
| WO | WO 2014/080093 A1 | 5/2014 |
| WO | WO 2016/087470 A2 | 6/2016 |
| WO | WO 2017/118800 A1 | 7/2017 |
| WO | WO 2018/042137 A1 | 3/2018 |
| WO | WO 2018/046344 A1 | 3/2018 |
| WO | WO 2018/073541 A1 | 4/2018 |
| WO | WO 2018/135551 A1 | 7/2018 |

OTHER PUBLICATIONS

English-language machine translation of Japanese Patent Application Publication No. JP 2014015410 A, Jan. 30, 2014.

English-language machine translation of Japanese Patent Application Publication No. JP 2014037397 A, Feb. 27, 2014.

"PWE-398 Cold hands warm heart: does hand rubbing really make a difference?" C. Gunner; M. Lee; A. Bhakta; H. Casserly; K. Chapple, *Gut*, 2015; vol. 64, Suppl. 1, pp. A385.

Fleet Laxative Amazon.co.uk product page: "Fleet 185B Liquid Glycerin Suppositories, 4 ea.": www.amazon.co.uk/Fleet-185B-Liquid-Glycerin-Suppositories/dp/B0000530H5, available at least as early as Mar. 1, 2016.

Glycilax für Erwachsene, "Gebrauchinformation: Information füir den Anwender": image.wub-service.de/resources/static/des/210715/44/02/44023.pdf, available at least as early as Aug. 1, 2014.

English-language machine translation of Chinese Patent Application Publication No. CN 106693785 A, May 24, 2017.

English-language machine translation of Chinese Patent Application Publication No. CN 107855026 A, Mar. 30, 2018.

English-language machine translation of German Patent No. DE 19735539 B8, Sep. 16, 2010.

English-langugae machine translation of European Patent Application Publication No. EP 0594820 B1, Jan. 19, 2000.

English-langugae machine translation of European Patent Application Publication No. EP 0757529 B1, Jun. 28, 2000.

English-language machine translation of European Patent No. EP 2315543 B1, Nov. 14, 2012.

English-language machine translation of Japanese Patent No. JP 5472785 B2, Apr. 16, 2014.

English-language machine translation of Korean Patent No. KR 96-00963 9 B1, Jul. 23, 1996.

English-language machine translation of Korean Patent No. KR 10-1309511 B1, Sep. 11, 2013.

English-language machine translation of Korean Patent No. KR 10-2008935 B1, Aug. 8, 2019.

English-language machine translation of Korean Patent Application Publication No. KR 10-2013-0079244 A, Jul. 10, 2013.

English-language machine translation of Korean Patent Application Publication No. KR 10-2014-0011550 A, Jan. 29, 2014.

English-language machine translation of PCT Patent Application Publication No. WO 2014/080093 A1, May 30, 2014.

English-language machine translation of PCT Patent Application Publication No. WO 2017/118800 A1, Jul. 13, 2017.

English-language machine translation of PCT Patent Application Publication No. WO 2018/042137 A1, Mar. 8, 2018.

English-language machine translation of PCT Patent Application Publication No. WO 2018/046344 A1, Mar. 15, 2018.

English-language machine translation of PCT Patent Application Publication No. WO 2018/073541 A1, Apr. 26, 2018.

English-language machine translation of PCT Patent Application Publication No. WO 2018/135551 A1, Jul. 26, 2018.

(56) References Cited

OTHER PUBLICATIONS

ORB product page: www.spapliance.com/shop/theorb/whiteorb, available at least as early as Dec. 6, 2014.
EdensSecret1, "How to Decorate Bath Bombs," www.youtube.com/watch?v=E2rrgI2wbWs, published Jun. 15, 2016.
Dana Dey, "DIY Face Sheet Mask Machine for All Skin Types /All Natural—Kingdom Cares Mask Machine", www.youtube.com/watch?v=7emi4YaVJ6Y, published Aug. 12, 2017.
Admix, In-Tank and Inline Mixers, Powder Induction Systems and More: www.admix.com/equipment, available at least as early as Oct. 27, 2011.
My Make Up Brush Set DIY Facial Sheet Mask Maker product page: www.mymakeupbrushset.com/products/super-natural-facial-machine-maker, available at least as early as Jul. 5, 2018.
Tatcha Facial Cleansing Brush Set product page: www.tatcha.com/product/FACE-BRUSH-SET.html, available at least as early as Mar. 26, 2018.
Vitamix Professional Series 750 blender product page: www.vitamix.com/us/en_us/Shop/Professional-Series-750, available at least as early as Jan. 31, 2015.
BlendJet One product page: blendjet.com/products/blendjet-one, available at least as early as Jul. 31, 2018.

\* cited by examiner

SYSTEMS AND METHODS FOR BLENDING SOLID-SHELL COSMETIC INGREDIENT CAPSULES AND BLENDABLE COSMETIC INGREDIENT CAPSULES

RELATED APPLICATIONS

The present application claims priority under 35 U.S.C. § 120 to U.S. patent application Ser. No. 16/840,171, which was filed on Apr. 3, 2020. The present application also claims priority under 35 U.S.C. § 119 to U.S. Provisional Patent Application No. 62/915,329, which was filed on Oct. 15, 2019. The complete disclosures of these applications are hereby incorporated by reference.

FIELD OF THE DISCLOSURE

The present disclosure relates generally to devices and methods for producing cosmetic liquids from solid-shell cosmetic ingredient capsules, as well as to blendable cosmetic ingredient capsules that are configured to be heated and blended to produce the cosmetic liquids.

BACKGROUND OF THE DISCLOSURE

Cosmetics, such as creams, lotions, powders, mousses, gels, serums, balms, etc., may be applied to the skin, hair, nails, and/or other external body surfaces for various purposes, such as to beautify, enhance, soothe, moisturize, hydrate, and/or treat a specific issue or condition (e.g., acne). However, traditional cosmetics lose some of their efficacy because of the lengthy delay between the time of manufacturing and the time of use. In particular, many cosmetic products are mass produced in large quantities, packaged, stored at the manufacturer's facilities, shipped to retailers, stored on the retailers' shelves, sold to consumers, stored at the consumers' homes, and then dispensed, repeatedly, by the consumers over a prolonged period of time (e.g., months). This whole process, from manufacturing to use, can take many months or even years, and conventional cosmetics thus must contain sufficient preservatives to remain acceptable for consumer use during this time. When consumers have varying and/or multiple skin, hair, nail, etc. care or treatment needs, consumers thus must purchase and store multiple containers of cosmetics to accommodate these needs. These containers typically contain quantities of pre-made cosmetics to last for weeks or months when used daily, and thus much longer when only used periodically. Further, when applied to the skin, hair, nails, and/or other external body surfaces, the cosmetics may feel cold to the touch because they are often stored at room temperature in the consumer's home.

SUMMARY OF THE DISCLOSURE

Cosmetic blending devices configured to produce cosmetic liquids from solid-shell cosmetic ingredient capsules, solid-shell cosmetic ingredient capsules, methods of using the cosmetic blending devices to produce the cosmetic liquid, and methods of forming the solid-shell cosmetic ingredient capsules, are disclosed herein.

The cosmetic blending devices include a lid, a base, a blending element configured to blend the solid-shell cosmetic ingredient capsule, and a drive mechanism configured to actuate the blending element. The cosmetic blending device may include a thermal element configured to change a temperature within the enclosed blending chamber. The thermal element may melt the solid-shell cosmetic ingredient capsule. The lid and base may be adjusted between an open position and a closed position. In the open position, the lid and the base may permit a user to insert the solid-shell cosmetic ingredient capsule into the cosmetic blending device. In the closed position, the lid and the base may form and/or define an enclosed blending chamber that may be configured to retain the solid-shell cosmetic ingredient capsule and/or cosmetic liquid within the cosmetic blending device. The blending element may be included in the lid and may be configured to blend the solid-shell cosmetic ingredient capsule from above to produce the cosmetic liquid.

The solid-shell cosmetic ingredient capsule may include a shell defining an enclosed inner volume. The enclosed inner volume includes a cosmetic material. The cosmetic material may include a personal care ingredient and/or an active ingredient. When the active ingredient is included in the solid-shell cosmetic ingredient capsule, the shell additionally or alternatively may include the active ingredient. The shell may be configured to be solid at room temperature and may have a melting temperature of at least 32.2° C. When heated and blended, the cosmetic liquid may be formed from the entirety of the solid-shell cosmetic ingredient capsule.

Methods of using the cosmetic blending devices comprise placing the solid-shell cosmetic ingredient capsule into the cosmetic blending device, and blending the capsule to produce the cosmetic liquid. The methods additionally may include heating and/or melting the capsule.

Methods of forming the solid-shell cosmetic ingredient capsule comprise forming a portion of the shell, adding the cosmetic material to the portion of the shell, and forming the remaining portion of the shell such that the shell fully encloses the added cosmetic material. The shell may be formed in a mold, and the methods may include forming liquid shell material, dispensing this liquid shell material into the mold, and then solidifying at least a portion of the liquid shell material to form at least a portion of the shell.

DETAILED DESCRIPTION OF THE DISCLOSURE

Figure 14:
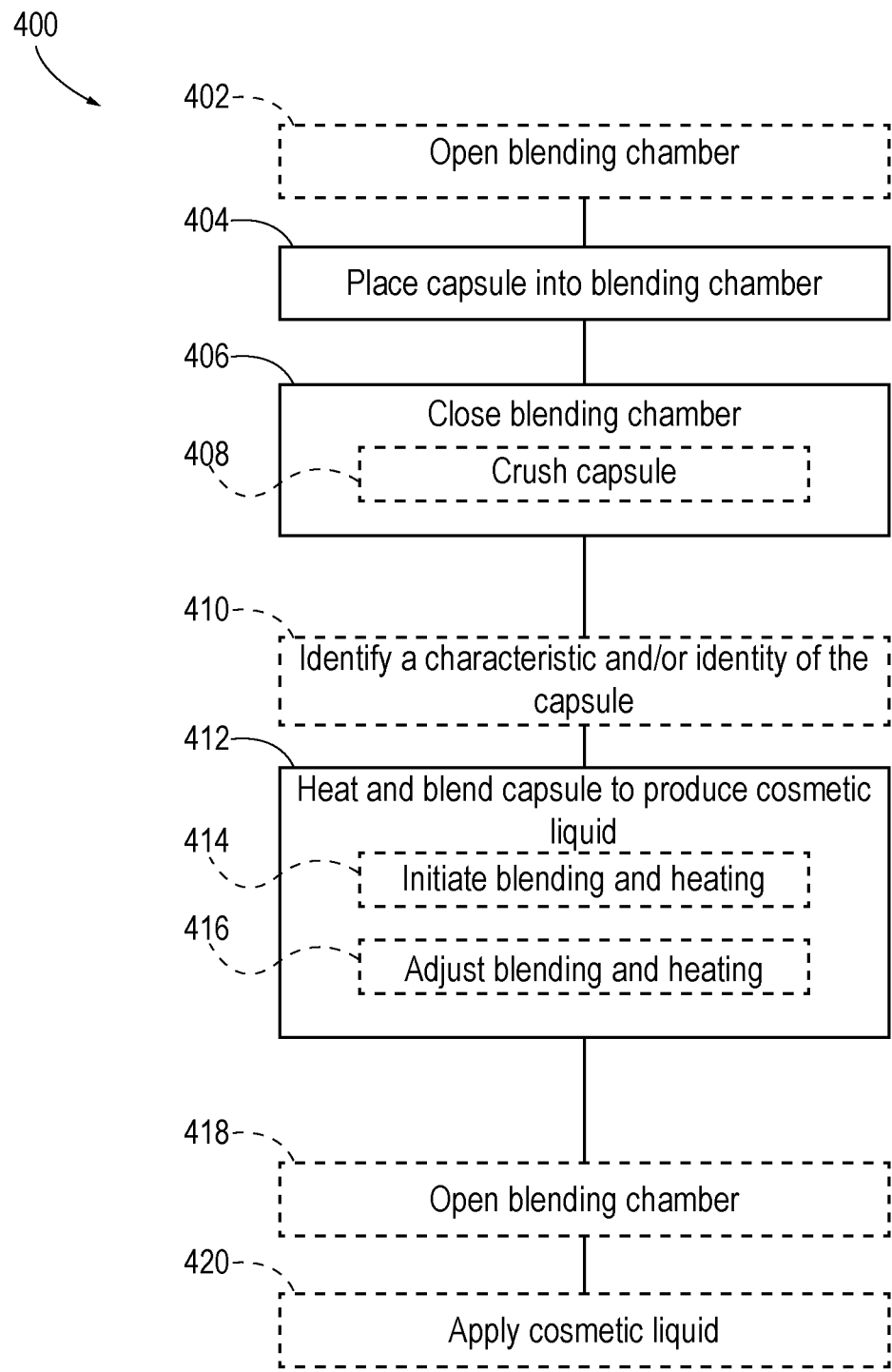
FIG. 14 is a flowchart depicting examples of methods of using a cosmetic blending device according to the present disclosure.
Figure 15:
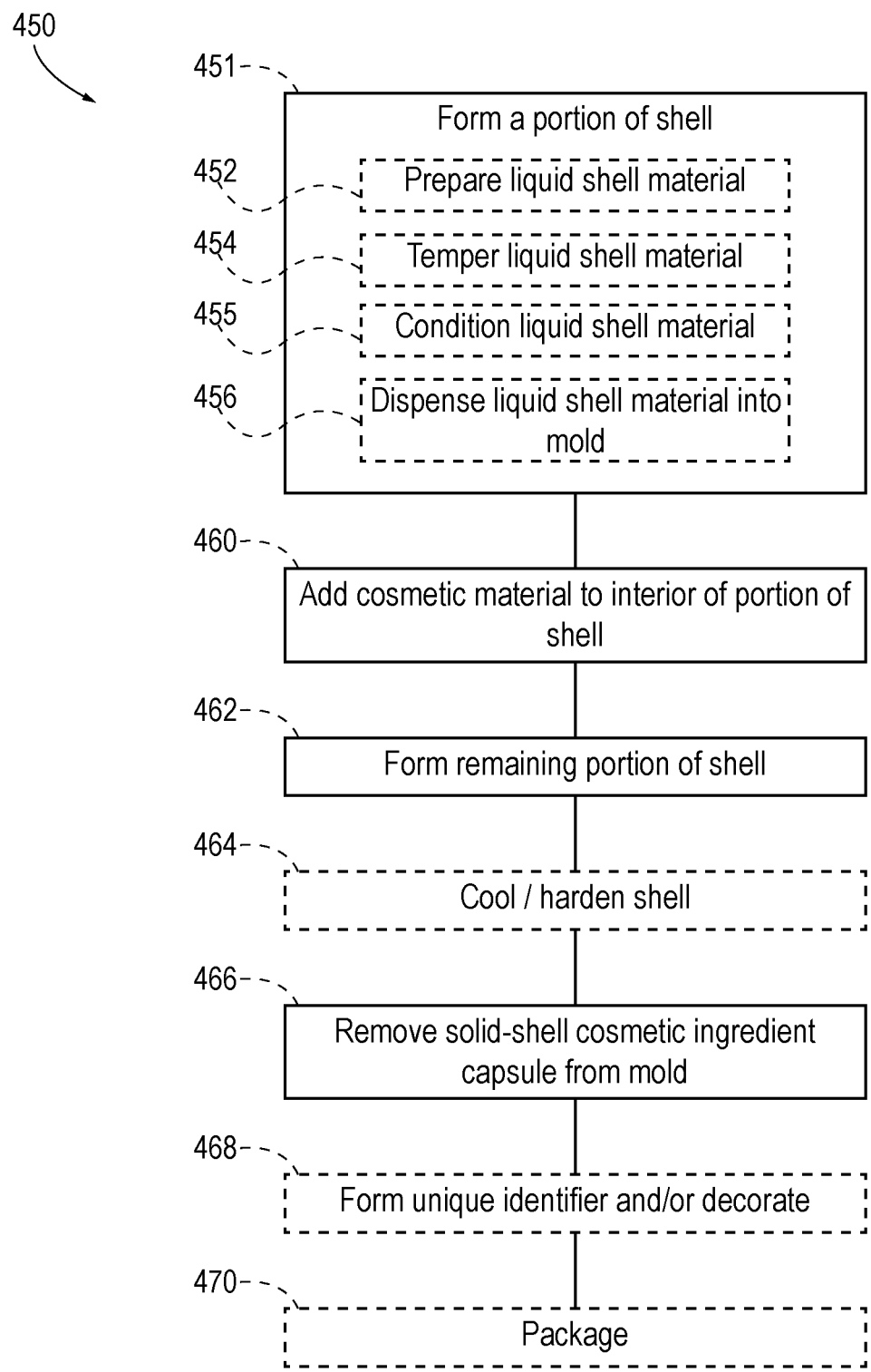
FIG. 15 is a flowchart depicting examples of methods of forming a solid-shell cosmetic ingredient capsule according to the present disclosure.

FIGS. 1-15 provide examples of cosmetic blending devices 10, of components and/or portions of cosmetic blending devices 10, of solid-shell cosmetic ingredient capsules 300, and/or of methods 400 and/or 450, according to the present disclosure. In particular, FIGS. 1-11 provide examples of cosmetic blending devices 10 and/or components or portions thereof, FIGS. 1, 3, and 12-13 provide examples of solid-shell cosmetic ingredient capsules 300, and FIGS. 14-15 provide examples of methods 400 and 450. Elements that serve a similar, or at least substantially similar, purpose are labeled with like numbers in each of FIGS. 1-15, and these elements may not be discussed in detail herein with reference to each of FIGS. 1-15. Similarly, all elements may not be labeled in each of FIGS. 1-15, but reference numerals associated therewith may be utilized herein for consistency. Elements, components, and/or features that are discussed herein with reference to one or more of FIGS. 1-15 may be included in and/or utilized with any of FIGS. 1-15 without departing from the scope of the present disclosure.

In general, elements that are likely to be included in a particular embodiment are illustrated in solid lines, while elements that are optional are illustrated in dashed lines. However, elements that are shown in solid lines may not be essential and, in some embodiments, may be omitted without departing from the scope of the present disclosure. Dotted lines also may be used to show additional and/or alternate positions of components. Electrical connections between components are shown in dash-dot lines.

Figure 1:
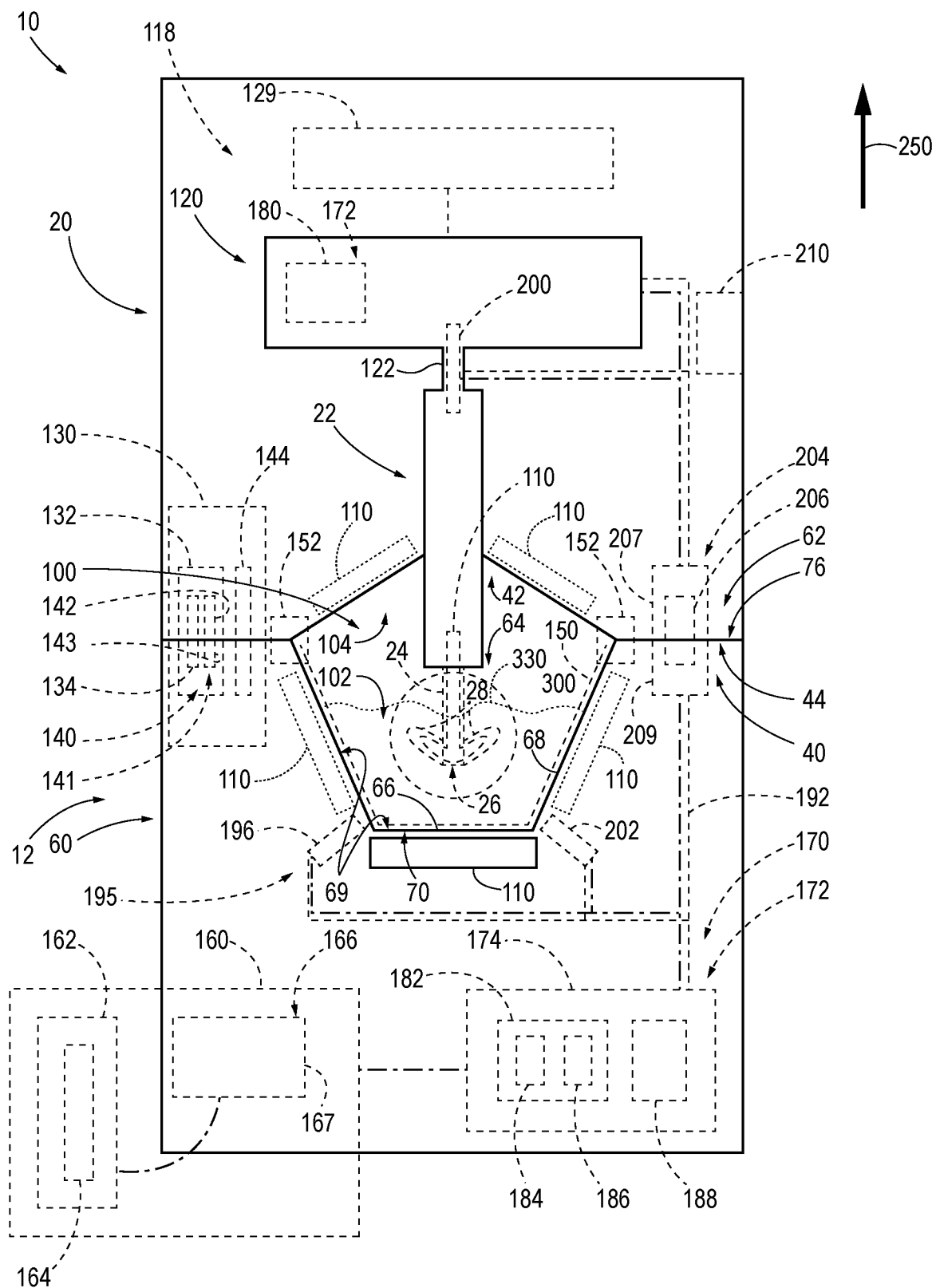
FIG. 1 is a schematic representation of cosmetic blending devices according to the present disclosure.
Figure 4:
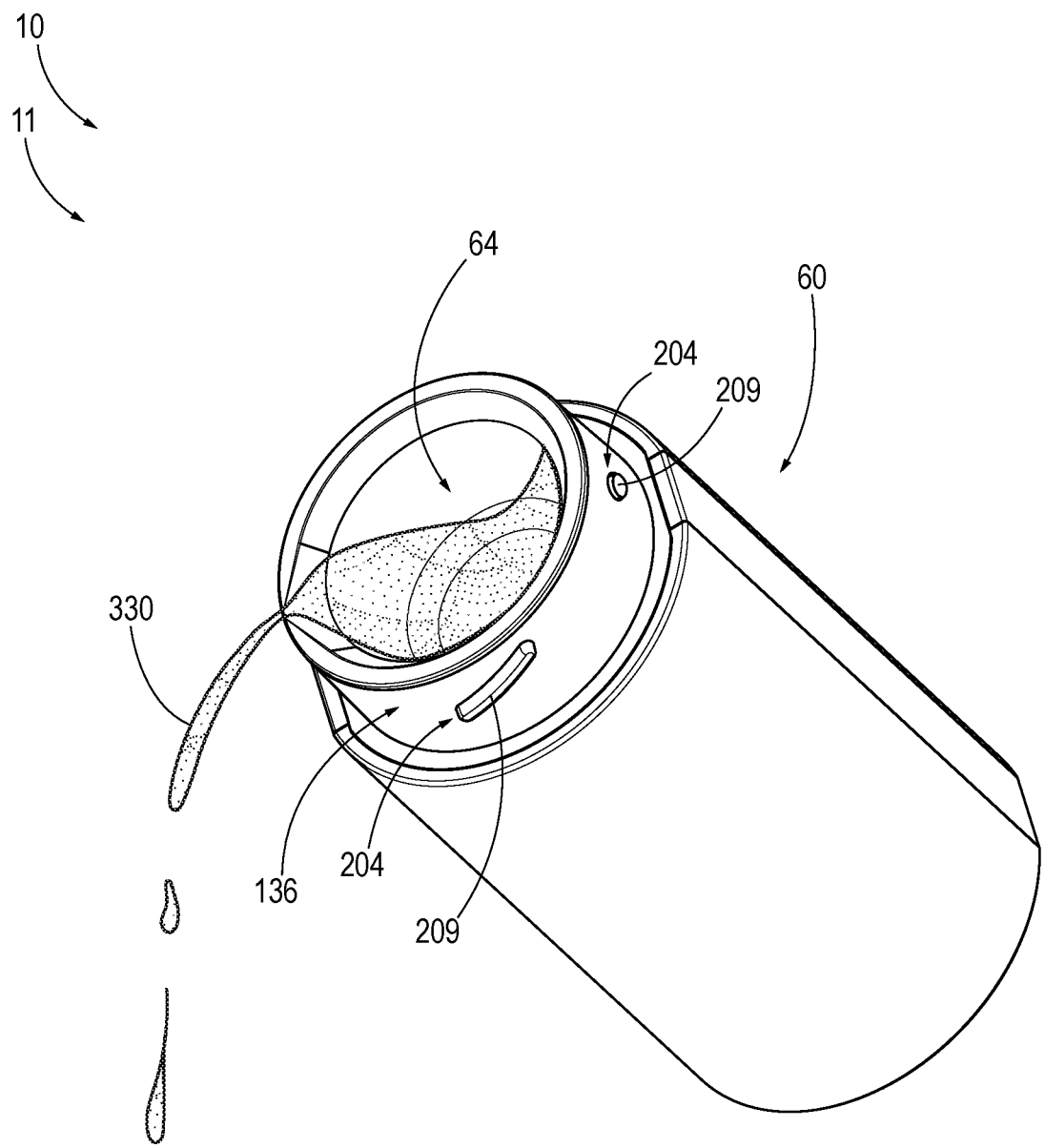
FIG. 4 is an external view of a base of the example cosmetic blending device of FIG. 2 schematically illustrated dispensing cosmetic liquid.

Cosmetic blending devices 10 are configured to heat and/or blend solid-shell cosmetic ingredient capsules 300 to produce a cosmetic liquid 330 (illustrated schematically in FIGS. 1 and 4). Cosmetic liquid 330 may be a final cosmetic product (e.g., cream, oil, mousse, serum, etc.) that is configured to be directly applied to a user's skin, hair, nails, and/or other body surfaces. Cosmetic blending devices 10 may be configured to receive one or more of the solid-shell cosmetic ingredient capsules (e.g., a user may place one or more of the solid-shell cosmetic ingredient capsules into one of the cosmetic blending devices), heat and/or blend the one or more solid-shell cosmetic ingredient capsules to produce the cosmetic liquid, and/or present the cosmetic liquid to a user for extraction and direct body application. As described in more detail herein, such heated and/or blended cosmetic liquids may be fresher, more soothing, more easily absorbed into the user's skin or other body part to which the cosmetic liquid is applied, and/or more efficacious than conventional cosmetic products that are mass produced in large quantities. Such conventional cosmetic products are packaged in large, often plastic, containers containing a sufficient quantity of the cosmetic product for dozens if not hundreds of uses or doses, stored at the manufacturer's facility, transported to retailers, shelved at the retailers' stores, sold to consumers, stored again at the consumer's home, and finally dispensed, repeatedly, by the consumer over a prolonged period of time (e.g., months).

FIG. 1 schematically illustrates examples of a cosmetic blending device 10 with examples of a solid-shell cosmetic ingredient capsule 300 positioned therein, according to the present disclosure. As depicted, cosmetic blending device 10 includes a housing 12 that defines the exterior of the device. Cosmetic blending device 10 further includes a lid 20 and a base 60 that are configured to be selectively adjusted between an open position and a closed position, with housing 12 thus defining at least eternal surfaces of the lid and the base. In the closed position, lid 20 and base 60 define an enclosed blending chamber 100. In the open position, enclosed blending chamber 100 may be open (e.g., accessible to a user), and/or portions of lid 20 and base 60 that are inaccessible to a user in the closed position may be accessible to the user, thereby permitting a user to insert and/or remove cosmetic materials (e.g., solid-shell cosmetic ingredient capsule 300, cosmetic liquid 330, etc.) from blending chamber 100 and/or a portion of lid 20 and/or base 60. The open and closed positions of lid 20 and base 60 additionally or alternatively may be referred to as the open and closed positions of cosmetic blending device 10 and/or the open and closed positions of blending chamber 100.

Cosmetic blending device 10 also includes a blending element 22 that is configured to blend solid-shell cosmetic ingredient capsule 300 to produce cosmetic liquid 330 therefrom. Although FIG. 1 illustrates lid 20 as including blending element 22, it is within the scope of the present disclosure that base 60 additionally or alternatively may include blending element 22. Thus, blending element 22 may be included in the lid and/or the base. Cosmetic blending device 10 also includes a thermal element 110 that is configured to change a temperature within enclosed blending chamber 100 and one or more actuators 118. As an example, the one or more actuators 118 may include a drive mechanism 120 that may be configured to oscillate, reciprocate, rotate, pivot, translate, and/or otherwise move blending element 22. As another example, the one or more actuators 118 may include a linear actuator 129 that may be configured to translate blending element 22 up and down within enclosed blending chamber 100.

During operation of cosmetic blending device 10, a user may open blending chamber 100, place solid-shell cosmetic ingredient capsule 300 into blending chamber 100, and close blending chamber 100. In particular, a user may adjust lid 20 and base 60 to the open position to open blending chamber 100 and/or otherwise provide access to the blending chamber from external the cosmetic blending device, and place solid-shell cosmetic ingredient capsule 300 into and/or onto a top 62 of base 60 that may define a lower portion 102 of blending chamber 100. The user then may adjust lid 20 and base 60 to the closed position to enclose blending chamber 100. Cosmetic blending device 10 then may be activated to heat and blend solid-shell cosmetic ingredient capsule 300 to produce cosmetic liquid 330 therefrom. In particular, thermal element 110 may be configured to heat solid-shell cosmetic ingredient capsule 300 to at least the melting point of solid-shell cosmetic ingredient capsule 300. Further, blending element 22 may be configured to rotate, oscillate, reciprocate, pivot, translate, and/or otherwise move within enclosed blending chamber 100 to blend solid-shell cosmetic ingredient capsule 300 to form cosmetic liquid 330.

Cosmetic blending device 10 may be configured to form cosmetic liquid 330 solely from solid-shell cosmetic ingredient capsule 300. Thus, cosmetic liquid 330 may be formed from only one solid-shell cosmetic ingredient capsule 300, or optionally two or more solid-shell cosmetic ingredient capsules 300. Said another way, solid-shell cosmetic ingredient capsule(s) 300 may form the entirety of cosmetic liquid 330. No other components, ingredients, or other elements (e.g., other cosmetics, liquids, powders, gels, emulsifiers, etc.) may need to be added to form cosmetic liquid 330. As examples, cosmetic liquid 330 may be formed solely from a single solid-shell cosmetic ingredient capsule 300, at least two solid-shell cosmetic ingredient capsules 300, at least three solid-shell cosmetic ingredient capsule 300, and/or at least four solid-shell cosmetic ingredient capsules 300.

Expressed in slightly different terms, the entirety of solid-shell cosmetic ingredient capsule 300 may form (i.e., may be used or consumed to form) cosmetic liquid 330. Thus, cosmetic blending device 10 may be configured to blend all of solid-shell cosmetic ingredient capsule 300 (i.e., the entire capsule and all of its contents) to form cosmetic liquid 330. In this way, blending element 22 may be configured to blend the entirety of solid-shell cosmetic ingredient capsule(s) 300. By blending the entire capsule, waste products (e.g., packaging, liners, wrapping) may be reduced and/or eliminated, thereby reducing costs and environmental impact.

When cosmetic blending device 10 has completed heating and blending the solid-shell cosmetic ingredient capsule, a user may open blending chamber 100 to access cosmetic liquid 330, which as discussed in more detail herein, then may be applied directly to the user's skin, hair, nails, and/or other body surfaces.

As used herein, cosmetic blending device 10 additionally or alternatively may be referred to as blending device 10, mixing device 10, cosmetic mixing device 10, heat and blending device 10, personal use cosmetic preparing device 10, cosmetic activator 10, and/or household cosmetic preparing device 10. As used herein, solid-shell cosmetic ingredient capsule 300 additionally or alternatively may be referred to as packageless cosmetic ingredient capsule 300, single-use cosmetic ingredient capsule 300, unblended cosmetic product 300, to-be-blended cosmetic product 300, cosmetic liquid precursor 300, not-skin-ready cosmetic product 300, and/or blendable non-homogenous cosmetic product 300. As used herein, enclosed blending chamber 100 additionally or alternatively may be referred to as blending chamber 100, mixing chamber 100, heating and blending chamber 100, melting and blending chamber 100, blending compartment 100, and/or emulsification chamber 100. As used herein, cosmetic liquid 330 additionally or alternatively may be referred to as liquid skin care formulation 330, final cosmetic product 330, skin-ready liquid cosmetic product 330, ready-to-use liquid cosmetic product 330, final product 330, homogenous liquid cosmetic product 330, and/or heated and blended liquid cosmetic product 330.

Blending chamber 100 may be sized, configured, adapted, designed, and/or constructed to contain, retain, and/or hold solid-shell cosmetic ingredient capsule 300 and/or cosmetic liquid 330. As examples, blending chamber 100 may define and/or have a volume of at least 1 milliliters (ml), at least 2 ml, at least 3 ml, at least 4 ml, at least 5 ml, at least 6 ml, at least 7 ml, at least 8 ml, at least 9 ml, at least 10 ml, at least 15 ml, at least 20 ml, at most 400 ml, at most 350 ml, at most 300 ml, at most 250 ml, at most 200 ml, at most 150 ml, at most 100 ml, at most 50 ml, at most 45 ml, at most 40 ml, at most 35 ml, at most 30 ml, at most 25 ml, at most 20 ml, at most 18 ml, at most 16 ml, at most 14 ml, at most 12 ml, at most 10 ml, and/or at most 8 ml. This volume does not include the volume of the blending element. Thus, the volume of the blending chamber is the volume of empty space in the blending chamber 100 when the blending chamber is empty (i.e., does not include solid-shell cosmetic ingredient capsule 300 and/or cosmetic liquid 330). When solid-shell cosmetic ingredient capsule 300 and/or cosmetic liquid 330 are included in blending chamber 100, the volume of blending chamber 100 therefore includes the volume of the volume of solid-shell cosmetic ingredient capsule 300 and/or cosmetic liquid 330.

As mentioned above, blending chamber 100 may be enclosed and/or formed when lid 20 and base 60 are in the closed position. Thus, the closed position is a position in which lid 20 and base 60 may fully enclose blending chamber 100. In some examples, lid 20 and base 60 may be configured to provide a fluid seal between blending chamber 100 and the outside of cosmetic blending device 10 when the lid and the base are in the closed position. For example, lid 20 and base 60 may be in direct, sealing contact with one another in the closed position. Thus, lid 20 and base 60 may be configured to prevent leakage of any contents of solid-shell cosmetic ingredient capsule 300 and/or cosmetic liquid 330 to the outside of cosmetic blending device 10 when the lid and the base are in the closed position. As such, blending chamber 100 may be and/or may define, an enclosed, empty space within cosmetic blending device 10, such as between lid 20 and base 60, when lid 20 and base 60 are in the closed position. As will be discussed in greater detail below, blending element 22 may extend into blending chamber 100 and occupy at least a portion of the enclosed empty space of the blending chamber when the lid and the base are in the closed position. In particular, blending element 22 may extend into blending chamber 100 from above solid-shell cosmetic ingredient capsule 300, when solid-shell cosmetic ingredient capsule 300 is positioned in lower portion 102 of blending chamber 100, such as bowl-shaped depression 64.

In the open position, lid 20 and base 60 may not define enclosed blending chamber 100. In particular, adjusting lid 20 and base 60 to the open position may open up blending chamber 100 and expose portions of lid 20 and base 60 that are inaccessible to a user when the lid and the base are in the closed position. For example, base 60 may include a top 62, at least a portion of which may form lower portion 102 of blending chamber 100 when lid 20 and base 60 are in the closed position. However, in the open position, top 62 of base 60 may be directly accessible to a user. Similarly, lid 20 may include a bottom 40, at least a portion of which may form and/or define an upper portion 104 of blending chamber 100 when lid 20 and base 60 are in the closed position. However, in the open position, bottom 40 of lid 20 may be directly accessible to a user.

Lid 20 and base 60 may be configured to be selectively adjusted between the open and closed positions by selectively repositioning lid 20 and base 60 relative to one another. For example, lid 20 and base 60 may be configured to be rotated, pivoted, and/or translated with respect to one another to adjust between the open and closed positions.

Cosmetic blending device 10 may include a coupling structure 130 that is configured to selectively permit lid 20 and base 60 to adjust between the open and closed positions. Additionally or alternatively, coupling structure 130 may be configured to selectively retain and/or lock lid 20 and base 60 in the closed position and/or selectively release lid 20 and base 60 to be transitioned to the open position. That is, coupling structure 130 may be configured to selectively restrict relative movement between lid 20 and base 60 and/or to hold lid 20 and base 60 in the closed position when lid 20 and base 60 are in the closed position, while still selectively permitting lid 20 and base 60 to adjust to the open position when desired by a user. Coupling structure 130 additionally or alternatively may be configured to permanently couple lid 20 and base 60 (even when lid 20 and base 60 are in the open position), while still permitting lid 20 and base 60 to adjust between the open and closed positions.

Coupling structure 130 may include a mechanical coupling structure 132 and/or a magnetic coupling structure 144 that is/are configured to bias, retain, keep, and/or otherwise hold lid 20 and base 60 in the closed position. Such a configuration may mitigate, and/or prevent un-commanded and/or otherwise undesirable adjustment towards and/or to the open position, such as during a blending cycle when blending element 22 is moving. In this way, coupling structure 130 may reduce and/or prevent spilling and/or leaking of the contents contained in blending chamber 100 (e.g., solid-shell cosmetic ingredient capsule 300 and/or cosmetic liquid 330) and/or may restrict access to the blending chamber when blending element 22 is actuated or otherwise moving (e.g., spinning). In particular, the coupling structure 130 may exert a holding, or retaining, force that opposes and/or is greater than a maximum force exerted on lid 20 by drive mechanism 120 and/or blending element 22. For example, when blending element 22 is configured to spin in a counterclockwise direction, drive mechanism 120 and/or blending element 22 may exert a countervailing clockwise torque on lid 20. This countervailing clockwise torque may urge lid 20 to spin in a clockwise direction if nothing is holding lid 20 in place. However, in such examples, coupling structure 130 may exert a holding torque oriented in the opposite, counterclockwise direction that is greater than the clockwise torque exerted by drive mechanism 120 and/or blending element 22 on lid 20, and therefore sufficient to hold lid 20 and base 60 in the closed position.

Additionally or alternatively, coupling structure 130 may be configured to be self-locking. That is, coupling structure 130 may be configured to utilize the force exerted on lid 20 by drive mechanism 120 and/or blending element 22 to bias lid 20 and base 60 towards the closed position. As an example, when blending element 22 is configured to spin within blending chamber 100 during a blending cycle, coupling structure 130 may be configured such that the force exerted by blending element 22 and/or drive mechanism 120 on lid 20 increases the holding force between lid 20 and base 60. In particular, when blending element 22 is configured to spin in a counterclockwise direction, the coupling structure 130 may be configured to increase an amount of friction between lid 20 and base 60. As one example, coupling structure 130 may include mating threads and/or grooves that may be configured to tighten lid 20 and/or base 60 in a rotational direction opposite to the rotational direction of blending element 22.

Coupling structure 130 additionally or alternatively may be configured to selectively permit adjustment of lid 20 and/or base 60 towards the open position when desired. For example, a user may desire to adjust lid 20 and/or base 60 towards or to the open position before initiating a blending cycle in order to insert solid-shell cosmetic ingredient capsule 300 into cosmetic blending device 10, and/or after a blending cycle has completed in order to remove, extract, and/or apply cosmetic liquid 330. A blending cycle may comprise a single heating (or heating and cooling) and blending sequence in which cosmetic blending device 10 receives at least one solid-shell cosmetic ingredient capsule 300 and produces cosmetic liquid 330 therefrom. Thus, a blending cycle may begin when the cosmetic blending device initiates the heating and/or blending (after a user has inserted solid-shell cosmetic ingredient capsule 300 and adjusted the lid and the base to the closed position) and a blending cycle may terminate when the cosmetic blending device finishes the heating (or heating and cooling) and blending, and cosmetic liquid 330 is ready for extraction (i.e., when solid-shell cosmetic ingredient capsule 300 has been converted and/or transformed to cosmetic liquid 330 and/or when cosmetic blending device 10 alerts and/or notifies a user that the cosmetic liquid is ready for extraction).

A blending cycle may include one or more different periods, portions, and/or times. As an example, a blending cycle may include one or more of a warm-up period during which only the thermal element is powered on and the solid-shell cosmetic ingredient capsule is heated, a ramp-up period during which the drive mechanism is powered on and brought up to a desired rotational speed and/or in which the drive mechanism is driven at a speed and/or direction to facilitate segmenting of and thermal transfer to the shell of the solid-shell cosmetic ingredient capsule, a main blending sequence during which the drive mechanism operates at the desired rotational speed and where a majority of the mixing and blending occurs, and/or a cool down period where the drive mechanism is powered down and/or off and/or where the thermal element is adjusted (powered off and/or switched from a heating mode to a cooling mode) to cool the cosmetic liquid to a user-friendly (and optionally user-selected) temperature. Thus, different periods of a blending cycle may be categorized based on the processes performed during those periods. Stated slightly differently, a blending cycle may be broken down into one or more different periods, portions, and/or times based on differences/changes in the operations performed during those periods, portions, and/or times.

In some examples, coupling structure 130 may be configured to only release lid 20 and base 60 from the closed position (and thus permit adjustment towards the open position) when manually adjusted by a user. For example, coupling structure 130 may require that a user physically turn lid 20 and base 60 relative to one another in order to adjust lid 20 and base 60 towards the open position. As a further example, when coupling structure 130 is configured to be self-locking, coupling structure 130 may require that a user physically move (e.g., rotate, translate, and/or pivot) lid 20 and base 60 with enough force to overcome the frictional forces holding lid 20 and base 60 in the closed position. When coupling structure 130 is not configured to be self-locking, coupling structure may require that a user physically move lid 20 and base 60 relative to one another with a greater force than the maximum force exerted on lid 20 by blending element 22 and/or drive mechanism 120. Additionally or alternatively, a user may have to disengage one or more locking fasteners (e.g., latches, pin and sockets, etc.) in order to release lid 20 and base 60 from the closed position.

Mechanical coupling structure 132 may be configured to selectively restrict relative movement (e.g., translation, rotation, and/or pivoting) between lid 20 and base 60 via mechanical forces (e.g., friction). In particular, mechanical coupling structure 132 may include a releasable locking structure 134 that is configured to restrict relative movement between lid 20 and base 60. In particular, and as introduced above, releasable locking structure 134 may be configured to hold and/or retain lid 20 and base 60 in the closed position, and additionally or alternatively may be configured to selectively release lid 20 and base 60 when actuated by a user and/or only when actuated by a user.

Releasable locking structure 134, when present, may include one or more of threads, friction fits, bayonet locks, pins and sockets, and/or other locking fasteners. For example, and as described in greater detail herein in connection with FIGS. 3 and 9-10, when releasable locking structure 134 includes a threaded engagement between lid 20 and base 60, lid 20 and base 60 may each include threads and/or grooves that are configured to mate with one another. As an example, both lid 20 and base 60 may include multiple threads (each including ridges and grooves). In another example, the releasable locking structure 134 may include only one ridge and one groove. In such examples, only one of lid 20 or base 60 may include the ridge, and the other may include the mating groove. For example, an exterior-facing surface of a top edge 76 of base 60 may include a set of ridges, and an interior-facing surface of a bottom edge 44 of lid 20 may include a set of mating grooves.

The threaded engagement may be configured to tighten (e.g., lid 20 may be configured to thread farther onto base 60) in a first rotational direction (e.g., clockwise) and to loosen in a second rotational direction opposite the first rotational direction. Thus, lid 20 may be threaded onto base 60 to adjust lid 20 and base 60 to the closed position by rotating lid 20 in the first rotational direction. Once threaded onto base 60, friction between the mating threads and/or grooves in lid 20 and base 60 may hold lid 20 and base 60 in the closed position. As mentioned above, a rotational direction of blending element 22 additionally or alternatively may bias lid 20 towards the closed position. In particular, blending element 22 may spin in a rotational direction that is opposite the first rotational direction (e.g., the tightening direction of the threaded engagement). For example, when the threaded engagement is configured to tighten in a clockwise direction, blending element 22 may be configured to spin in the counterclockwise direction, and vice versa. In this way, coupling structure 130 may be self-locking (i.e., the forces exerted on lid 20 by drive mechanism 120 and/or blending element 22 may be configured to bias lid 20 and base 60 towards the closed position), thereby reducing and/or eliminating the need for additional locking and/or holding structures. In particular, the force exerted on lid 20 by blending element 22 and/or drive mechanism 120 may be sufficient by itself to hold lid 20 and base 60 in the closed position during a blending cycle.

As described above, bayonet locks, pins and sockets, and/or other locking fasteners additionally or alternatively may be included in the releasable locking structure 134 to help keep lid 20 and base 60 locked in the closed position. As one example, releasable locking structure 134 may include a latch that is configured to be manually adjusted between a locked position and an unlocked position by a user. When in the locked position, the latch may restrict lid 20 and base 60 from being adjusted from the closed position towards and/or to the open position. Once in the unlocked position, the latch may permit lid 20 and base 60 to be adjusted from the closed position to the open position. As another example, the mechanical fastener may comprise a flexible pin-and-socket arrangement that is configured to be manually adjusted between a locked position and an unlocked position by a user. As an example, the pin may be biased (e.g., via a spring or other resilient structure) to an extended position, in which the pin-and-socket arrangement is in the locked position. In this locked position (in which the pin is in the extended position), the pin may extend through the socket to lock lid 20 and base 60. A user may unlock the flexible pin-and-hole arrangement by pushing on the pin such that it disengages with the socket, and then rotating lid 20 and base 60.

Coupling structure 130 additionally or alternatively may include magnetic coupling structure 144. Magnetic coupling structure 144 may be configured to selectively restrict relative movement (e.g., translation, rotation, and/or pivoting) between lid 20 and base 60 and/or bias lid 20 and base 60 to the closed position via magnetic forces. In particular, lid 20 and base 60 may each include a magnet and/or ferromagnetic material. As one example, both lid 20 and base 60 may include magnets. In some such examples, lid 20 and/or base 60 additionally may include ferromagnetic material. As another example, lid 20 may include a magnet and base 60 may include a ferromagnetic material. As yet another example, lid 20 may include a ferromagnetic material and base 60 may include a magnet. In all examples, the magnets and/or ferromagnetic material in lid 20 may be configured to be magnetically attracted to other magnets and/or ferromagnetic material in base 60, such that lid 20 and base 60 are attracted to one another. The magnets and/or ferromagnetic materials in lid 20 may be at their closest approach to the magnets and/or ferromagnetic materials in base 60 when lid 20 and base 60 are in the closed position, and thus may exert a maximum attractive magnetic force when lid 20 and base 60 are in the closed position. This attractive magnetic force may help bias, retain, hold, and/or keep lid 20 and base 60 in the closed position.

Figure 3:
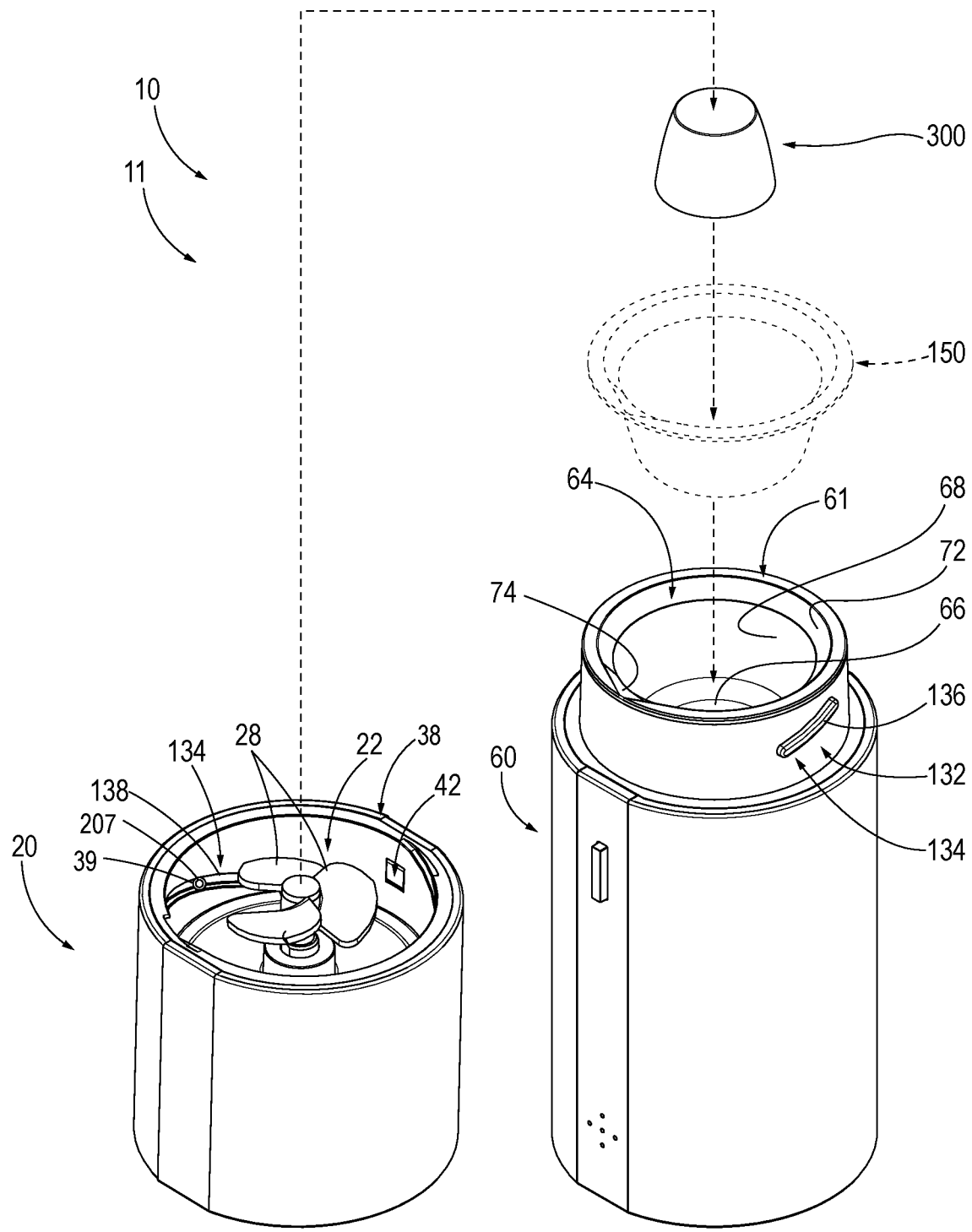
FIG. 3 is an external view of the example cosmetic blending device of FIG. 2 in an open position.

Coupling structure 130 may be configured such that, when adjusted to the open position, lid 20 and base 60 may completely detach from one another, as illustrated in FIG. 3. In other examples, lid 20 and base 60 may remain attached and/or coupled to one another in the open position. In particular, coupling structure 130 may include a permanent coupling structure 140 that may be configured to permanently couple lid 20 and base 60 while permitting lid 20 and base 60 to be selectively adjusted between the open and closed positions. As one example, permanent coupling structure 140 may include a tether. As another example, permanent coupling structure 140 may include a hinge 141. Hinge 141 may include two pivoting flanges, with a first flange 142 connected to lid 20, and a second flange 143 connected to base 60.

In yet further examples, lid 20 and/or base 60 may not be selectively repositioned when being adjusted between the open and closed positions, however cosmetic blending device 10 may nonetheless include an access structure that is configured open and close to provide a user access to blending chamber 100. As one example, lid 20 and/or base 60 may include a door that may configured to be selectively opened to access blending chamber 100.

As discussed above, blending chamber 100 is defined by lid 20 and base 60. That is, lid 20 and base 60 may define the walls and/or boundaries of blending chamber 100. In particular, at least a portion of top 62 of base 60 may define and/or form lower portion 102 of blending chamber 100, and at least a portion of bottom 40 of lid 20 may define and/or form upper portion 104 of blending chamber 100.

Top 62 of base 60 may be sized, configured, adapted, designed, and/or constructed to contain, retain, receive, and/or hold solid-shell cosmetic ingredient capsule 300 and/or cosmetic liquid 330. In particular, top 62 of base 60 may include a bowl-shaped depression 64 that may be sized, configured, adapted, designed, and/or constructed to contain, retain, receive, and/or hold solid-shell cosmetic ingredient capsule 300 and/or cosmetic liquid 330. Specifically, bowl-shaped depression 64 may be larger in volume than solid-shell cosmetic ingredient capsule 300. As examples, bowl-shaped depression 64 may have a volume (may be configured to contain, hold and/or otherwise retain a volume of fluid without the fluid overflowing) of at least 0.5 ml, at least 0.75 ml, at least 1 ml, at least 1.5 ml, at least 2 ml, at least 2.5 ml, at least 3 ml, at least 3.5 ml, at least 4 ml, at least 4.5 ml, at least 5 ml, at least 5.5 ml, at least 6 ml, at least 6.5 ml, at least 7 ml, at least 7.5 ml, at least 8 ml, at least 8.5 ml, at least 9 ml, at least 9.5 ml, at least 10 ml, at most 25 ml, at most 20 ml, at most 18 ml, at most 16 ml, at most 15 ml, at most 14 ml, at most 13 ml, at most 12 ml, at most 11 ml, at most 10 ml, at most 9 ml, at most 8 ml, at most 7 ml, at most 6 ml, at most 5 ml, at most 4 ml, at most 3 ml, and/or at most 2 ml. Thus, a user may place solid-shell cosmetic ingredient capsule 300 into and/or onto top 62 of base 60 and/or bowl-shaped depression 64 prior to heating and blending the solid-shell cosmetic ingredient capsule, and the user may extract cosmetic liquid 330 from top 62 of base 60 and/or bowl-shaped depression 64 after the cosmetic blending device heats and blends the solid-shell cosmetic ingredient capsule to form cosmetic liquid 330.

Bowl-shaped depression 64 may be and/or define a depression, cavity, concavity, and/or indentation on top 62 of base 60. In particular, bowl-shaped depression 64 may include a bottom 66 and sidewalls 68, and bottom 66 may be recessed relative to a top edge 76 of base 60. Sidewalls 68 may be angled outward from bottom 66 of bowl-shaped depression 64 such that the cross-sectional area of bowl-shaped depression 64 may be greater nearer top edge 76 of base 60 than bottom 66 of bowl-shaped depression 64. However, in other examples, sidewalls 68 may be substantially straight (i.e., orthogonal to bottom 66). A height of bowl-shaped depression 64 (i.e., a distance between bottom 66 and top edge 76) may be at least 0.5 centimeters (cm), at least 1 cm, at least 1.5 cm, at least 2 cm, at least 2.5 cm, at least 3 cm, at most 6 cm, at most 5 cm, at most 4 cm, at most 3.5 cm, at most 3 cm, and/or at most 2.5 cm. Further, a diameter of bottom 66 of bowl-shaped depression 64 may be at least 0.4 cm, at least 0.6 cm, at least 0.8 cm, at least 1 cm, at least 1.2 cm, at least 1.4 cm, at least 1.6 cm, at least 1.8 cm, at least 2 cm, at most 6 cm, at most 5 cm, at most 4 cm, at most 3 cm, at most 2.4 cm, and at most 2.2 cm, and/or at most 2 cm. Although bottom 66 is described as having a diameter, bowl-shaped depression 64 may have any suitable cross-sectional shape, with examples including, elliptical, rectangular, square, triangular, pentagonal, hexagonal, and/or other regular or irregular polygonal shapes. When bottom 66 has a non-circular shape, the above diameters of bottom 66 may be a minimum or maximum dimension (e.g., axis) of bottom 66 of bowl-shaped depression 64.

In this way, blending chamber 100, and more specifically, bowl-shaped depression 64, may be configured to hold, retain, and/or contain the entirety of solid-shell cosmetic ingredient capsule 300 and/or cosmetic liquid 330. Further, cosmetic blending device 10 may be configured to heat and/or blend the entirety of solid-shell cosmetic ingredient capsule 300. In particular, solid-shell cosmetic ingredient capsule 300 may be placed into blending chamber 100 without any packaging, and cosmetic blending device 10 may be configured to heat and/or blend the entirety of solid-shell cosmetic ingredient capsule 300 to form cosmetic liquid 330 therefrom. Thus, after the heating and/or blending, all of the solid-shell cosmetic ingredient capsule may be transformed to cosmetic liquid 330. That is, the entirety of solid-shell cosmetic ingredient capsule 300 may form the cosmetic liquid. Stated another way, the entirety of cosmetic liquid 330 may be formed from solid-shell cosmetic ingredient capsule. This may reduce and/or eliminate the need for single-use packaging, containers, disposable wrappings, and/or other waste products, thereby providing a more environmentally friendly and less wasteful cosmetic product.

Bottom 66 of bowl-shaped depression 64 may be flat and/or planar and/or at least substantially flat and/or planar. Although bottom 66 of bowl-shaped depression 64 may be perfectly flat and/or planar in some examples, it should be appreciated that it may be difficult, impractical, and/or impossible, to achieve a perfectly flat and/or planar surface in all examples. Thus, the above recitation that bottom 66 of bowl-shaped depression 64 may be at least substantially flat and/or planar should be interpreted to mean that the bottom of bowl-shaped depression 64 is intended to be, or is effectively, flat and/or planar while recognizing that it may not be practical, possible, or at least economical, to ensure that the bottom is exactly flat and/or planar in all systems, at all times, and/or under all circumstances.

However, in other examples, bottom 66 of bowl-shaped depression 64 may be curved, concave, convex, arcuate, and/or otherwise non-planar. Additionally or alternatively, bottom 66 of bowl-shaped depression 64 may include one or more indentations, concavities, and/or depressions. As one such example, bottom 66 of bowl-shaped depression 64 may include a central indentation.

Bowl-shaped depression 64 may be configured to readily transfer thermal energy from thermal element 110 to blending chamber 100, solid-shell cosmetic ingredient capsule 300 and/or cosmetic liquid 330. In particular, bowl-shaped depression 64 may be constructed from a thermally conductive material and/or a material that has a relatively low specific heat capacity. For example, bowl-shaped depression 64 may be constructed from a material having a thermal conductivity of at least 50 Watts per meter-Kelvin (W/(m·K)), at least 100 W/(m·K), at least 150 W/(m·K), and/or at least 200 W/(m·K). Additionally or alternatively, bowl-shaped depression 64 may be constructed from a material that has a specific heat capacity of at most 1100 Joules per kilogram-Kelvin (J/(kg·K)), at most 1000 J/(kg·K), and/or at most 900 J/(kg·K). As one example, bowl-shaped depression 64 may be constructed from aluminum. In other examples, bowl-shaped depression 64 may be constructed from a different metal such as copper and/or a metal alloy such as stainless steel.

Additionally or alternatively, a thickness of bowl-shaped depression 64, including a thickness of bottom 66 and/or sidewalls 68, may be sized, configured, adapted, and/or constructed to promote and/or optimize thermal transfer from thermal element 110 to blending chamber 100, solid-shell cosmetic ingredient capsule 300, and/or cosmetic liquid 330. As examples, bowl-shaped depression 64 may be sized to have a thickness of at least 0.05 cm, at least 0.075 cm, at most 0.1 cm, at most 0.125 cm, at most 0.15 cm, at most 0.2 cm, and/or at most 0.25 cm, and/or at most 0.4 cm.

However, the thickness of bowl-shaped depression 64 may be adjusted based on one or more of the strength, formability, specific heat capacity, thermal conductivity, and density of the material. For example, since stainless steel has a lower thermal conductivity than aluminum, bowl-shaped depression 64 may be thinner when constructed from stainless steel than when constructed from aluminum to provide adequate thermal transfer.

Configuring bowl-shaped depression 64 to readily transfer thermal energy may result in shorter melt times (i.e., solid-shell cosmetic ingredient capsule 300 may be liquefied more quickly), thereby reducing the duration of the heating and/or blending of the solid-shell cosmetic ingredient capsule. Further, configuring bowl-shaped depression 64 to readily transfer thermal energy may provide more even and homogenous heating of the solid-shell cosmetic ingredient capsule and the resulting cosmetic liquid.

Bowl-shaped depression 64 may include a coating on an external surface 69 that is configured to prevent degradation of bowl-shaped depression 64. For example, the coating may be configured to prevent and/or restrict chemical reactions, corrosion, and/or erosion of external surface 69. Additionally or alternatively, the coating may be configured to color external surface 69. The coating also or alternatively may be configured to facilitate cleaning and/or removal of the cosmetic liquid. The coating may be configured to be thin enough (e.g., less than 2 mm, less than 1 mm, less than 0.5 mm, and/or at least 0.1 mm) to not reduce, mitigate, and/or otherwise interfere with thermal conduction. Example coatings include one or more of anodized coatings, powder coatings, plated coatings, and ceramic coatings. External surface 69 (on which the coating may be applied) faces blending chamber 100, and may directly interface with solid-shell cosmetic ingredient capsule 300 and/or cosmetic liquid 330. That is, when a user places solid-shell cosmetic ingredient capsule 300 into blending chamber 100, the solid-shell cosmetic ingredient capsule may sit on and/or directly contact external surface 69.

Cosmetic blending device 10 additionally and/or alternatively may include a cosmetic ingredient receptacle 150 that optionally may be positioned between external surface 69 and solid-shell cosmetic ingredient capsule 300 and/or cosmetic liquid 330. Cosmetic ingredient receptacle 150 may be configured to not only retain, contain, and/or hold solid-shell cosmetic ingredient capsule 300 and/or cosmetic liquid 330, but also may be configured, adapted, and/or designed to be selectively removed from base 60. In particular, cosmetic ingredient receptacle 150 may be configured, sized, adapted, designed, and/or constructed to fit within and/or line bowl-shaped depression 64. For example, the cosmetic ingredient receptacle may include one or more of a tray, cup, dish, flexible liner, etc. Thus, a user may selectively insert solid-shell cosmetic ingredient capsule 300 into cosmetic ingredient receptacle 150, and/or may selectively remove cosmetic liquid 330 from cosmetic ingredient receptacle 150. Additionally or alternatively, a user may selectively remove cosmetic ingredient receptacle 150 from cosmetic blending device 10 before removing cosmetic liquid 330 from cosmetic ingredient receptacle 150 and/or may selectively remove cosmetic ingredient receptacle 150 to insert solid-shell cosmetic ingredient capsule 300, and then may place cosmetic ingredient receptacle 150 back in cosmetic blending device 10.

Cosmetic ingredient receptacle 150 may be reusable, and a user may repeatedly remove and/or replace cosmetic ingredient receptacle 150 to insert new solid-shell cosmetic ingredient capsules and/or remove cosmetic liquids. After placing solid-shell cosmetic ingredient capsule 300 and/or cosmetic liquid 330 into cosmetic ingredient receptacle 150, a user may initiate the heating and blending cycle and/or the cosmetic blending device may automatically initiate the heating and blending cycle. After the heating and blending cycle, a user may remove cosmetic ingredient receptacle 150 from cosmetic blending device 10 to extract cosmetic liquid 330.

In some examples, cosmetic ingredient receptacle 150, when present, may be separate from solid-shell cosmetic ingredient capsule 300. That is, solid-shell cosmetic ingredient capsule 300 and cosmetic ingredient receptacle 150 may not be packaged together. As such, solid-shell cosmetic ingredient capsule 300 may need to be placed into cosmetic ingredient receptacle 150 prior to heating and/or blending solid-shell cosmetic ingredient capsule 300. However, in other examples, solid-shell cosmetic ingredient capsule 300 may be packaged with cosmetic ingredient receptacle 150. As an example, cosmetic ingredient receptacle 150 may form at least a portion of the packaging of the solid-shell cosmetic ingredient capsule 300 and/or otherwise may be configured to protect solid-shell cosmetic ingredient capsule 300 from damage during shipping, handling, and storage. In such examples, a user may not need to place solid-shell cosmetic ingredient capsule 300 into cosmetic ingredient receptacle 150 prior to heating and/or blending solid-shell cosmetic ingredient capsule 300 because solid-shell cosmetic ingredient capsule 300 already may be included within the cosmetic ingredient receptacle.

In all of the above examples, cosmetic ingredient receptacle 150 may be configured to store, or contain, cosmetic liquid 330 produced by cosmetic blending device 10. As an example, after heating and/or blending the solid-shell cosmetic ingredient capsule, a user may remove cosmetic ingredient receptacle 150 (and cosmetic liquid 330 contained therein) from the cosmetic blending device, and may extract the cosmetic liquid from the cosmetic ingredient receptacle as desired over a period of time (at a desired rate, rather than all at once). Utilizing such cosmetic ingredient receptacles may enable a user to produce multiple cosmetic liquids 330. That is, the cosmetic blending device may be operated repeatedly (i.e., over multiple cycles) to produce multiple cosmetic liquids 330 that may each be stored in separate cosmetic ingredient receptacles 150. Thus, cosmetic ingredient receptacle 150 may allow a user to store the cosmetic liquid for later use, and/or to prepare multiple cosmetic liquids in a short period of time to be used concurrently.

Additionally or alternatively, cosmetic ingredient receptacle 150 may enable easier cleaning of the cosmetic blending device. In particular, because the cosmetic ingredient receptacle may hold all of the cosmetic liquid, a user may not need to clean bowl-shaped depression 64 as often in between blending cycles as a user does if cosmetic ingredient receptacle 150 is omitted. Further, because cosmetic ingredient receptacle 150 may be removable, it may be easier to rinse and clean than bowl-shaped depression 64.

In yet further examples, cosmetic ingredient receptacle 150 may be omitted, but bowl-shaped depression 64 may be configured to be selectively removed and/or coupled to base 60. For example, bowl-shaped depression 64 and/or base 60 may include depression coupling structures 152 that may be configured to selectively couple and decouple base 60 and bowl-shaped depression 64. When coupled to base 60, cosmetic ingredient receptacle 150 may be configured to not move during a blending cycle, and may only move between blending cycles, when desired by a user (i.e., may require an external, user-provided force to decouple from base 60). As one such example, depression coupling structures 152 may include a flexible snap-fit arrangement in which bowl shaped depression 64 may clip into and out of base 60. Additionally or alternatively, depression coupling structures 152 may include any other coupling structures that are suitable to selectively couple and decouple base 60 and bowl-shaped depression 64, such as any of the example coupling structures of coupling structure 130 discussed above.

Blending element 22 extends into blending chamber 100 when lid 20 and base 60 are in the closed position. For example, blending element 22 may extend into blending chamber 100 from lid 20 when lid 20 and base 60 are in the closed position. In particular, blending element 22 may include a shaft 24 that extends into blending chamber 100. When blending element 22 is included in the lid, shaft 24 may extend downward, below at least a portion of bottom 40 of lid 20 when lid 20 and base 60 are in the closed position. In particular, bottom 40 of lid 20 may include a cavity 42 that is recessed from bottom edge 44 of lid 20, and blending element 22 may extend below at least the cavity. In the description herein, the terms up, down, above, and below may be used to describe the relative positioning of components of cosmetic blending device 10 along a vertical axis 250. Thus, components described as being above one or more other components may be positioned at a more positive position, further along vertical axis 250, and vice versa.

Blending element 22 may extend into lower portion 102 of blending chamber 100 toward bottom 66 of bowl-shaped depression 64, and/or even into contact with bottom 66 of bowl-shaped depression 64. In particular, blending element 22 may extend into blending chamber 100 from above solid-shell cosmetic ingredient capsule 300, when solid-shell cosmetic ingredient capsule 300 is positioned in bowl-shaped depression 64. Thus, blending element 22 may blend solid-shell cosmetic ingredient capsule 300 from above. In the description herein, the terms above and below may be used to reference the relative positioning of components with respect to gravity. Thus, the blending element 22 may be above solid-shell cosmetic ingredient capsule 300 with respect to a direction of the gravitational force of Earth (i.e., at least a portion of blending element 22 and lid 20 may be farther from Earth's center of mass than base 60). When cosmetic blending device 10 is positioned on a surface (e.g., table, countertop, etc.) base 60 may be positioned below lid 20, and thus it is base 60 that may be placed on and/or directly interface with the surface. Thus, cosmetic blending device 10 may be positioned in the orientation depicted in FIG. 2, for example, when heating and/or blending the solid-shell cosmetic ingredient capsule.

In some examples, blending element 22 may extend to within close proximity of bottom 66 of bowl-shaped depression 64, but may not actually touch bottom 66 of bowl shaped depression. In particular, a bottom 26 of blending element 22 and/or shaft 24 may be separated from (spaced above) bottom 66 of bowl-shaped depression 64 by at least at least 0.5 millimeters (mm), at least 1 mm, at least 1.5 mm, at least 2 mm, at least 2.5 mm, at least 3 mm, at least 3.5 mm, at least 4 mm, at least 4.5 mm, at least 5 mm, at most 10 mm, at most 9 mm, at most 8 mm, at most 7 mm, and/or at most 6 mm, when lid 20 and base 60 are in the closed position. Spacing blending element 22 away from bottom 66 of bowl-shaped depression 64 may reduce contact friction (e.g., rubbing) between blending element 22 and bowl-shaped depression 64, thereby reducing potential degradation of these components. Further, spacing blending element 22 from bottom 66 of bowl-shaped depression 64 may facilitate better blending (e.g., more homogenous, even blending) of solid-shell cosmetic ingredient capsule 300 because the space between the blending element and the bowl-shaped depression may increase turbulence of heated fluid below the blending element, and may limit and/or reduce the formation of large chunks of solid cosmetic material. In particular, the space between the blending element and the bowl-shaped depression may reduce an amount of cosmetic material that is pushed between cutting edges of the blending element. However, in other examples, blending element 22 may extend all the way to bottom 66 of bowl-shaped depression 64 such that it physically contacts bottom 66 when lid 20 and base 60 are in the closed position.

Further, shaft 24 may be configured to extend far enough into blending chamber 100, (e.g., far enough from lid 20 towards bottom 66 of bowl-shaped depression 64), to make contact with solid-shell cosmetic ingredient capsule 300 when lid 20 and base 60 are in the closed position. In some examples, bottom 26 of blending element 22 may be configured to crush, compress, flatten, deform, squash, splinter, puncture, and/or otherwise break up solid-shell cosmetic ingredient capsule 300 when lid 20 and base 60 are adjusted to the closed position. In particular, when separated from bottom 66 of bowl-shaped depression 64, the distance separating bottom 26 of blending element 22 from bottom 66 of bowl-shaped depression 64 may be less than one or more of a height, width, length, and/or radius of solid-shell cosmetic ingredient capsule 300. Thus, blending element 22 may compress solid-shell cosmetic ingredient capsule 300 between bottom 26 of blending element 22 and bottom 66 of bowl-shaped depression 64 when the cosmetic blending device is adjusted from the open position to the closed position.

As mentioned above, bottom 26 of blending element 22 may be configured to facilitate piercing, crushing, squashing, splintering, puncturing, and/or otherwise breaking of solid-shell cosmetic ingredient capsule 300. As one example, bottom 26 may be flat and may be particularly suitable for crushing, squashing, and/or compressing the solid-shell cosmetic ingredient capsule. In particular, when bottom 26 is flat, it may facilitate better blending (e.g., more homogenous, even blending) of solid-shell cosmetic ingredient capsule 300 because the flat bottom may not only puncture solid-shell cosmetic ingredient capsule 300 via the applied compressive force, but it also may hold solid-shell cosmetic ingredient capsule 300 in position and restrict solid-shell cosmetic ingredient capsule 300 from moving around within blending chamber 100 and/or otherwise avoiding the blending element. As another example, bottom 26 may be substantially flat, but additionally may include a pointed tip that may be particularly suitable for initially piercing the solid-shell cosmetic ingredient capsule. In yet further examples, bottom 26 may be curved, pointed, convex, and/or may include one or more projections, fins, cutting edges, etc.

As described above, blending element 22 is configured to blend solid-shell cosmetic ingredient capsule 300 in blending chamber 100. Thus, blending element 22 additionally or alternatively may include one or more cutting edges 28. Cutting edges 28 may be configured to cut, slice, mix, blend, liquefy, and/or homogenize solid-shell cosmetic ingredient capsule 300. Cutting edges 28 include at least one cutting edge 28, at least two cutting edges 28 (e.g., a forked design), at least three cutting edges 28, at least four cutting edges 28, at least five cutting edges 28, at least six cutting edges 28, at least seven cutting edges 28, at least eight cutting edges 28, at most eight cutting edges 28, at most seven cutting edges 28, at most six cutting edges 28, at most five cutting edges 28, and/or at most four cutting edges 28. Regardless of the number of cutting edges included on blending element 22, each cutting edge 28 may comprise one or more of a propeller, blade, fin, and/or other sharp and/or curved surface suitable for blending solid-shell cosmetic ingredient capsule 300. As used herein, cutting edges 28 additionally or alternatively may be referred to as curved cutting edges 28, blades 28, propeller blades 28, angled fins 28, leading edges 28, and/or forked cutting edges 28.

Figure 11:
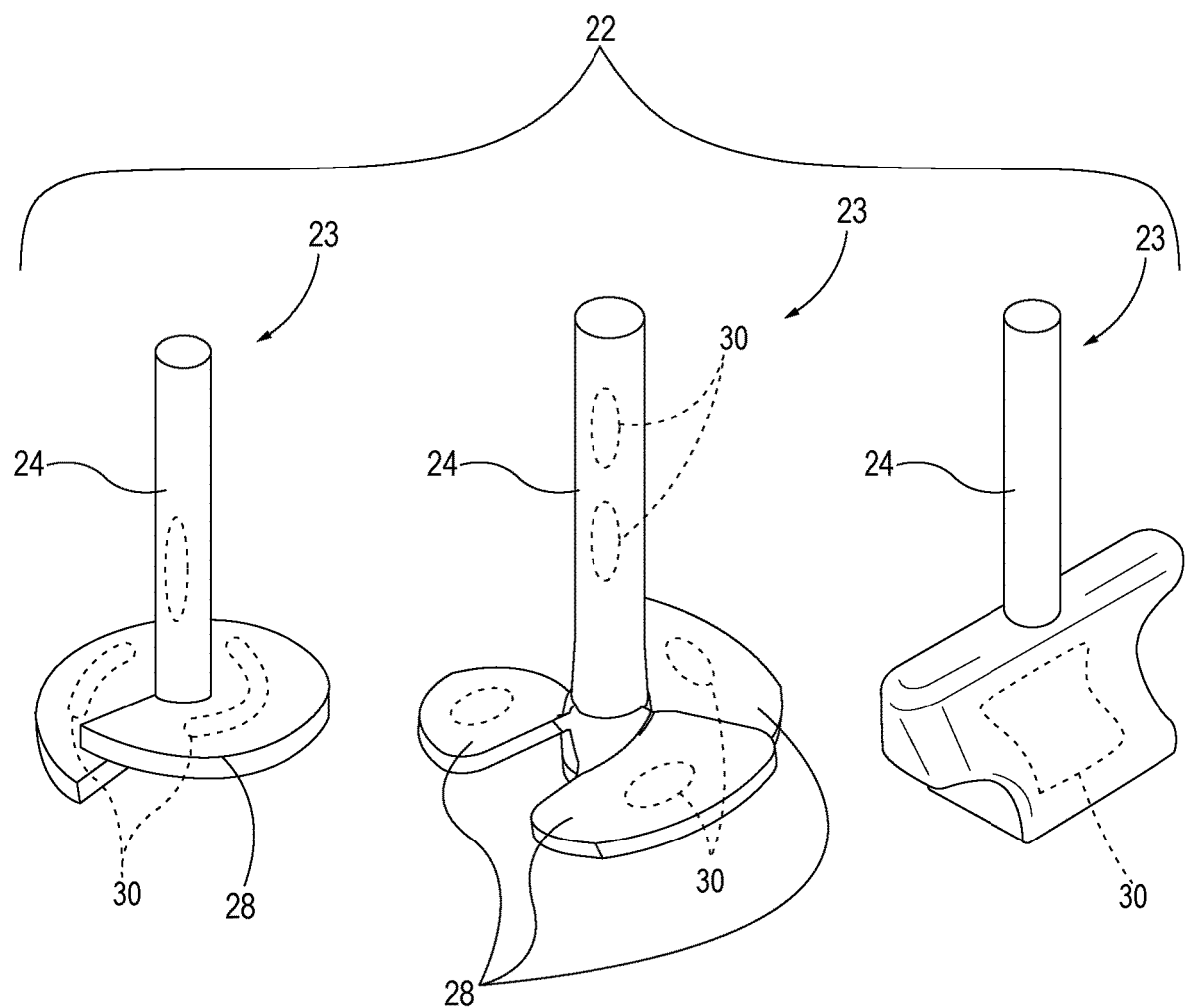
FIG. 11 is an isometric view of example blending elements of the cosmetic blending devices of FIG. 1.

Cutting edges 28 may be coupled to and/or integrally formed with shaft 24, and may extend outward and/or upward from shaft 24. In particular, cutting edges may extend upward towards lid 20 and away from bottom 26 of blending element 22. As one example, cutting edges 28 may comprise propeller-like blades that may define a pitch angle relative to shaft 24. Additionally or alternatively, one or more of the cutting edges may extend downward, towards base 60. As one example, blending element 22 may include a forked cutting edge (i.e., two cutting edges). In such examples, one of the cutting edges may angle downwards, while the other cutting edge may angle upwards, such as is illustrated in FIG. 11.

As a further example, the angle of the cutting edges may be selected to force, press, or otherwise urge the solid-shell cosmetic ingredient capsule (or portions thereof after initial blending thereof) against the bottom of the blending chamber or to urge the solid-shell cosmetic ingredient capsule (or portions thereof) away from the bottom of the blending chamber, depending upon the direction in which the blending element is rotationally driven. Urging the solid-shell cosmetic ingredient capsule against the bottom of the mixing chamber may increase the shear forces imparted to the solid-shell cosmetic ingredient capsule's shell (or portions thereof) by the blending element and/or may increase heat transfer to the solid-shell cosmetic ingredient capsule by the device's thermal elements. This may be beneficial during initial blending of the solid-shell cosmetic ingredient capsule and/or otherwise during an initial or ramp-up period of the blending cycle. Urging the solid-shell cosmetic ingredient capsule (or portions thereof and/or the cosmetic liquid being formed therefrom) away from the base of the mixing chamber may provide a scraping or redistribution of any solid or heavier portions that otherwise may accumulate on or proximate the bottom of the blending chamber.

Regardless of the blade orientation, one or more of the cutting edges may be substantially flush with bottom 26 of blending element 22 and/or may form a portion of bottom 26 of blending element 22 and may extend upwards from bottom 26 of blending element 22. However, in other examples, the cutting edges may be positioned above bottom 26 of blending element 22. As one example, shaft 24 may extend below cutting edges 28 and alone may define bottom 26 of blending element 22. Said another way, the cutting edges may be set above the bottom of shaft 24.

Blending element 22 (e.g., shaft 24 and/or cutting edges 28) may be constructed from a rigid and/or elastomeric plastic. Additionally or alternatively, blending element 22 may be constructed from a thermally conductive material and/or a material that has a relatively low specific heat capacity. For example, blending element 22 may be constructed from a material having a thermal conductivity of at least 50 W/(m·K), at least 100 W/(m·K), at least 150 W/(m·K), and/or at least 200 W/(m·K). Additionally or alternatively, blending element 22 may be constructed from a material that has a specific heat capacity of at most 1100 J/(kg·K), at most 1000 J/(kg·K), and/or at most 900 J/(kg·K).

As one example, blending element 22 may be constructed from aluminum. In other examples, blending element 22 may be constructed from a different metal, such as copper and/or a metal alloy, such as stainless steel. In yet further examples, blending element 22 may be constructed from a combination of different materials. As one example, portions of blending element 22 (e.g., shaft 24) may be constructed from a plastic, while cutting edges 28 may be constructed from a metal and/or a metal alloy. Further, blending element 22 may include one or more of hollow interior regions, apertures, holes, cut-outs, indentations, and/or voids 30 (as illustrated schematically in dashed lines in FIG. 11) to reduce a weight of the blending element, and therefore reduce an amount of force required to spin blending element 22.

Blending element 22 may include a coating, similar to bowl-shaped depression 64. Thus, the coating may be configured prevent degradation of blending element 22, to color external blending element 22, and/or to facilitate cleaning and/or removal of cosmetic liquid 330. In some examples, the color of the coating may be configured to at least substantially match the color of the bowl-shaped depression 64. Example coatings include one or more of anodized coatings, powder coatings, plated coatings, and ceramic coatings.

Constructing blending element 22 from a thermally conductive material and/or a material having a relatively low specific heat capacity may facilitate more even and complete heating and/or blending of solid-shell cosmetic ingredient capsule 300. In particular, blending element 22 may distribute more thermal energy to solid-shell cosmetic ingredient capsule 300 via cutting edges 28 and/or shaft 24 when constructed from a thermally conductive material, which in turn may facilitate more even and complete heating and/or blending of solid-shell cosmetic ingredient capsule 300, resulting in a more homogenous cosmetic liquid 330. Stated another way, constructing blending element 22 from a thermally conductive material may liquefy solid-shell cosmetic ingredient capsule 300 faster and/or ensure that solid-shell cosmetic ingredient capsule 300 completely melts during the heating and blending cycle.

Including the blending element 22 in the lid, as opposed to the base, of cosmetic blending device 10 may increase ease of cleaning the cosmetic blending device, reduce user hazards, and/or increase blending effectiveness. In particular, cosmetic liquid 330 may be at least partially and/or entirely contained within bowl-shaped depression 64. Thus, when blending element 22 is included in lid 20, the blending element may not interfere with the dispensing, extracting, and/or removal of cosmetic liquid 330 from bowl-shaped depression 64. This may reduce risk of injury to a user if a user reaches into the bowl-shaped depression 64 to extract the cosmetic liquid. Further, it may enable easier cleaning of the cosmetic liquid 330 from the bowl-shaped depression in-between blending cycles.

In some examples, blending element 22 may be configured to be selectively detached from and reattached to lid 20. In some such examples, blending element 22 may be selectively coupled to lid 20 via a coupling structure, such as any one or more of the example coupling structures discussed above of coupling structure 130. A removable blending element 22 may be removed for cleaning and/or for replacement, such as if the blending element is damaged or worn or if a different style, size, or type of blending element is desired to be used. In this latter example, it is within the scope of the present disclosure that cosmetic blending device 10 may selectively and interchangeably utilize a selected one of a plurality of blending elements 22, and a user may install a particular blending element based on the solid-shell cosmetic ingredient capsule 300 that the user intends to utilize in the cosmetic blending device. However, in other examples, blending element 22 may not be detachable, and may be permanently coupled to, and/or included within, lid 20. A removable blending element may be easier to clean than one that is permanently attached to the lid.

Additionally or alternatively, the blending element 22 may blend the solid-shell cosmetic ingredient capsule and/or cosmetic liquids more evenly when included in the lid as opposed to the base. For example, when blending element 22 is included in base 60, gravity may pull pieces of solid-shell cosmetic ingredient capsule towards the shaft, thereby lodging these pieces in-between the cutting edges of the blending element. These chunks may not blend with the rest of the cosmetic liquid, resulting in a chunkier, less homogenous final product. However, by including the blending element in the lid, gravity may naturally pull pieces of the solid-shell cosmetic ingredient capsule away from the shaft of the blending element, and may keep a larger proportion of the solid-shell cosmetic ingredient capsule at the tips of the curved cutting edges, where the cutting edges are most effective. Stated differently, including the blending element in the lid may inhibit chunks of the solid-shell cosmetic ingredient capsule from developing and becoming stuck in-between the cutting edges of the blending element and may encourage more even, homogenous blending of solid-shell cosmetic ingredient capsule 300.

Thermal element 110 may be configured to change a temperature within blending chamber 100, and more specifically, may be configured to change a temperature of solid-shell cosmetic ingredient capsule 300 and/or cosmetic liquid 330. As one example, thermal element 110 may be configured to heat (i.e., increase the temperature of) solid-shell cosmetic ingredient capsule 300. In particular, thermal element 110 may be configured to heat solid-shell cosmetic ingredient capsule 300 and/or cosmetic liquid 330 to, and/or above, the melting temperature of the solid-shell cosmetic ingredient capsule. As examples, thermal element 110 may be configured to heat solid-shell cosmetic ingredient capsule 300 and/or cosmetic liquid 330 in blending chamber 100 to at least 27° C., at least 28° C., at least 29° C., at least 30° C., at least 31° C., at least 32.2° C., at least 33° C., at least 34° C., at least 35° C., at least 36° C., at least 37° C., at least 38° C., at most 62° C., at most 61° C., at most 60° C., at most 59° C., at most 58° C., at most 56° C., at most 54° C., at most 52° C., at most 50° C., at most 49° C., and/or at most 48° C. Additionally or alternatively, and as discussed above, thermal element 110 may be configured to heat blending element 22 since blending element 22 is included in blending chamber 100. In some such examples, thermal element 110 may be included in blending element 22, as schematically illustrated in FIG. 1.

Thermal element 110 may comprise at least one thermal element 110, at least two thermal elements 110, at least three thermal elements 110, at least four thermal elements 110, at least five thermal elements 110 and/or at least six thermal elements 110 that may be positioned at one or more positions around the exterior of blending chamber 100. As one example, thermal element 110 may be positioned around an exterior of lower portion 102 of blending chamber 100 (interior of base 60). As illustrated in FIG. 1, thermal element 110 may be positioned around an outside of blending chamber 100 (i.e., within lid 20 and base 60) to transfer thermal energy to blending chamber 100. In particular, thermal element 110 may be positioned around an outside of lower portion 102 of blending chamber 100. For example, thermal element 110 may be positioned around bottom 66 of bowl-shaped depression 64 and/or sidewalls 68 of bowl-shaped depression 64. More specifically, thermal element 110 may be in direct, interfacing contact with an internal surface 70 of bowl-shaped depression 64 and/or may be coupled to internal surface 70 of bowl-shaped depression 64. Additionally or alternatively, thermal element 110 may be positioned around upper portion 104 of blending chamber 100, such as around cavity 42 of lid 20. Thermal element 110 additionally or alternatively may be positioned proximate to, within, and/or adjacent to blending element 22 to transfer thermal energy to blending element 22.

Regardless of where thermal element 110 is included around blending chamber 100, thermal element 110 may be positioned proximate bowl-shaped depression 64 to reduce energy losses and/or increase energy transfer between thermal element 110 and blending chamber 100. In particular, thermal element 110 may be positioned proximate the walls of the blending chamber (e.g., cavity 42, bottom 66, and sidewalls 68). In other words, thermal element 110 may be positioned adjacent to blending chamber 100. In particular, thermal element 110 may be positioned in direct, physical contact with the walls (e.g., cavity 42, bottom 66, and sidewalls 68) of blending chamber 100 and/or may be coupled to the interior surfaces of the walls of blending chamber 100. As used herein "internal" or "interior" surfaces refer to surfaces that are opposite external or exterior surfaces and face towards the inside of lid 20 and/or base 60. Thus, internal surface 70 is opposite external surface 69 and faces inwards, towards the interior/inside of base 60. As such, thermal element 110 may be on an opposite side of bowl-shaped depression 64 (i.e., the interior side) from solid-shell cosmetic ingredient capsule 300, which as discussed above, may be placed onto external surface 69 of bowl-shaped depression 64. This configuration may ensure that thermal element 110 is isolated from fluids in blending chamber 100 (e.g., cosmetic liquid 330), thereby preventing damage to thermal element 110.

Thermal element 110 may comprise any suitable structure that is configured to heat blending chamber 100. In particular, the thermal element 110 may comprise one or more materials, such as a metal, a metal alloy, ceramic, glass, and/or a polymer that is/are configured to increase in electrical resistivity and/or temperature when supplied an electric current and/or when subjected to an electric field. Further, the thermal element 110 may be arranged in any suitable configuration, such as one or more of a coiled heating element, a thick film heating element, a printed heating element, an electric circuit, etc. As one example, thermal element 110 may comprise a flex circuit (e.g., an electric circuit mounted and/or printed on a flexible plastic substrate). As another example, thermal element 110 may comprise an electrically resistive wire. By heating blending chamber 100 and/or solid-shell cosmetic ingredient capsule 300, thermal element 110 may facilitate blending of the solid-shell cosmetic ingredient capsule 300 to produce a cosmetic liquid from the shell and the cosmetic material of the capsule. In particular, the thermal element 110 may soften and/or liquefy solid-shell cosmetic ingredient capsule 300, thereby facilitating even and homogenous blending by blending element 22, something that would not be possible if a user attempted to manually melt and mix the shell and cosmetic material of the capsule by rubbing the capsule on the user's body. Further, heating solid-shell cosmetic ingredient capsule 300 and/or cosmetic liquid 330 may enhance user experience by ensuring that the cosmetic liquid 330 is warm to the touch when presented for extraction. As discussed, the heated cosmetic liquid also may be more easily absorbed by the user's skin or other body part, as compared to an otherwise identical unheated cosmetic liquid. Heating solid-shell cosmetic ingredient capsule 300 and/or cosmetic liquid 330 also may reduce the chance that the cosmetic liquid feels cold to a user. Instead, the cosmetic liquid 330 may provide a warmer, more soothing experience for a user, as compared to conventional cosmetics that are stored at room temperature.

In addition to, and/or instead of being configured to heat blending chamber 100, thermal element 110 may be configured to cool (i.e., lower a temperature) of blending chamber 100 and/or cosmetic liquid 330. As one example, thermal element 110 may comprise a cooling jacket that is configured to house a coolant (e.g., water, an oil, and/or a glycol). In such examples, cosmetic blending device 10 may include a coolant system including one or more of a coolant pump, piping to recirculate coolant between the pump and the cooling jacket, a cooling device (e.g., a fan), and/or a refrigerating device (e.g., compressor, evaporator, condenser, etc.). In examples where thermal element 110 is configured to both heat and cool blending chamber 100, cosmetic blending device 10 additionally may include a heater that is configured to heat the coolant. In some examples, a separate coolant circuit and coolant pump may be included for the heated coolant supply. However, in other examples, the cosmetic blending device 10 may utilize the same pump for circulating both the heated and the cooled coolant. As an example, cosmetic blending device 10 may include a three-way valve that may switch coolant flow between the heated coolant circuit and the cooled coolant circuit.

As another example, thermal element 110 may include a thermoelectric cooling device that may be configured to heat and/or cool blending chamber 100, and/or the contents contained therein (e.g., solid-shell cosmetic ingredient capsule 300, cosmetic liquid 330, and/or blending element 22), utilizing the Peltier effect. As an example, the thermal element may include two or more semiconductor materials that are configured to generate a temperature gradient across opposite ends of the semiconductor materials when a voltage is applied across the semiconductor materials (thus causing current flow there-through). The thermoelectric cooling device may be configured to both heat and cool blending chamber 100, in some examples. In particular, current may flow in a first direction to heat blending chamber 100 and/or in a second opposite direction to cool blending chamber 100. Thus, switching between heating and cooling may be achieved by reversing the direction of current flow through the device. By cooling cosmetic liquid 330, cosmetic blending device 10 may ensure that the cosmetic liquid is not too hot when presented to a user for extraction.

After the heating and/or blending, when presented to a user, cosmetic liquid 330 may have a temperature of at least 37° C., at least 38° C., at least 39° C., at least 40° C., at least 41° C., at least 42° C., at least 43° C., at least 44° C., at most 62° C., at most 61° C., at most 60° C., at most 59° C., at most 58° C., at most 56° C., at most 54° C., at most 52° C., at most 50° C., at most 49° C., and/or at most 48° C. In examples in which the thermal element is configured to optionally cool cosmetic liquid 330, such as after heating and blending the solid-shell cosmetic ingredient capsule to homogeneously mix the capsule's shell and cosmetic material to form the cosmetic liquid, the cooled cosmetic liquid may have a temperature of at least 10° C., at least 15° C., at least 20° C., at least 25° C., at least 30° C., at most 33° C., at most 30° C., at most 25° C., at most 20° C., and/or at most 15° C.

Blending element 22 may be configured to be selectively rotated and/or driven by (i.e., receive torque output from) drive mechanism 120. In particular, drive mechanism 120 may include a mechanical linkage 122 that may be configured to transmit torque output by drive mechanism 120 to blending element 22. That is, mechanical linkage 122 may mechanically couple and/or connect drive mechanism 120 and blending element 22 to transmit torque there-between. Said another way, blending element 22 may be coupled to and/or driven by drive mechanism 120 via mechanical linkage 122. Accordingly, mechanical linkage 122 may extend between blending element 22 and drive mechanism 120 and may be directly physically coupled to both blending element 22 and drive mechanism 120. Thus, in examples where drive mechanism 120 is included in base 60 and blending element 22 is included in lid 20, mechanical linkage 122 may extend from base 60 to lid 20. As discussed herein, the drive mechanism optionally may be configured, actuated, and/or powered to drive the blending element in more than one direction and/or at more than one speed. Examples of different directions include two or more of a clockwise rotational direction, a counterclockwise rotational direction, and a translational direction. Examples of different speeds include utilizing slower speeds during ramp-up periods and/or cool-down periods, utilizing higher speeds during a primary blending period, and/or utilizing oscillating speeds during any portion of the blending cycle to promote increased blending and mixing of the shell and the cosmetic material of the capsule to form cosmetic liquid 330.

Figure 5:
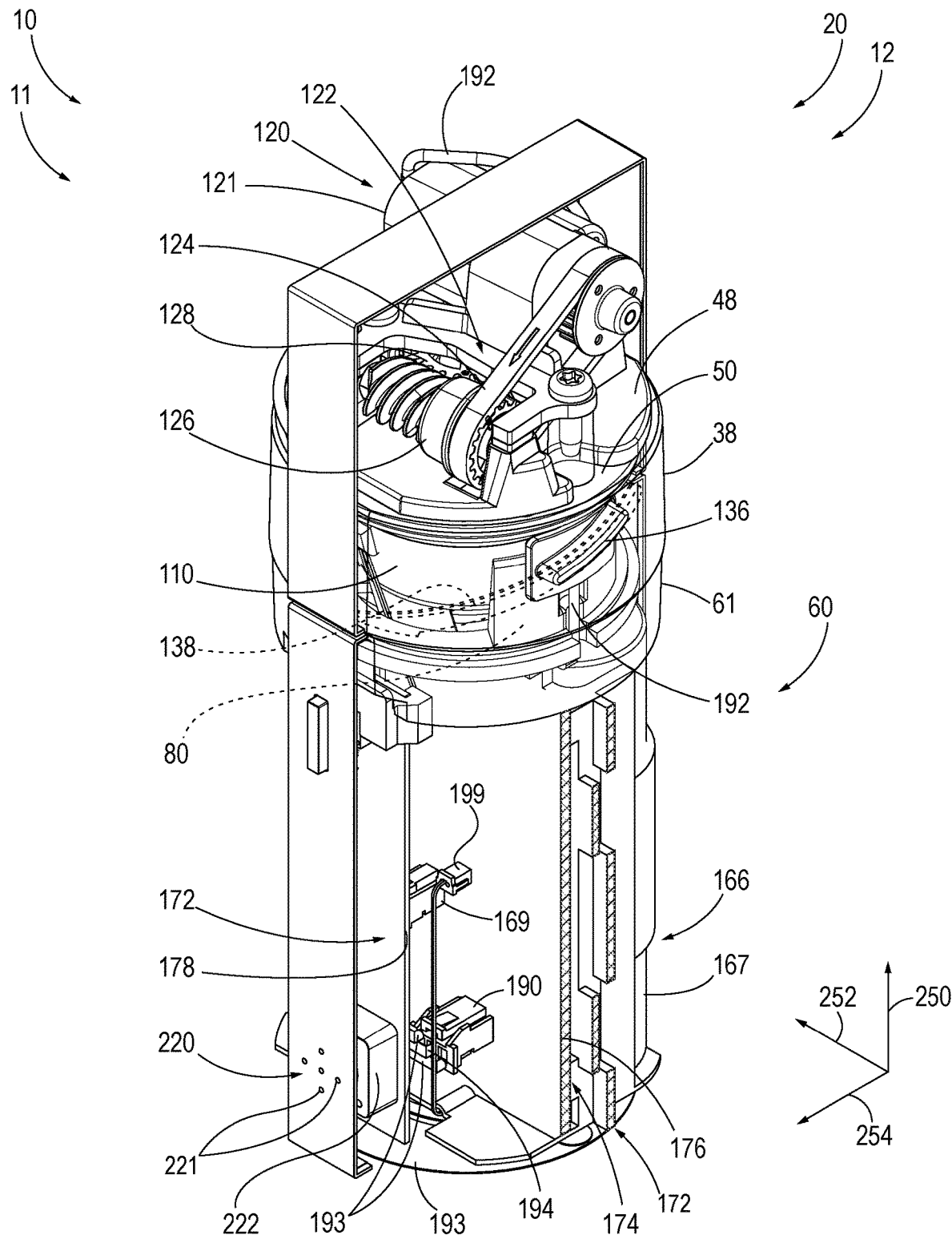
FIG. 5 is an elevated isometric internal view of the example cosmetic blending device of FIG. 2 in which a portion of the device's housing has been removed to permit illustration of internal components of the device.
Figure 6:
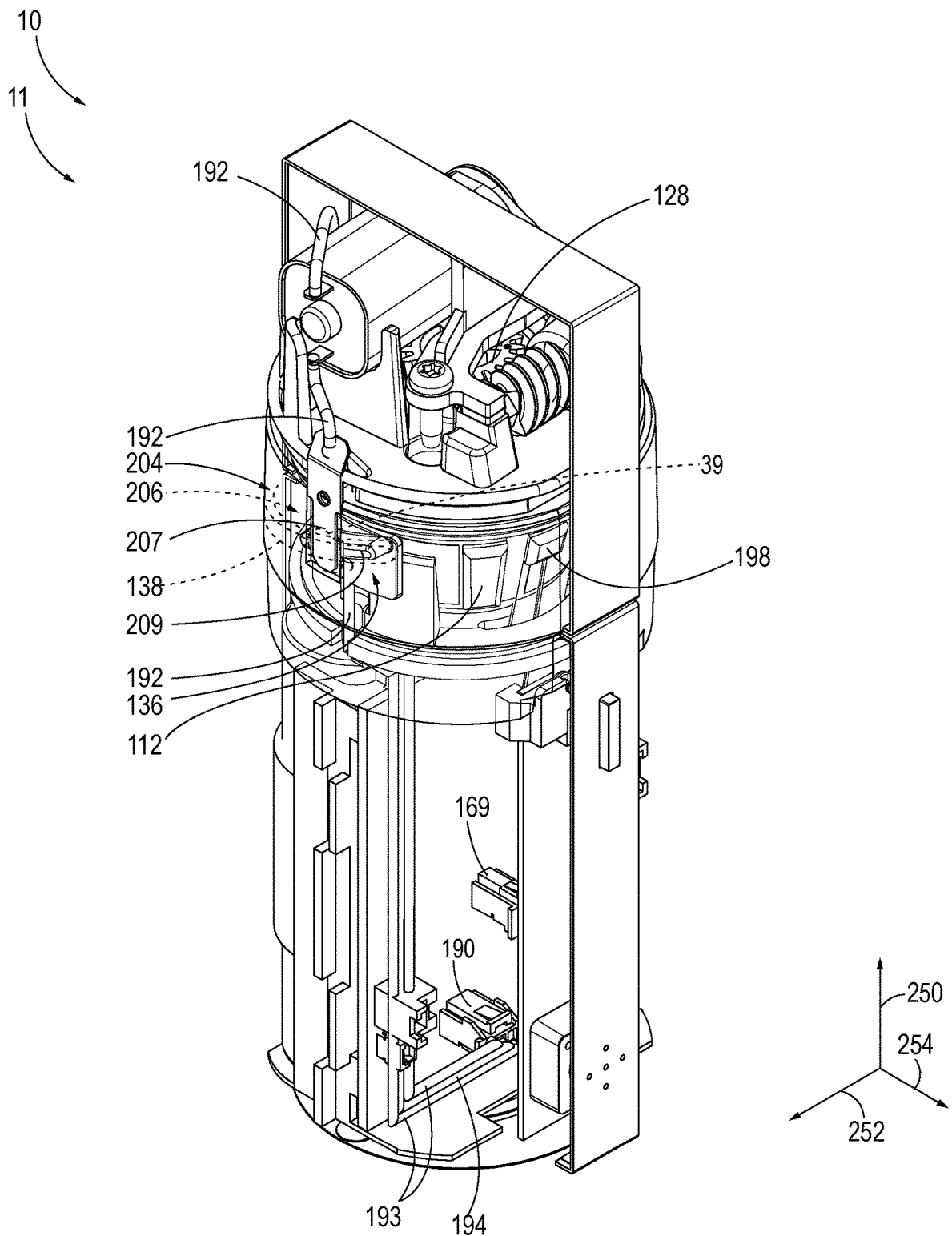
FIG. 6 is an elevated isometric internal view of the example cosmetic blending device of FIG. 2 in which a portion of the device's housing has been removed to permit illustration of internal components of the device.
Figure 7:
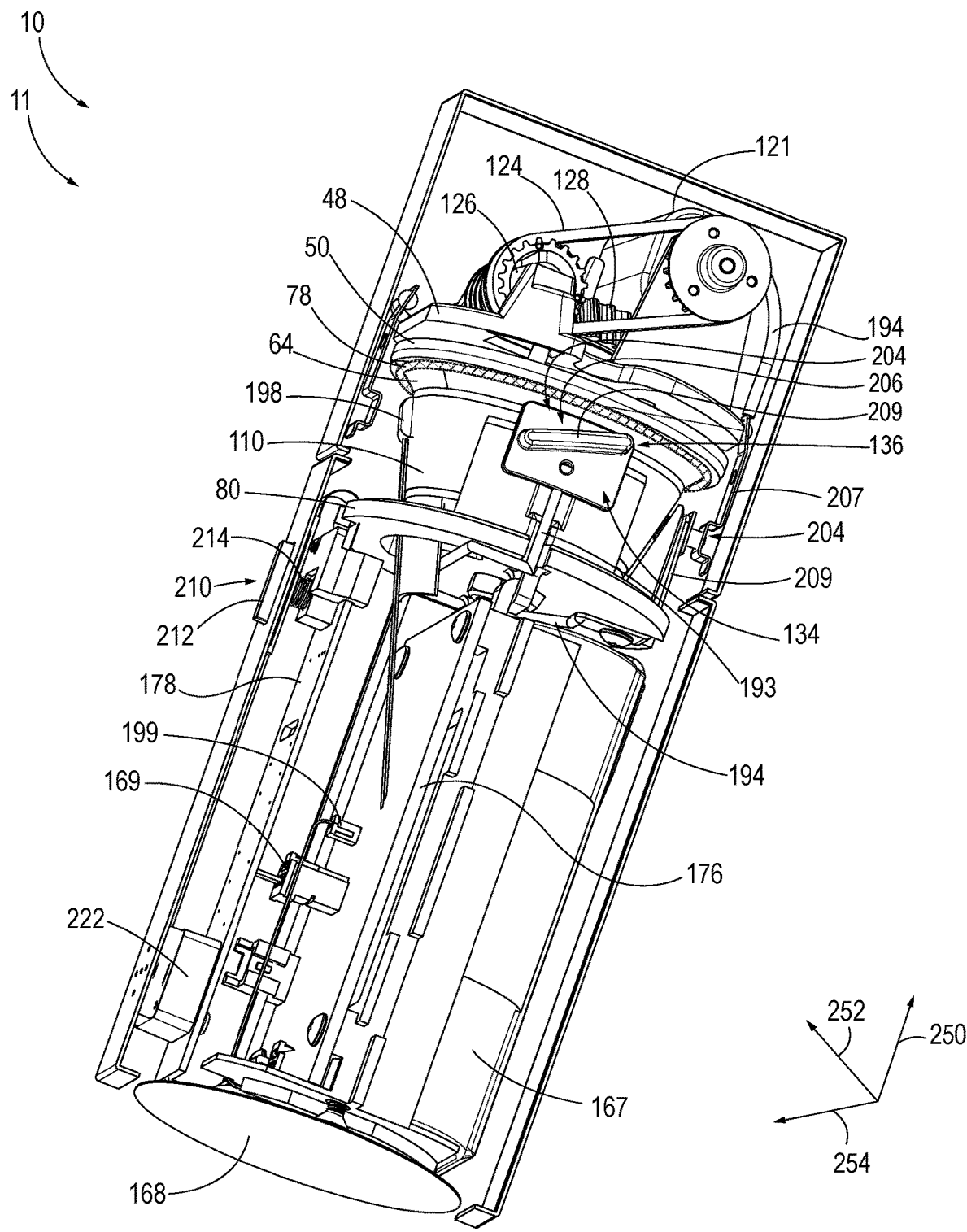
FIG. 7 is an elevated isometric internal view of the example cosmetic blending device of FIG. 2 in which a portion of the device's housing and internal components have been removed to reveal additional internal components of the device.
Figure 8:
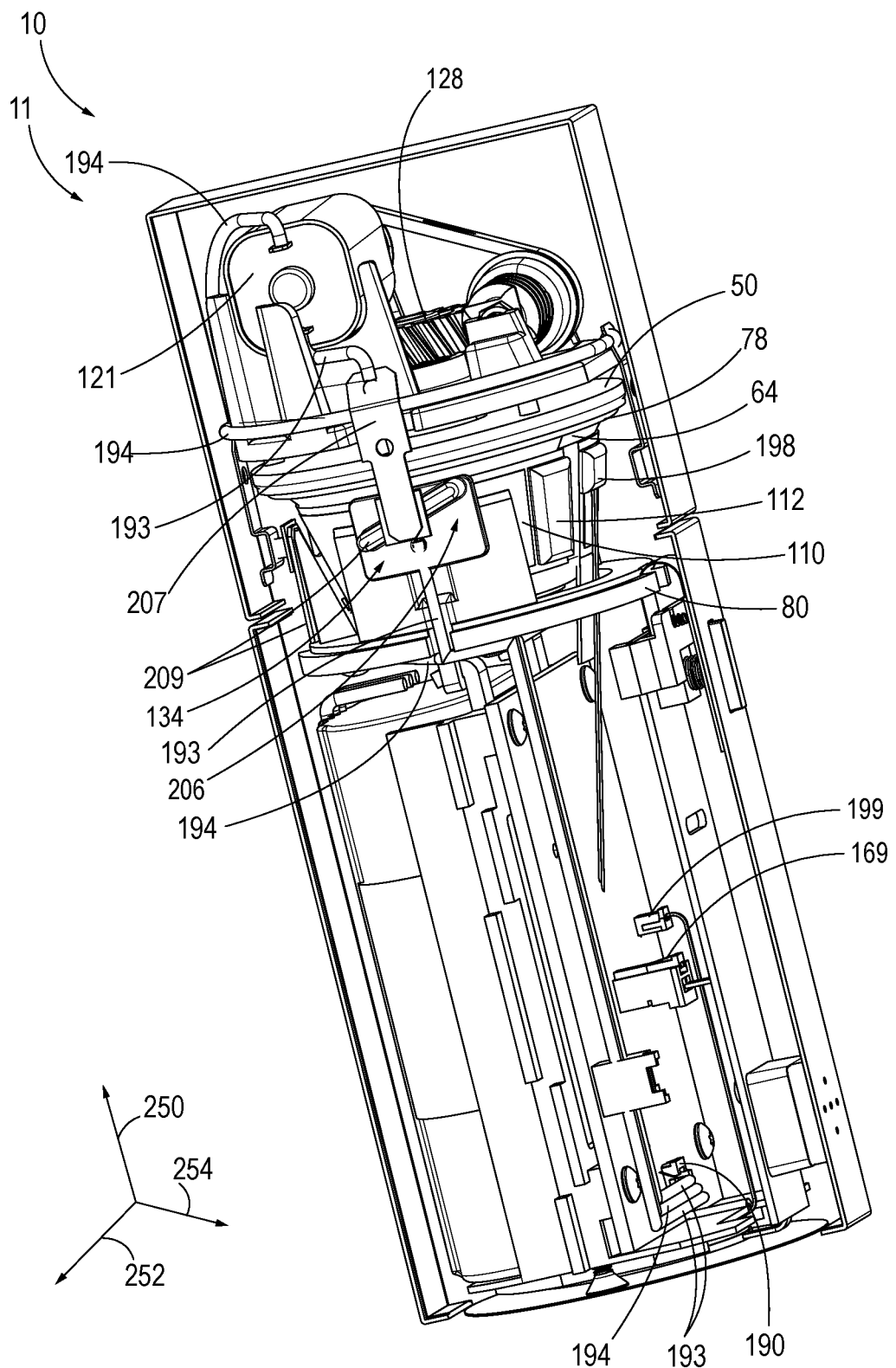
FIG. 8 is an elevated isometric internal view of the example cosmetic blending device of FIG. 2 in which a FIG. 9 is a cross-sectional view of the example cosmetic blending device of FIG. 2.

As examples, mechanical linkage 122 may include one or more of shafts, connecting rods, gears, and/or belts. As one example, mechanical linkage 122 may include a worm gear 126 and a belt 124 as best illustrated in FIGS. 5 and 7. As another example, mechanical linkage includes a planetary gear and a shaft. However, in other examples, additional gears, shafts, belts, and other mechanical coupling structures may be included depending on the orientation and/or position of the drive mechanism in the cosmetic blending device.

Blending element 22 additionally and/or alternatively may be configured to be selectively translated up and down within blending chamber 100 (e.g., repositioned along vertical axis 250) during operative use of cosmetic blending device 10. For example, translating the blending element within blending chamber 100 may change the distance between cutting edges 28 and the bottom of the blending chamber, thereby altering the degree to which the capsule and the resulting portions thereof are urged toward or away from the bottom of the blending chamber. Additionally or alternatively, translating the blending element within the blending chamber 100 may increase turbulence and/or mixing of the cosmetic liquid (and/or residual portions of capsule 300) during operative use of the cosmetic blending device to form the cosmetic liquid. Such an optional translational motion may be provided by any suitable mechanism. As an example, cosmetic blending device 10 may include a linear actuator 129 that is configured to selectively vertically translate blending element 22 up and down within blending chamber 100. As examples, linear actuator 129 may include one or more of an electric, hydraulic, and/or pneumatic linear actuator. In some examples, the linear actuator may be configured to translate only blending element 22. As one example, the linear actuator may be included within blending element 22. In such examples, shaft 24 of blending element 22 may be configured to extend and/or retract responsive to a force provided by linear actuator 129. In particular, shaft 24 may include concentric shafts that are configured to slide relative to one another to extended and retracted positions, and linear actuator 129 may be configured to adjust the concentric shafts to the extended and retracted positions to selectively translate blending element 22 up and down within blending chamber 100. As another example, linear actuator 129 may be included between mechanical linkage 122 and blending element 22 and may be configured to move the entire blending element up and down. In yet further examples, linear actuator 129 may be included within mechanical linkage 122 and/or between components of mechanical linkage 122. In yet further examples, linear actuator 129 may be configured to move both drive mechanism 120 and blending element 22. As one such example, drive mechanism 120 may be mounted on a movable plate, and linear actuator 129 may be configured to translate the movable plate up and down along vertical axis 250. In such examples, the mechanical connection between drive mechanism 120 and blending element 22 may remain constant, and thus the entire drive assembly (including mechanical linkage 122, drive mechanism 120, and blending element 22) may translate up and down together as a single unit.

As mentioned above, drive mechanism 120 may be included in lid 20 and/or base 60. Further, drive mechanism may be oriented vertically or horizontally in lid 20 and/or base 60. In particular, when mounted vertically, drive mechanism 120 may be configured such that an axis of rotation of its torque output is oriented in the vertical direction, substantially parallel to vertical axis 250. Conversely, when mounted horizontally in cosmetic blending device 10, drive mechanism 120 may be configured such that the axis of rotation of a torque output of the drive mechanism is oriented in the horizontal direction, substantially orthogonal to vertical axis 250. However, in other examples, drive mechanism 120 may be mounted in other orientations, such that the rotational axis of the torque output of the drive mechanism is angled with respect to vertical axis 250.

In some examples, cosmetic blending device 10 may be a manual device that is configured to be operated by hand. In such examples, drive mechanism 120 may include a crank handle, a wheel, and/or other manual rotary device that is configured to be rotated by a user's hand. Thus, in such examples, a user may manually turn and/or crank drive mechanism 120 to rotate blending element 22 and blend solid-shell cosmetic ingredient capsule 300.

However, in other examples, cosmetic blending device 10 may be an electrically powered device, in which at least drive mechanism 120 may be configured to be driven by electrical energy. As an example, drive mechanism 120 may include an electric motor. In such examples, drive mechanism 120 may be configured to be driven by an electric power source 160. Electric power source 160 may include an external electrical energy source 162 (e.g., a wall socket, a charging station, etc.) that is positioned outside cosmetic blending device 10 and/or an internal electrical energy source 166 (e.g., a battery) that is included within cosmetic blending device 10. Thus, cosmetic blending device 10 may be configured to be powered by external electrical energy source 162, and/or may include its own internal electrical energy source, namely, internal electrical energy source 166.

When electric power source 160 includes external electrical energy source 162, cosmetic blending device 10 may be configured to be selectively electrically connected to external electrical energy source 162 via a wired and/or wireless electrical connection. For example, cosmetic blending device 10 may include a port, a cable, a wire, and/or a cord that is/are configured to electrically connect cosmetic blending device 10 to external electrical energy source 162. External electrical energy source 162 may include a wall socket, an electrical power plug, an electrical power a socket, an external battery, a charging station, and/or an extension cord.

When electric power source 160 includes internal electrical energy source 166, internal electrical energy source 166 may be configured to store electrical energy. For example, internal electrical energy source 166 may include a battery 167. Internal electrical energy source 166 may include a single battery and/or a battery cell, although it is within the scope of the present disclosure that internal electrical energy source 166 may include multiple batteries and/or battery cells. Battery 167 may include a rechargeable battery. To charge the rechargeable battery, internal electrical energy source 166 may be configured to be selectively electrically connected (e.g., via a wired and/or wireless connection) to a charging station 164 of external electrical energy source 162. Thus in some examples, such as when cosmetic blending device 10 includes internal electrical energy source 166, external electrical energy source 162 may include charging station 164. Charging station 164 may be configured to supply electrical energy to cosmetic blending device 10 via a wired and/or wireless electrical connection with internal electrical energy source 166. Charging station 164 may in turn be electrically connected to a wall socket, an electrical power plug, an electrical power socket, and/or an external battery.

Internal electrical energy source 166 may be configured to be selectively removed from cosmetic blending device 10. For example, when internal electrical energy source 166 includes a disposable battery, the disposable battery may be configured to be selectively removed from cosmetic blending device 10 and/or replaced. As another example, when internal electrical energy source 166 includes a rechargeable battery, the rechargeable battery may be configured to be selectively removed and subsequently electrically connected to external electrical energy source 162. In such examples, the rechargeable battery may be electrically connected to the external electrical energy source 162 via a direct, wired connection.

Internal electrical energy source 166 may be included in lid 20 and/or base 60. When base 60 includes internal electrical energy source 166, internal electrical energy source 166 may be positioned below enclosed blending chamber 100. Additionally or alternatively, lid 20 may include internal electrical energy source 166. When both base 60 and lid 20 include internal electrical energy source 166, internal electrical energy source 166 may include multiple batteries that are distributed amongst lid 20 and base 60.

Distribution of electrical power from electric power source 160 may be regulated, controlled, and/or adjusted by a control system 170, also referred to as a regulator, 170. That is, cosmetic blending device 10 may include control system 170, and control system 170 may be configured to regulate, control, and/or adjust operation of actuators 118 (e.g., drive mechanism 120 and/or linear actuator 129), sensors 195, and/or other electrically powered components of cosmetic blending device 10 (e.g., thermal element 110). In particular, control system 170 may include a controller 172 that may be configured to selectively adjust operation of one or more actuators 118, sensors 195, and/or other electrically powered components of cosmetic blending device 10 by one or more of adjusting an amount of electrical power supplied to the actuators, sensors, and/or other electrically powered components of the cosmetic blending device by the electric power source, and/or by adjusting a control signal sent to dedicated (i.e., component-specific) control circuits of the actuators, sensors, and/or other electrically powered components of the cosmetic blending system.

Controller 172 may be, may be implemented as, and/or may include at least one controller 172, at least two controllers 172, at least three controllers 172, at least four controllers, at least five controllers 172, and/or at least six controllers 172. When more than one controller 172 is included, the individual controllers may be included at various positions and/or configured to regulate, direct, and/or otherwise control specific portions and/or operations of the cosmetic blending device. When a plurality of controllers 172 are utilized, the individual controllers may be referred to as subcontrollers, component-specific controllers, and/or feature controllers. Additionally or alternatively, the plurality of controller as a whole may be collectively referred to as a controller assembly. As one example, controller 172 may include a central controller 174 (e.g., a microcontroller or microprocessor) and one or more dedicated, component-specific controllers that may be configured to regulate an amount of electrical power supplied to their associated actuator, sensor, and/or other electrically powered component.

For example, controller 172 may include a motor controller 180 that may be configured to control an amount of electrical power (e.g., voltage, current, pulse width, etc.) supplied from electric power source 160 to drive mechanism 120 when drive mechanism 120 is configured as an electric motor. Motor controller 180, in turn, may be configured to determine the amount of electrical power to be supplied to the drive mechanism based on control signals received from central controller 174. Thus, central controller 174 may send command signals to the one or more dedicated, component-specific controllers (e.g., motor controller 180) that instruct the component-specific controllers as to how much electrical power to apply to their associated actuator, sensor, and/or other electrically powered component, and the dedicated, component-specific controllers may in turn adjust the amount of electrical power supplied to their associated actuator, sensor, and/or electrically powered component based on the received command signals. Stated another way, central controller 174 may indirectly adjust the amount of electrical power supplied to the actuators, sensors, and/or other electrically powered components of cosmetic blending device 10 by adjusting the command signal sent to the dedicated, component-specific controllers associated with each of these sensors, actuators, and/or other electrically powered components.

Central controller 174 additionally and/or alternatively may directly adjust an amount of electrical power supplied to one or more of the sensors, actuators and/or other electrically powered components. As one example, central controller 174 may directly adjust an amount of electrical power supplied to thermal element 110. As another example, motor controller 180 may be omitted, and central controller 174 may directly adjust an amount of electric power supplied to drive mechanism 120.

At least central controller 174, and optionally each controller 172, may include a memory unit 182 and/or a processing unit 188. Memory unit 182 may be configured to store computer-readable instructions ((e.g., the software) in non-transitory memory, and processing unit 188 may be configured to execute the stored computer-readable instructions responsive to various inputs (e.g., sensor and/or user inputs) to perform various computing functions and/or to selectively control the various electrically powered components of the cosmetic blending device.

Memory unit 182 may include non-volatile memory 184, also referred to herein as non-transitory memory 184, (e.g., ROM, PROM, and EPROM) and/or volatile memory 186, also referred to herein as transitory memory 186, (e.g., RAM, SRAM, and DRAM). Non-volatile memory 184 may be configured to store non-transitory computer-readable instructions. The computer-readable instructions may include instructions for performing one or more methods, such as methods 400 schematically represented in FIG. 14. As an example, the computer-readable instructions may comprise instructions for adjusting operation (e.g., an amount of power supplied to) of one or more of drive mechanism 120, thermal element 110, and linear actuator 129 based on one or more of user inputs, a characteristic of solid-shell cosmetic ingredient capsule 300, and/or feedback from one or more sensors.

Processing unit 188 may include integrated circuits including one or more of field-programmable gate arrays (FPGAs), application-specific integrated circuits (ASICs), digital signal processors (DSPs), microprocessors, microcontrollers, programmable array logic (PALs), and complex programmable logic devices (CPLDs).

Control system 170 may include sensors 195 that may be configured to provide feedback to controller 172. In particular, the sensors may be configured to measure a blend parameter (e.g., motor torque, electric current, blending element rotational speed, drive mechanism rotational speed, blend temperature, a weight of solid-shell cosmetic ingredient capsule 300, etc.) and provide feedback to the controller on the current (i.e., real-time) status of the heating and/or blending in the form of electrical signals. In some examples, the sensors may be configured to convert measured blend parameters (e.g., rotational speed, torque, temperature, electric, time, etc.) into electrical signals that may be communicated to controller 172. For example, the blend parameters may include a temperature of one or more of thermal element 110, blending chamber 100, solid-shell cosmetic ingredient capsule 300, and/or cosmetic liquid 330, a torque of drive mechanism 120 and/or blending element 22, a load or strain on drive mechanism 120 and/or blending element 22, a viscosity of cosmetic liquid 330, a time during which the drive mechanism and/or the blending element has been activated, and/or a rotational speed of the blending element and/or of drive mechanism 120.

As one example, control system 170 may include a temperature sensor 196 (also referred to as thermal sensor 196). Temperature sensor 196 may be configured to measure, estimate, and/or determine a temperature of thermal element 110, blending chamber 100, solid-shell cosmetic ingredient capsule 300, blending element 22, and/or cosmetic liquid 330. In particular, temperature sensor 196 may be configured to convert the measured temperature into an electrical signal that may be communicated to controller 172. Thus, temperature sensor 196 may be configured to output an electrical signal indicative of the temperature of one or more of thermal element 110, blending chamber 100, solid-shell cosmetic ingredient capsule 300, blending element 22, and/or cosmetic liquid 330. As examples, the temperature sensor 196 may comprise one or more of a thermocouple, thermistor, resistance thermometer, and/or semiconductor-based temperature sensor. As discussed in more detail herein, controller 172 may be programmed to adjust operation of thermal element 110 based on feedback from temperature sensor 196.

As another example, control system 170 may include a blending element sensor 200. Blending element sensor 200 may be configured to measure one or more operational characteristics of blending element 22. In particular, blending element sensor 200 may be configured to measure one or more of a torque generated by drive mechanism 120, a torque exerted on blending element 22 by drive mechanism 120, a torque exerted on blending element 22 by solid-shell cosmetic ingredient capsule 300 and/or cosmetic liquid 330, and/or a rotational speed of blending element 22. As one example, blending element sensor 200 may comprise a torque sensor that may be configured to measure an amount of torque applied to blending element 22. The torque sensor may be configured to measure static torque and/or dynamic torque. In particular, the torque sensor may be configured to measure one or more of a torque generated by drive mechanism 120, a torque exerted on blending element 22 by drive mechanism 120, and/or a torque exerted on blending element 22 by solid-shell cosmetic ingredient capsule 300 and/or cosmetic liquid 330. Thus, the torque sensor may be configured to output an electrical signal indicative of the torque applied to blending element 22 by, for example, drive mechanism 120 (a torque encouraging rotation of blending element 22) and/or by solid-shell cosmetic ingredient capsule 300 (i.e., a torque that resists and/or opposes rotation of blending element 22). As an example, the torque sensor may comprise one or more strain gauges.

Blending element sensor 200 additionally or alternatively may comprise a rotational speed sensor that may be configured to measure a rotational speed of blending element 22 and/or of drive mechanism 120. As one example, the rotational speed sensor may comprise a Hall effect sensor. However, the rotational speed sensor may comprise any other suitable rotational speed sensor. Thus, the rotational speed sensor may be configured to output an electrical signal indicative of the rotational speed of blending element 22 and/or of drive mechanism 120. As discussed, controller 172 may be programmed to adjust operation of drive mechanism 120 based on feedback from the blending element sensor 200.

Sensors 195 additionally or alternatively may include an identification sensor 202 that may be configured to identify a characteristic of solid-shell cosmetic ingredient capsule 300. The characteristic may be an identity characteristic and/or a physical characteristic of the solid-shell cosmetic ingredient capsule. As examples, the identity characteristic of solid-shell cosmetic ingredient capsule 300 may include one or more of a name, type, serial number, or other identifying parameter of the solid-shell cosmetic ingredient capsule. The physical characteristics of solid-shell cosmetic ingredient capsule 300 may include one or more of a weight, volume, hardness, compressive strength, crush resistance, and/or melting point of solid-shell cosmetic ingredient capsule 300. In some examples, the identity characteristic may identify, correspond to, and/or otherwise indicate one or more of the physical characteristics of solid-shell cosmetic ingredient capsule 300. For example, the type of the solid-shell cosmetic ingredient capsule may indicate or otherwise correspond to an intended body surface to which the cosmetic liquid is to be applied (e.g., skin, hair, or nails), an intended effect of the solid-shell cosmetic ingredient capsule (e.g., moisturizing, soothing, exfoliating, etc.), dosage, and/or ingredient type. As discussed in more detail herein, controller 172 may be programmed to set initial blend parameters based on feedback from the temperature sensor.

Additionally or alternatively, control system 170, and in particular, controller 172, may be programmed to calculate, infer, and/or otherwise estimate one or more of the blend parameters based on electrical properties (e.g., current flow, voltage, internal resistance) of one or more of the electrical components of cosmetic blending device 10. As an example, controller 172 may calculate, infer, and/or otherwise estimate the rotational speed of drive mechanism 120 and/or blending element 22 based on current flow between drive mechanism 120 and electric power source 160. As one such example, controller 172 may include an electric circuit configured to measure current flow between drive mechanism 120 and electric power source 160. Based on the measured current flow, controller 172 may infer the rotational speed of drive mechanism 120 based on the back electromotive force (back-EMF) since the back-EMF may be directly proportional to the rotational speed of the drive mechanism. In particular, the rotational speed may be related to the back-EMF based on a known back-EMF constant, $K_e$ (i.e., $\omega_{motor} = V_{B-EMF}/K_e$). The back-EMF may be calculated based on a difference between the measured current flow and an expected current flow (i.e., $V_{B-EMF} = R_{Drive\ Mechanism} \cdot (I_{Expected} - I_{Measured})$), where the expected current flow may be calculated using Ohm's law based on the voltage applied to the drive mechanism by controller 172 and/or electric power source 160 and a known internal resistance of the drive mechanism (i.e., $I_{Expected} = V_{Applied}/R_{Drive\ Mechanism} \rightarrow V_{B-EMF} = V_{Applied} - (R_{Drive\ Mechanism} \times I_{Measured})$).

Each type of solid-shell cosmetic ingredient capsule 300 may include a set of physical characteristics which may or may not be unique, and each capsule's set of physical characteristics may be tied, linked, associated with, and/or otherwise correlated to a unique identity characteristic. That is, physical characteristics of solid-shell cosmetic ingredient capsule 300 may be categorized based on the identity characteristic of the solid-shell cosmetic ingredient capsule. In this way, the controller may identify the physical characteristics of solid-shell cosmetic ingredient capsule 300 based on the identity characteristic.

Controller 172 may be in electrical communication (e.g., via a wired connection and/or wireless connection) with the actuators, sensors, and/or other electrically powered components of the cosmetic blending device to adjust operation thereof and/or receive feedback therefrom, as discussed in greater detail herein. For example, controller 172 may be electrically connected to one or more of drive mechanism 120, linear actuator 129, thermal element 110, temperature sensor 196, blending element sensor 200 and/or identification sensor 202 via wiring 192.

Thus, electrically powered components of cosmetic blending device 10 may be electrically connected to controller 172 and/or electric power source 160. Controller 172 may be configured to adjust operation of the actuators (e.g., drive mechanism 120 and/or linear actuator 129) based on feedback from the one or more sensors and/or user input.

In particular, controller 172 may set and/or determine threshold blend parameters based on user input and/or based on characteristics of solid-shell cosmetic ingredient capsule 300. Threshold blend parameters may include one or more of a threshold temperature (e.g., threshold temperature of thermal element 110, threshold temperature of blending chamber 100, threshold temperature of solid-shell cosmetic ingredient capsule 300, and/or threshold temperature of cosmetic liquid 330), a threshold torque (e.g., a threshold torque output by drive mechanism 120, a threshold torque exerted on blending element 22 by drive mechanism 120, and/or a threshold torque exerted on drive mechanism 120 by solid-shell cosmetic ingredient capsule 300 and/or cosmetic liquid 330), a threshold rotational speed of drive mechanism 120, a threshold rotational speed of blending element 22, a threshold height of blending element 22 (i.e., a distance between blending element 22 and bottom 66 of bowl-shaped depression 64), a threshold heating duration, and/or a threshold blending duration. The aforementioned thresholds may be minimums, maximums and/or ranges of values for the associated parameters. For example, the threshold temperature may be a minimum temperature, a maximum temperature and/or a range of temperatures.

As one example, the threshold blend parameters may be directly set, or selected, by a user. In particular, cosmetic blending device 10 may include a user input device 210 that may be configured to allow a user to manually and/or explicitly set the threshold blend parameters. For example, a user may input a desired cosmetic liquid temperature, desired blending speed, desired blending temperature, one or more additional ingredients that a user desires to include in blending chamber 100, and/or a desired blending duration. User input device 210 may include one or more of a button, touch screen, joystick, keyboard, and/or other type of user input device that may be configured to receive user input.

Additionally or alternatively, controller 172 may set and/or determine the threshold blend parameters based on one or more characteristics (i.e., physical characteristics and/or identity characteristics) of solid-shell cosmetic ingredient capsule 300. The characteristics may be input by the user via user input device 210 and/or may be determined by the controller based on output from the various sensors, such as from identification sensor 202. Thus, the controller 172 may determine the identity characteristics of solid-shell cosmetic ingredient capsule 300 based on user input. Additionally or alternatively, controller 172 may determine the identity characteristics of solid-shell cosmetic ingredient capsule 300 based on feedback from identification sensor 202.

For example, identification sensor 202 may be configured to identify a unique identifier of solid-shell cosmetic ingredient capsule 300. In particular, the unique identifier may be configured to provide an indication of the identity characteristics of the solid-shell cosmetic ingredient capsule (e.g., name, serial number, type, etc.). As examples, the unique identifier may comprise a QR code, barcode, RFID tag, image, and/or any other identifying letter, number, or indicia that may be recognized and/or read by cosmetic blending device 10. Thus, in some such examples, identification sensor 202 may include a barcode reader, RFID scanner, and/or other type of reader, scanner, or optical sensor. Based on the identity characteristics of the solid-shell cosmetic ingredient capsule 300 identified via the unique identifier, controller 172 may be programmed to determine one or more physical characteristics of solid-shell cosmetic ingredient capsule 300, such as its weight, hardness, volume, etc. In particular, controller 172 may include a look-up table or other indexing structure stored in non-transitory memory 184 that may associate each unique identifier and/or identity characteristics with known physical characteristics of the identified solid-shell cosmetic ingredient capsule.

Based on the identity characteristics and/or associated physical characteristics of the identified solid-shell cosmetic ingredient capsule 300, the controller 172 may set the threshold blend parameters. In this way, user input device 210 may be configured to permit a user to input one or more of the characteristics of solid-shell cosmetic ingredient capsule 300. Additionally or alternatively, the controller may be configured to determine the physical characteristics of the solid-shell cosmetic ingredient capsule based on the identity characteristics of the solid-shell cosmetic ingredient capsule, which may be determined based on feedback from identification sensor 202.

Controller 172 additionally or alternatively may be configured to determine the identity characteristics of solid-shell cosmetic ingredient capsule 300 and/or physical characteristics of solid-shell cosmetic ingredient capsule 300 based on a measured physical characteristic of solid-shell cosmetic ingredient capsule 300. In such examples, identification sensor 202 may be configured to measure a physical characteristic of solid-shell cosmetic ingredient capsule 300 (such as a weight of the solid-shell cosmetic ingredient capsule). As an example, identification sensor 202 may comprise a weight sensor (e.g., digital scale), and the controller may be programmed to set threshold blend parameters based on an indication of the weight of solid-shell cosmetic ingredient capsule 300 obtained from identification sensor 202. Controller 172 additionally or alternatively may determine one or more identity characteristics of solid-shell cosmetic ingredient capsule 300 and/or other physical characteristics of the solid-shell cosmetic ingredient capsule based on the measured weight, and may adjust and/or set threshold blending parameters accordingly.

Based on one or more of the characteristics of the solid-shell cosmetic ingredient capsule, the controller 172 may set and/or determine the threshold blend parameters (e.g., the threshold temperature for thermal element 110, blending chamber 100, and/or solid-shell cosmetic ingredient capsule 300, the threshold torque for blending element 22, the threshold rotational speed for drive mechanism 120, the threshold rotational speed for blending element 22, and/or the threshold height for blending element 22). As one example, the controller 172 may adjust blending element 22 to a lower position (closer to bottom 66 of bowl-shaped depression 64) for solid-shell cosmetic ingredient capsules 300 having smaller volumes. As another example, controller 172 may set the desired torque and/or rotational speed to higher values for denser and/or harder solid-shell cosmetic ingredient capsules 300. As yet another example, controller 172 may set the desired temperature to a higher value for solid-shell cosmetic ingredient capsules 300 having a higher melting temperature. Thus, controller 172 may set the threshold blend parameters based on or more of the volume, hardness and/or strength, composition, and/or melting temperature of the solid-shell cosmetic ingredient capsule. These physical characteristics of the solid-shell cosmetic ingredient capsule may in turn be determined based on the identity characteristic of the solid-shell cosmetic ingredient capsule, as discussed above.

Thus, controller 172 may be programmed to set the threshold blend parameters, based on a measured physical characteristic of solid-shell cosmetic ingredient capsule 300, based on the identity characteristic of solid-shell cosmetic ingredient capsule 300, and/or based on user-selected preferences. In particular, controller 172 may determine one or more of the physical characteristics by direct measurement (e.g., via a scale), and/or inferentially based on the one or more identity characteristics (e.g., via identification of the unique identifier). Additionally or alternatively, the threshold blend parameters may be adjusted during a blending cycle. As an example, the threshold rotational speed of drive mechanism 120 and/or blending element 22 may be adjusted during a blending cycle to operate the drive mechanism 120 at different speeds throughout a blending cycle. Further additionally or alternatively, controller 172 may be configured to receive user inputs that select one or more threshold blend parameters.

However, in other examples, one, more than one, or even all of the threshold blend parameters may be pre-set. That is, they may be approximately the same for every solid-shell cosmetic ingredient capsule 300, and controller 172 may not adjust the threshold blend parameters depending on the characteristics of the solid-shell cosmetic ingredient capsule.

Controller 172 additionally or alternatively may programmed to control operation of one or more of the electrically powered components of cosmetic blending device 10 (e.g., thermal element 110, drive mechanism 120, and/or linear actuator 129) during the heating and/or blending, based on feedback from the one or more the sensors. Thus, control system 170 may actively adjust operation of the various electrically powered actuators in a closed-loop feedback control scheme, such as proportional-integral (PI) control or proportional-integral-derivative (PID) control, to more accurately maintain the actual blending parameters at the corresponding thresholds.

For example, controller 172 may adjust operation of thermal element 110 based on feedback from temperature sensor 196, and in particular, based on a difference between a measured temperature (temperature measured by temperature sensor 196) and the threshold temperature. In such examples, controller 172 may increase an amount of heat output by thermal element 110 when the measured temperature is less than the threshold temperature and may decrease an amount of heat output by thermal element 110 when a measured temperature is greater than the threshold temperature. The threshold temperature may be at least 27° C., at least 28° C., at least 29° C., at least 30° C., at least 31° C., at least 32.2° C., at least 33° C., at least 34° C., at least 35° C., at least 36° C., at least 37° C., at least 38° C., at most 62° C., at most 61° C., at most 60° C., at most 59° C., at most 58° C., at most 56° C., at most 54° C., at most 52° C., at most 50° C., at most 49° C., and/or at most 48° C. Additionally or alternatively, temperature sensor 196 and/or controller 172 may include a protection circuit that automatically and/or passively reduces an amount of electrical power (and in some examples, completely cuts off the electrical power) supplied to thermal element 110 when the temperature of thermal element 110 increases above an upper threshold temperature.

As another example, controller 172 may adjust operation of drive mechanism 120 based on feedback from blending element sensor 200, and in particular based on a difference between a measured rotational speed and/or a measured torque of blending element 22 (rotational speed and/or torque measured by blending element sensor 200) and the threshold rotational speed and/or the threshold torque. In particular, controller 172 may adjust a torque output by drive mechanism 120 and/or increase a rotational speed of blending element 22 and/or of drive mechanism 120 (e.g., by increasing an amount of power supplied to drive mechanism 120), when one or more of: a measured static torque (i.e., a reaction torque) is greater than a threshold static torque, a measured dynamic torque is less than a threshold dynamic torque, and/or a measured, calculated, and/or inferred rotational speed is less than a threshold rotational speed. Conversely, controller 172 may decrease the torque output by drive mechanism 120 and/or decrease the rotational speed of blending element 22 when the measured static torque is less than the threshold static torque, the measured dynamic torque is greater than the threshold dynamic torque, and/or the measured rotational speed is greater than the threshold rotational speed. The threshold static torque and/or the threshold dynamic torque may be at least, at least 0.05 Newton-centimeters (N·cm), at least 0.1 N·cm, at least 0.2 N·cm, at least 0.3 N·cm, at least 0.4 N·cm, at least 0.5 N·cm, at least 0.6 N·cm, at least 0.7 N·cm, at least 0.8 N·cm, at least 0.9 N·cm, at least 1 N·cm, at least 2 N·cm, at least 3 N·cm, at most 50 N·cm, at most 40 N·cm, at most 30 N·cm, at most 20 N·cm, at most 10 N·cm, at most 7.5 N·cm, at most 5 N·cm, at most 4 N·cm, at most 3 N·cm, at most 2 N·cm, and/or at most 1 N·cm.

The threshold rotational speed may be a threshold rotational speed of drive mechanism 120 and/or of blending element 22. The rotational speed of blending element 22 may be inferred from a rotational speed of drive mechanism 120, and vice versa, based on a gear ratio of mechanical linkage 122. That is, the gear ratio of mechanical linkage 122 may cause blending element 22 to spin at a different angular rotational speed than drive mechanism 120, and this difference in angular rotational speed may be calculated based on the known gear ratio of mechanical linkage 122. As examples, the threshold rotational speed may be at least 300 revolutions per minute (RPM), at least 350 RPM, at least 400 RPM, at least 450 RPM, at least 500 RPM, at most 1500 RPM, at most 1400 RPM, at most 1300 RPM, at most 1250 RPM, at most 1200 RPM, at most 1150 RPM, at most 1100 RPM, at most 1050 RPM, at most 1000 RPM, at most 950 RPM, at most 900 RPM, at most 800 RPM, and/or at most 750 RPM. In some examples, rotational speed may be directly measured by blending element sensor 200. Blending element sensor 200 may be configured to measure a rotational speed of drive mechanism 120 and/or of blending element 22. However, as described above, in other examples, the rotational speed of the drive mechanism may be inferred based on a measured current flow between drive mechanism 120 and electric power source 160.

As yet another example, controller 172 may adjust a height of blending element 22 based on feedback from blending element sensor 200. In particular, when the measured torque and/or measured rotational speed is less than desired, controller 172 may command linear actuator 129 to move blending element 22 up and down to facilitate better blending of solid-shell cosmetic ingredient capsule 300. Stated another way, the linear actuator 129 may repeatedly reciprocate blending element 22 up and down to facilitate more even blending of solid-shell cosmetic ingredient capsule 300. In other examples, linear actuator 129 may adjust the height of blending element 22 (the distance between blending element 22 and bottom 66 of bowl-shaped depression 64) at the beginning of the blending cycle (e.g., prior to spinning blending element 22 with drive mechanism 120) to one or more of ensure that blending element 22 crushes the solid-shell cosmetic ingredient capsule, to ensure that blending element 22 actually makes contact with solid-shell cosmetic ingredient capsule 300, and/or to encourage more contact between blending element 22 and solid-shell cosmetic ingredient capsule 300. In some such examples, the controller may command linear actuator 129 to adjust the height of blending element 22 at the beginning of the blending cycle only, and after the adjusting, may maintain the blending element at the same height for the remainder of the blending cycle.

Additionally or alternatively, controller 172 may adjust the height of the blending element based on the one or more identity characteristics and/or based on the one or more physical characteristics of the solid-shell cosmetic ingredient capsule. As an example, controller 172 may adjust the height of blending element 22 based on a height and/or volume of the solid-shell cosmetic ingredient capsule. Specifically, the controller may command linear actuator 129 to lower blending element 22 closer to bottom 66 of bowl-shaped depression 64 for smaller and/or shorter solid-shell cosmetic ingredient capsules 300 than for larger and/or taller solid-shell cosmetic ingredient capsules 300. By adjusting the height of the blending element based on the size, volume, and/or height of the solid-shell cosmetic ingredient capsule, the controller may ensure that blending element 22 crushes the solid-shell cosmetic ingredient capsule when the cosmetic blending device is adjusted to the closed position. Additionally or alternatively, the controller may ensure that the blending element makes contact with, and thereby blends, the solid-shell cosmetic ingredient capsule. In this way, controller 172 and actuator 129 may ensure more even and complete blending of the solid-shell cosmetic ingredient capsule, thereby providing a more homogenous cosmetic liquid 330.

As introduced above, controller 172 may adjust one or more of the blend parameters during a blending cycle. As an example, the rotational speed of drive mechanism 120 may be adjusted during a blending cycle to spin drive mechanism 120 at different speeds during the blending cycle. In such an example, the threshold rotational speed may be set lower and/or to zero (i.e., drive mechanism 120 powered off) during a first portion of a blending cycle, may be ramped up (e.g., linearly, non-linearly, in a step-wise manner, etc.) to a maximum threshold rotational speed during a second portion of a blending cycle, and/or may be operated at the maximum rotational speed during a third portion of a blending cycle. In some examples, the first portion of the blending cycle may comprise a time period (e.g., the first 4, 5, 6, 7, 8, 9, 10, etc., seconds of a blending cycle), may be based on one or more sensed parameters (e.g., a measured temperature), and/or may be based on a state of solid-shell cosmetic ingredient capsule 300. As an example, the drive mechanism 120 may not be powered on until the measured temperature reaches the threshold temperature (e.g., at least the melting temperature of solid-shell cosmetic ingredient capsule 300) and/or until solid-shell cosmetic ingredient capsule 300 has at least partially melted and/or otherwise softened. Thus, in some such examples, the solid-shell cosmetic ingredient capsule initially may be heated by thermal element 110 until it is soft and/or at least partially melted before the blending (via blending element 22) is initiated.

Pre-heating the solid-shell cosmetic ingredient capsule prior to powering on the drive mechanism may enhance the blending and result in a more homogenous cosmetic liquid. This is because softening and/or melting the solid-shell cosmetic ingredient capsule prior to blending may reduce undesirable splattering of the solid-shell cosmetic ingredient capsule. In particular, pieces of the solid-shell cosmetic ingredient capsule may be flung around blending chamber 100 and/or become lodged in blending element 22 (e.g., in-between cutting edges 28) when the drive mechanism 120 is powered on before the solid-shell cosmetic ingredient capsule is sufficiently soft and/or melted.

Additionally or alternatively, controller 172 may be programmed to pulse and/or otherwise repetitively adjust one or more of the rotational speed and/or rotational direction of drive mechanism 120. More abrupt changes in rotational speed and/or direction (e.g., by way of pulsing) may mitigate and/or prevent the buildup of chunks of solid-shell cosmetic ingredient capsule 300 in and/or on blending element 22, and/or may dislodge chunks that have already built up on blending element 22, thereby facilitating more even and complete blending of solid-shell cosmetic ingredient capsule 300.

As another example, the threshold temperature may be adjusted during a blending cycle. For example, when the threshold temperature during the blending is hotter than a user-friendly temperature (e.g., hotter than 48.9° C., 55° C., and/or 60° C.), the threshold temperature may lowered to the user-friendly temperature (e.g., 38° C., 40° C., 42° C., 44° C., 46° C., 48° C. and/or 49° C.) once solid-shell cosmetic ingredient capsule 300 has been fully converted to cosmetic liquid 330, thus allowing the cosmetic liquid to cool to the user-friendly temperature before terminating the heat and blending cycle and allowing a user to extract the cosmetic liquid. This may increase user safety and/or reduce user discomfort when applying cosmetic liquid 330. Controller 172 additionally or alternatively may be configured to prevent opening of the blending chamber (i.e., movement of lid 20 away from base 60) when the temperature of the cosmetic liquid is above a threshold temperature, thereby preventing a user from touching a cosmetic liquid that exceeds such a threshold temperature. For example, cosmetic blending device 10 may include a computer-controlled coupling structure 130 that is configured to restrict (mechanically, magnetically, electromechanically, etc.) movement of the lid away from the base if the temperature of the cosmetic liquid and/or portion of blending chamber 100 exceeds a threshold temperature.

By including sensors configured to measure the blend parameters and/or by otherwise measuring various operating parameters (e.g., current flow between drive mechanism 120 and electric power source 160), and by including a controller that employs closed-loop feedback control, blending device 10 may more accurately control the blending parameters, thereby ensuring more homogenous and even mixing of solid-shell cosmetic ingredient capsule 300.

In some examples, when the electrically connected components of the cosmetic blending device are positioned in discrete parts of the cosmetic device (e.g., where one component is included in lid 20 and another is included in base 60), cosmetic blending device 10 may include a power transmitting structure 204 that is configured to transmit electrical power between base 60 and lid 20. As one example, electric power source 160 may be included in base 60, and drive mechanism 120 may be included in lid 20. As another example, controller 172 may be included in base 60, and drive mechanism 120 may be included in lid 20. As yet another example, thermal element 110 may be included in lid 20 and controller 172 and/or electric power source 160 may be included in base 60. In a still further example, thermal element 110 may be included in base 60 and controller 172 and/or electric power source 160 may be included in lid 20.

Regardless of which components are included in lid 20 and base 60, power transmitting structure 204 may include an interlock 206 that may be configured to transmit power between base 60 and lid 20 when base 60 and lid 20 are in the closed position. In some examples, power transmitting structure 204 may be configured to only permit power to be transmitted between base 60 and lid 20 when base 60 and lid 20 are in the closed position. That is, interlock 206 may prevent power transmitting structure 204 from transmitting electrical power between base 60 and lid 20 when base 60 and lid 20 are not in closed position. Thus, in examples where electric power source 160 is positioned in base 60 and drive mechanism is positioned in lid 20, power transmitting structure 204 may be configured to permit electrical power to be transmitted from electric power source 160 in base 60 to drive mechanism 120 in lid 20 by providing an electrical connect between base 60 and lid 20.

Interlock 206 may include any suitable electrically conductive structures in base 60 and lid 20 that may be configured to come in contact, or at least operatively close proximity to one another, when base 60 and lid 20 are in the closed position to provide a physical pathway for electric current to flow between base 60 and lid 20. As one example, interlock 206 may include a pair of mating electrical contacts. In particular, the interlock 206 may include a first electrical contact 207 that may be included in lid 20, and a second electrical contact 209 that may be included in base 60. First electrical contact 207 and second electrical contact 209 may physically touch one another and/or be in close enough proximity to another to conduct electric current there-between when lid 20 and base 60 are in the closed position. Interlock 206 may be constructed from an electrically conductive material, such as one or more metals and/or metal alloys.

Power transmitting structure 204 additionally or alternatively may be included in and/or coupled to coupling structure 130. Specifically, in some examples, interlock 206 may be included in releasable locking structure 134. As one such example, when releasable locking structure 134 includes threads, the interlock may be coupled to, and/or included in the threads. That is, the threads themselves may include and/or may be constructed from an electrically conductive material that may transmit electricity between the lid and the base when the base and lid are in the closed position. The base and/or lid optionally may be include a compressible gasket or other resilient member that is compressed when the lid is fully threaded on the base, with such gasket or other resilient member urging the threads to remain in electrical contact during operative use of cosmetic blending device 10 to produce cosmetic liquid 330. Seal 78 optionally may be or include such a compressible gasket or other resilient member.

FIGS. 2-10 illustrate a less schematic example of a cosmetic blending device 10 according to the present disclosure. The example device of FIGS. 2-10 may be referred to herein as example cosmetic blending device 11. It is within the scope of the present disclosure that example cosmetic blending device 11 additionally or alternatively may include any of the features, structures, components, variants, and the like that are described and/or illustrated in connection with the cosmetic blending devices 10 of FIG. 1. Similarly the cosmetic blending devices 10 illustrated and/or described in connection with FIG. 1 additionally or alternatively may include any of the features, structures, components, variants, and the like that are described and/or illustrated in connection with example cosmetic blending device 11 of FIGS. 2-10.

Figure 2:
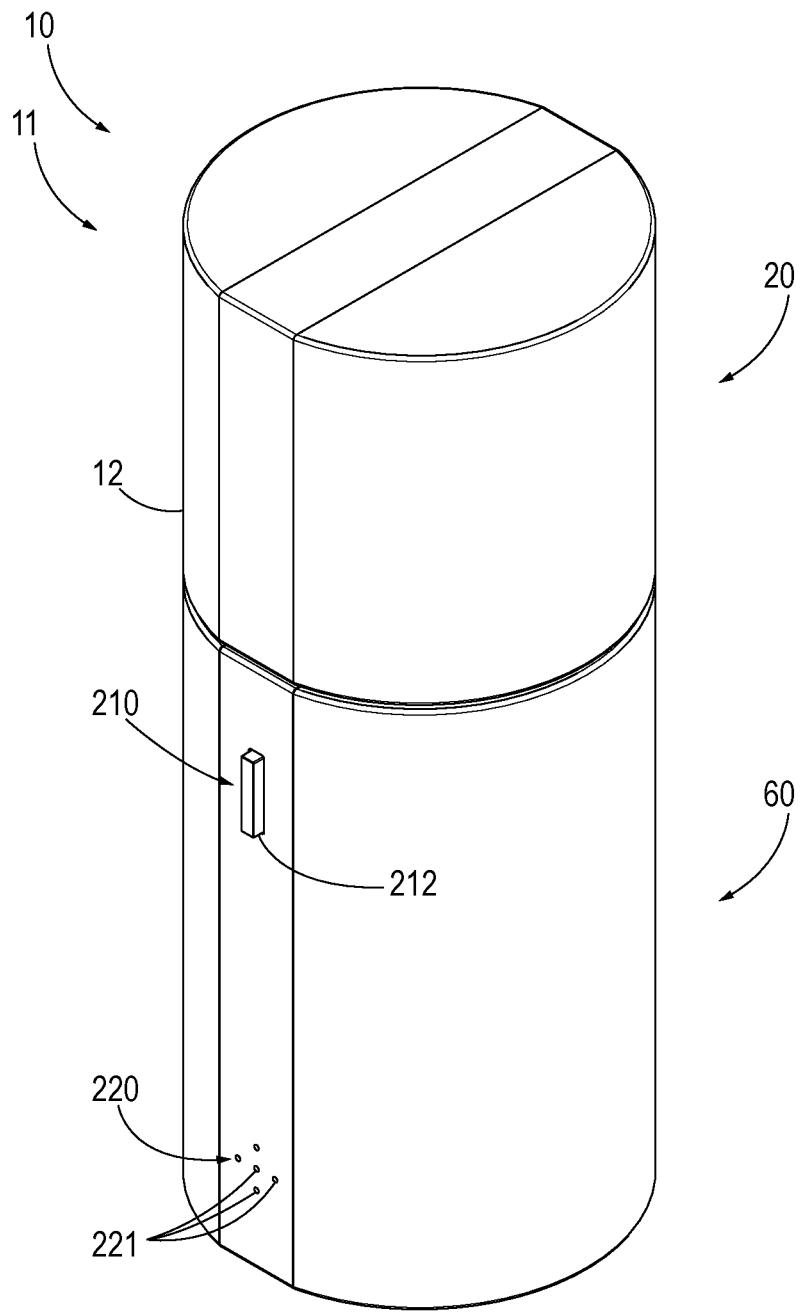
FIG. 2 is an external view of an example cosmetic blending device of the cosmetic blending devices of FIG. 1 in a closed position.
Figure 9:
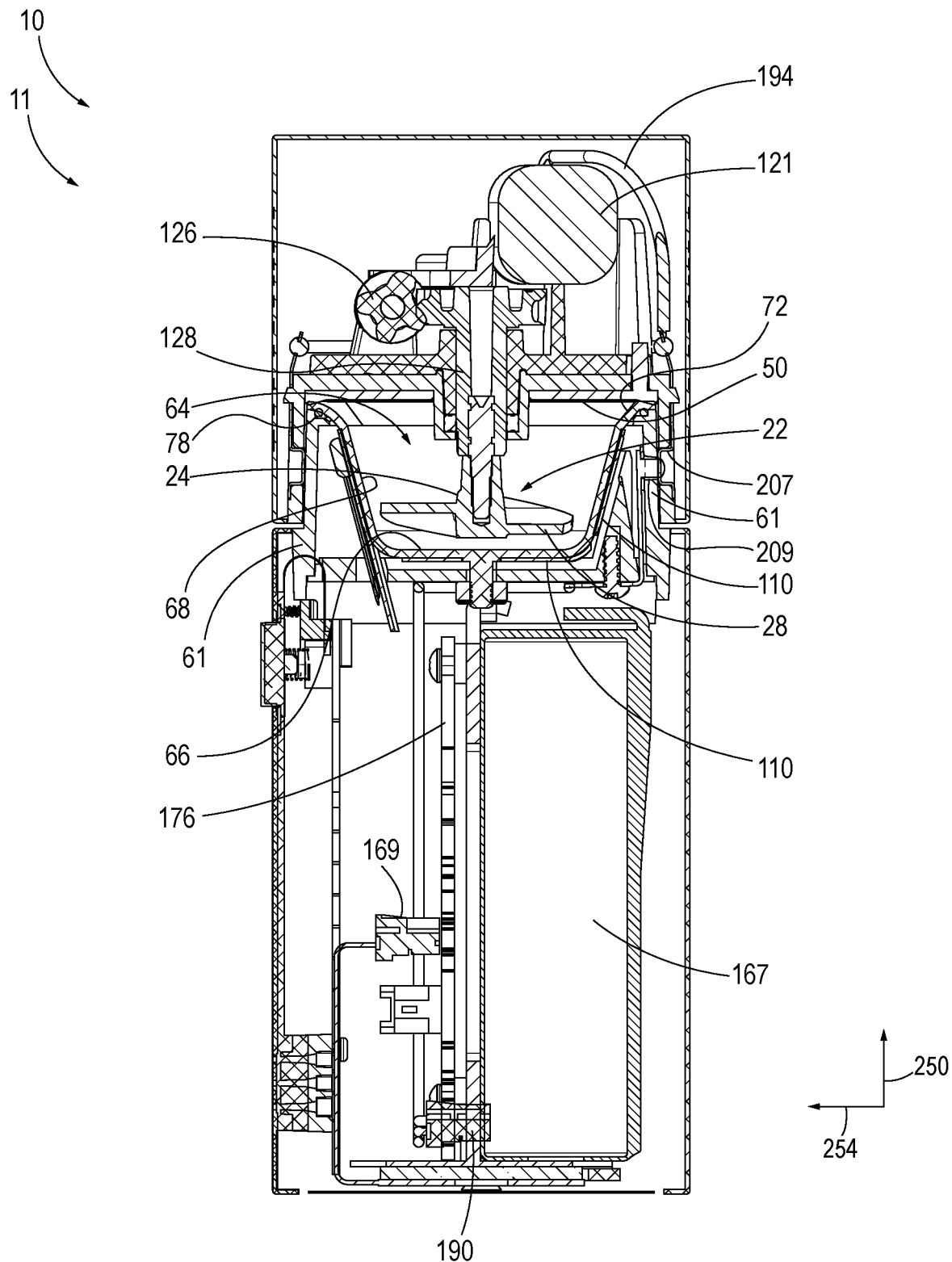
Figure 10:
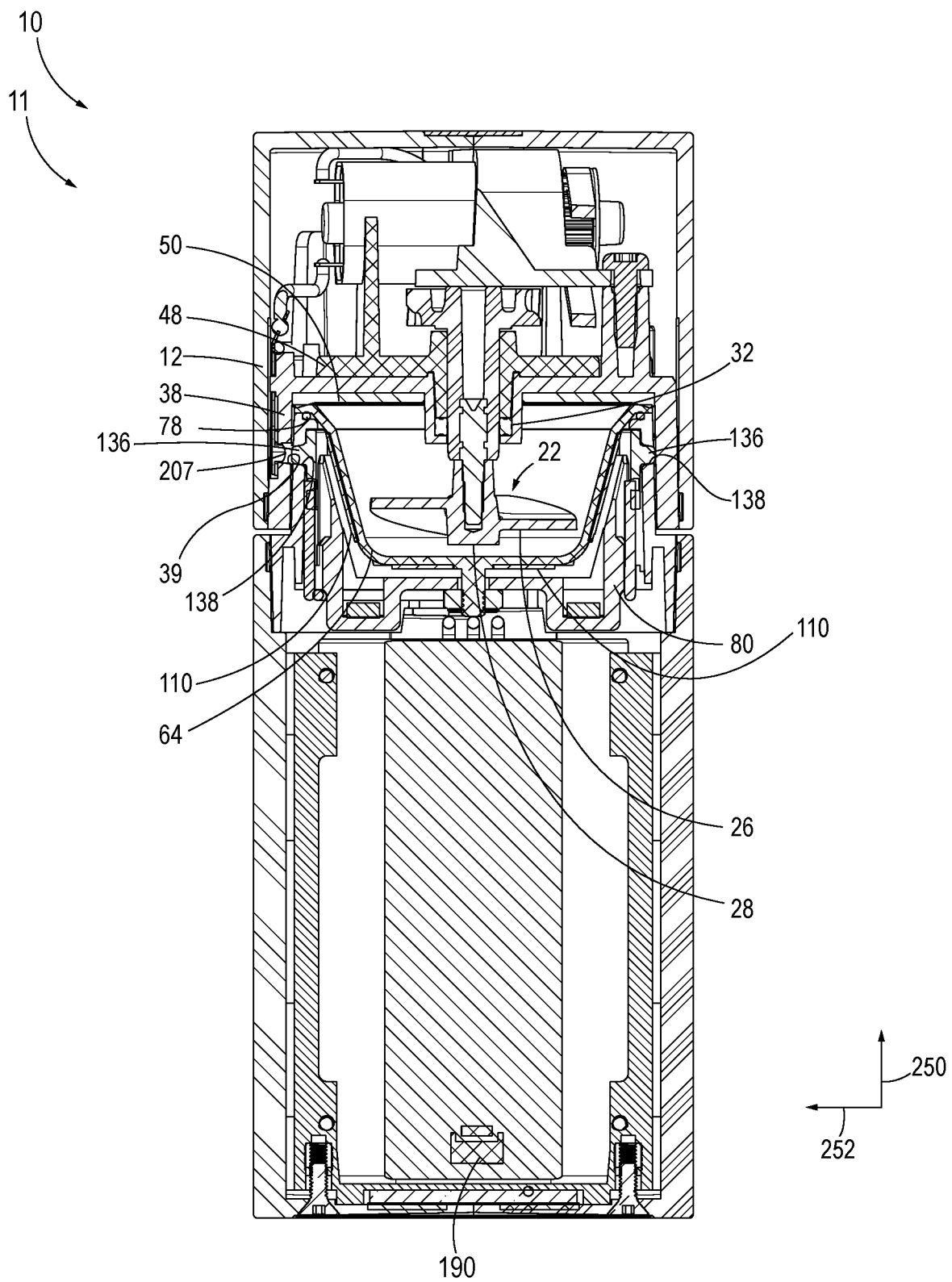
FIG. 10 is a cross-sectional view of the example cosmetic blending device of FIG. 2.

FIGS. 2-4 illustrate the exterior of the example cosmetic blending device 11, while FIGS. 5-8 illustrate the interior of the example cosmetic blending device with portions of outer housing 12 removed to enable illustration of interior components of the device. In FIGS. 2-4, FIG. 2 illustrates the example cosmetic blending device in the closed position, FIG. 3 illustrates the example cosmetic blending device in the open position, and FIG. 4 illustrates the base of the example cosmetic blending device when it includes cosmetic liquid 330, such as after the completion of a blending cycle. FIGS. 5-8 illustrate different isometric views of the interior of the example cosmetic blending device, with bottom cap 38 of lid 20 and top cap 61 of base 60 removed to more clearly show some of the interior components of the example cosmetic blending device 11. FIGS. 9-10 illustrate cross-sectional views of example cosmetic blending device 11. In particular, FIG. 9 illustrates a cross-section of example cosmetic blending device 11 taken along a longitudinal plane defined by longitudinal axis 254 and vertical axis 250. FIG. 10 illustrated a cross-section of example cosmetic blending device 11 taken along a lateral plane defined by lateral axis 252 and vertical axis 250. Axes 250, 252, and 254 are orthogonal to one another, and thus define three orthogonal planes in three-dimensional space.

As described in greater detail herein, a user may adjust the cosmetic blending device to the open position and insert solid-shell cosmetic ingredient capsule 300 (as illustrated in FIG. 3). A user then may adjust the cosmetic blending device to the closed position (as illustrated in FIG. 2) and initiate a blending cycle by, for example, pressing a button 212 or other actuator. Once the blending cycle is complete (i.e., cosmetic blending device 10 has completed the heating and blending of solid-shell cosmetic ingredient capsule 300 to form cosmetic liquid 330), the cosmetic blending device may notify the user that the cosmetic liquid is ready for extraction, such as via one or more lights 221 and/or one or more sounds. A user then may adjust the cosmetic blending device to the open position and extract cosmetic liquid 330 (as illustrated somewhat schematically in FIG. 4).

When lid 20 and base 60 are in the closed position (as illustrated in FIG. 2), only housing 12, user input device 210, and optionally a user feedback device 220 may be visible to a user. Thus, the user input device 210, user feedback device 220 and housing 12 may define the exterior of example cosmetic blending device 11. In example cosmetic blending device 11, user input device 210 and user feedback device 220 are included in base 60. However, in other examples, user input device 210 and/or user feedback device 220 may be included in lid 20. The user input device 210 may comprise button 212, and button 212 may be configured to initiate a blending cycle as introduced above. As an example, button 212 may be an ON/OFF button that may be configured to initiate a blending cycle. In particular, button 212 may be configured to depress when pushed by a user. User input device 210 may include a spring 214 (shown in FIG. 7) or other biasing mechanism or toggle behind button 212, (on the inside of base 60, interior to housing 12) that may compress to permit button 212 to depress when pushed/pressed by a user. The spring, in turn, may activate one or more circuits on controller 172, which may cause the controller 172 to initiate the heating and blending. Thus, the example cosmetic blending device 11 may be described as including a spring-actuated, or biased, ON/OFF button.

In other examples of cosmetic blending devices 10 according to the present disclosure, the user input device 210 may comprise other types of ON/OFF buttons, and/or may include more than one button. It also is within the scope of the present disclosure that user input device 210 may include other types of user input devices 210, such as touchscreens, joysticks, switches, etc. For example, such user input devices 210 may indicate the type of cosmetic ingredient capsule 300 being inserted into the blending chamber and/or the type of cosmetic liquid 330 to be produced. Further, as described above in the description of FIG. 1, controller 172 may be configured to initiate the heating and blending without input from a user, and instead may initiate the blending cycle autonomously based on sensed parameters. For example, controller 172 may automatically initiate a blending cycle in response to sensing that lid 20 and base 60 are in the closed position when controller 172 has determined that solid-shell cosmetic ingredient capsule 300 has been inserted into bowl-shaped depression 64.

User feedback device 220 may be configured to indicate a status of the heating and blending to the user and/or a fault condition. For example, user feedback device 220 may include one or more lights 221. Lights 221 may be configured to notify, or alert, a user of such statuses of the device as when the cosmetic blending device is ready to be actuated, when the device is operating to form cosmetic liquid 330 from solid-shell cosmetic ingredient capsule 300, and/or when the blending cycle is complete and cosmetic liquid 330 is ready for application to the user's skin, hair, and/or nails. For example, one or more of the brightness/intensity, color, and/or illumination pattern of lights 221 may change to indicate one or more of these statuses, with different lights being actuated and/or different illumination patterns optionally being utilized to differentiate the various statuses. The lights may be generated by a light source 222 (shown in FIGS. 5. and 7). The light source may include LED and/or halogen bulbs. Although five lights are shown in FIG. 2, other numbers of lights may be used, with examples including one light, two to four lights, and more than five lights. Additionally or alternatively, other types of hardware may be included to provide other visual alerts and/or different types of alerts, such as audible and/or tactile alerts. For example, the user feedback device 220 may include a display screen (for providing different visual alerts), and/or a speaker (for providing audible alerts).

When lid 20 and base 60 of example cosmetic blending device 11 are adjusted to the open position (as illustrated in FIG. 3), lid 20 and base 60 are separated to reveal and provide access to blending element 22 of lid 20 and bowl-shaped depression 64 of base 60. In example cosmetic blending device 11, lid 20 and base 60 are not connected by a hinge or other tether when the device is in the open position, and the lid and base thus may be described as being completely decoupled when the device is in the open position. As discussed herein, it is within the scope of the present disclosure that lid 20 and base 60 optionally may be interconnected by a hinge, tether, or other permanent coupling structure when the device is in the open position.

As illustrated in FIG. 3, when lid 20 and base 60 are in the open position, solid-shell cosmetic ingredient capsule 300 may be inserted into bowl-shaped depression 64 of base 60, and optionally into cosmetic ingredient receptacle 150 when the example cosmetic blending device 11 is used with such a receptacle. When included, cosmetic ingredient receptacle 150 may be inserted into bowl-shaped depression 64. Cosmetic ingredient receptacle 150 may be configured to line bowl-shaped depression 64. As such, cosmetic ingredient receptacle 150 may have the same and/or similar geometry to bowl-shaped depression 64, as illustrated in FIG. 3. After inserting solid-shell cosmetic ingredient capsule 300 (and optionally cosmetic ingredient receptacle 150) into bowl-shaped depression 64 of base 60, a user then may couple lid 20 to base 60 and adjust lid 20 and base 60 to the closed position (illustrated in FIG. 2).

Base 60 may include a top cap 61 that may at least partially surround bowl-shaped depression 64, and lid 20 may include a bottom cap 38 that may at least partially surround cavity 42. Top cap 61 and bowl-shaped depression 64 may be integrally formed together during the manufacturing process (e.g., they may be injection molded or die casted together), and thus may form a unitary piece. However, in other examples, top cap 61 and bowl-shaped depression 64 may be manufactured separately and may form two or more discrete pieces. In such examples, bowl-shaped depression 64 and top cap 61 may be coupled to one another after they are produced, such as via an adhesive, weld, and/or fastener.

Top cap 61 and bowl-shaped depression 64 may be fluidly sealed with respect to one another to restrict and/or prevent fluid flow there-between, such as to an exterior of the cosmetic mixing device or to internal regions of the device that are not designed to be exposed to the cosmetic liquid. As an example, example cosmetic blending device 11 may include a seal 78 (shown in FIGS. 7-10) between top cap 61 (shown in FIG. 3) and bowl-shaped depression 64. Seal 78 may be configured to ensure that cosmetic liquid 330 and/or any other fluids in bowl-shaped depression do not leak, spill, and/or otherwise pass into the interior of base 60, such as to liquid-sensitive internal components like controller 172 and/or internal electrical energy source 166. Seal 78 may extend around a periphery of bowl-shaped depression 64, underneath the bowl-shaped depression 64, or between the bowl-shaped depression and the top cap. In particular, bowl-shaped depression 64 may include a chamfered edge 72 at a top of the bowl-shaped depression, most proximate top 62 of base 60, and seal 78 may be positioned underneath this chamfered edge 72 of the bowl-shaped depression. Bowl-shaped depression 64 further may include an optional spout 74 that may be configured to funnel and/or pour out cosmetic liquid 330, as illustrated in FIG. 3. As discussed herein, a user optionally may choose to dispense, or remove, cosmetic liquid 330 by dipping one or more of the user's fingers into the cosmetic liquid within bowl-shaped depression 64. Spout 74 may form a groove in chamfered edge 72 and/or sidewalls 68 of bowl-shaped depression 64.

Bottom cap 38 of lid 20 may form and/or define cavity 42. Blending element 22 may extend and/or protrude from at least a portion of cavity 42, such that cutting edges 28 extend into bowl-shaped depression 64 when lid 20 and base 60 are adjusted to the closed position. When adjusted to the closed position (as illustrated in FIG. 2), bottom cap 38 of lid 20 may overlie top cap 61 of base 60. Stated slightly differently, top cap 61 of base 60 may extend inside cavity 42. In this way, top cap 61 of base 60 and bottom cap 38 of lid 20 may overlap when lid 20 and base 60 are adjusted to the closed position.

As perhaps best seen in FIG. 3, top cap 61 and bottom cap 38 may include portions of releasable locking structure 134 in the regions where top cap 61 and bottom 38 overlap and directly interface with one another. For example, the portion of the releasable locking structure 134 included in base 60 may be positioned on a peripheral exterior surface of top cap 61, and the portion of the releasable locking structure 134 included in lid 20 may be positioned on a peripheral interior surface of bottom cap 38 of lid 20, as illustrated in at least FIG. 3. Thus, when lid 20 is placed on top of base 60, top cap 61 may extend into cavity 42 of lid 20, and bottom cap 38 of lid 20 may surround the periphery of top cap 61 of base 60. That is, top cap 61 and bottom cap 38 may be concentric, with bottom cap 38 surrounding top cap 61.

In the examples of FIGS. 2-10, the releasable locking structure 134 of example cosmetic blending device 11 is illustrated as including a threaded engagement. In particular, the portion of releasable locking structure 134 included in base 60 may include threads 136, and the portion of releasable locking structure 134 included in lid 20 may include grooves 138. Grooves 138 may be sized and/or otherwise configured to receive threads 136. As illustrated in FIG. 3, threads 136 and grooves 138 may be configured to tighten lid 20 against base 60 when lid 20 is rotated by a user in a clockwise direction (when viewed from above). When threads 136 and grooves 138 are oriented to tighten in this clockwise direction, blending element 22 may be configured to rotate in a counter-clockwise direction (when viewed from above), opposite the tightening direction, as described above in the description of FIG. 1.

Threads 136 may be integrally included in top cap 61 (e.g., formed concurrently with top cap 61 via injection molding, die casting, etc.), or may be formed separately from top cap 61 and then coupled to top cap 61 afterwards. Grooves 138 may be integrally formed in bottom cap 38 or machined or otherwise cut out of bottom cap 38 after bottom cap 38 is formed.

As discussed previously, power transmitting structure 204 may be included in releasable locking structure 134. In example cosmetic blending device 11, threads 136 may include at least a portion of power transmitting structure 204. Power transmitting structure 204 may include separate portions in lid 20 and base 60. Specifically, power transmitting structure 204 may include a first electrical contact 207 that may be included in lid 20 and a second electrical contact 209 that may be included in base 60. In example cosmetic blending device 11, threads 136 may include second electrical contact 209. As discussed previously, first electrical contact 207 and second electrical contact 209 may include an electrically conductive material that is configured to readily conduct and/or transfer electric current between lid 20 and base 60. Thus, threads 136 may be constructed from, and/or may include, electrically conductive material, such as one or more metals and/or metal alloys. Threads 136 may be in electrical communication with first electrical contact 207 of lid 20, via conduction due to direct physical contact with first electrical contact 207 and/or via induction due to close proximity to first electrical contact 207.

In some examples, bottom cap 38 may include an aperture 39 that extends through bottom cap 38 of lid 20, from groove 138 to an exterior peripheral surface of bottom cap 38 that faces housing 12. First electrical contact 207 may be positioned between the bottom cap 38 and housing 12, and may extend through aperture 39 in bottom cap 38 and physically contact threads 136 (as illustrated in at least FIG. 10) when threads 136 are threaded into groove 138, such as in the closed position. In some examples, first electrical contact 207 may physically contact threads 136 only when lid 20 and base 60 are adjusted to the closed position. In this way, threads 136 and first electrical contact 207 may ensure that interlock 206 transmits power between base 60 and lid 20 only when the lid 20 and base 60 are in the closed position. Thus, in the closed position, threads 136 may extend into groove 138 and may physically contact first electrical contact 207, which may extend through bottom cap 38 and/or into groove 138 via aperture 39.

Turning to more of the internal components of example cosmetic blending device 11 (illustrated collectively in FIGS. 5-10), base 60 provides an example of a cosmetic blending device that includes central controller 174, which may comprise multiple circuit boards, and internal electrical energy source 166. Thus, central controller 174 and internal electrical energy source 166 may be included within housing 12, and below bowl-shaped depression 64. Internal electrical energy source 166 may include one or more batteries 167. Batteries 167 may be rechargeable batteries, and in such examples, example cosmetic blending device 11 additionally may include a charge coil 168 that may be configured to accept electric power from charging station 164. In particular, the charge coil may utilize inductive charging (e.g., Qi charging) to wirelessly transfer power from charging station 164 to batteries 167. Thus, charge coil 168 may be electrically connected (via a wired or wireless connection) to batteries 167. Additionally or alternatively, charge coil 168 may be electrically connected to central controller 174 via a charge coil connector 169 (illustrated in FIGS. 7-8).

Central controller 174 of controller 172 may include a first circuit board 176 and a second circuit board 178. Second circuit board 178 may be configured to control user feedback device 220 and/or to initiate a blending cycle based on user input from button 212. Thus, second circuit board 178 may be a user interface circuit board that may be configured to interface with the user (receive input from, and/or provide feedback to, the user). As discussed above, second circuit board 178 may receive input from button 212, optionally via spring 214. Thus, when utilized, spring 214 may actuate and/or physically contact second circuit board 178. Spring 214 may alter a switch or other electrical circuitry of second circuit board 178 when button 212 is pushed by a user to cause second circuit board 178 to initiate a blending cycle. Second circuit board 178 additionally or alternatively may include, support, and/or control light source 222 or other user feedback device 220. Light source 222 may be positioned between second circuit board 178 and housing 12, and may be configured to project lights 221 through apertures in housing 12. Second circuit board 178 may be programmed to control light source 222 to adjust one or more of the intensity, color, and/or illumination pattern of the lights to provide feedback to a user, such as to indicate a device status and/or provide an alert to the user, examples of which are discussed herein.

First circuit board 176 (as illustrated in at least FIG. 5) may be configured to control some or all of the other autonomous operation of example cosmetic blending device 11 (e.g., determining blend parameters, running the heating and blending during a blending cycle, adjusting blend parameters during a blending cycle, controlling operation of the various electronic actuators, receiving feedback from the various sensors, etc.). Thus, first circuit board 176 may include charge coil connector 169.

Additionally or alternatively, first circuit board 176 may include a thermistor connector 199 that may be configured to electrically connect first circuit board 176 to a thermistor 198 of thermal sensor 196. Thus, thermal sensor 196 may include thermistor 198, and thermistor 198 may be configured to measure a temperature of one or more thermal element(s) 110, blending chamber 100, capsule 300, cosmetic liquid 330, and/or blending element 22, as described in more detail herein. Thermistor 198 may be coupled to an exterior, peripheral surface of thermal element 110 and/or bowl-shaped depression 64, as illustrated in at least FIGS. 7-8. Thermal element 110 may further include a thermal breaker 112 that may be configured to automatically restrict and/or interrupt current flow to thermal element 110 to protect thermal element 110 from damage and/or to prevent overheating of thermal element 110, blending chamber 100, solid-shell cosmetic ingredient capsule 300, cosmetic liquid 330, blending element 22, and/or other components of example cosmetic blending device 11. Thus, thermal breaker 112 may be a circuit breaker. In the example illustrated in FIGS. 4-10, thermal element 110 may include a flex circuit.

Base 60 also may include a bowl mount 80 positioned between bowl-shaped depression 64 and the batteries and central controller 174. Thus, bowl mount 80 may separate central controller 174 and batteries 167 from bowl-shaped depression 64. Bowl mount 80 may be configured to provide structural support and/or stability to bowl-shaped depression 64. Thus, bowl-shaped depression 64 may rest on and/or be physically/mechanically supported by bowl mount 80.

Base 60 further may include a motor connector 190 coupled to, included in, and/or supported by, first circuit board 176. The motor connector 190 may electrically connect wiring 192 for drive mechanism 120 to first circuit board 176 and/or batteries 167. Wiring 192 may extend from motor connector 190 through an aperture in base mount 80 to second electrical contacts 209, which may be included in threads 136, as described above, and/or may be included in their own dedicated structure(s) (as illustrated in at least FIG. 4) in example cosmetic blending device 10. In particular, wiring 192 may include positive wires 193 that extend to threads 136, and negative wires 194 that extend to one of second electrical contacts 209 that may comprise its own dedicated structure (i.e., to an electrical contact that is not included in threads 136). Thus, electric current in positive wires 193 may flow between motor connector 190 and the threads 136, and electric current in negative wires 194 may flow between motor connector 190 and one or more of second electrical contacts 209 that may form, define, and/or include their own physical structure in example cosmetic blending device 11.

Current may flow between lid 20 and base 60 by flowing between the second electrical contact 209 and the first electrical contact 207, as described above. Positive wires 193 then may connect the one or more of the first electrical contacts in contact with threads 136 to drive mechanism 120, and negative wiring 194 may connect the different one of the first electrical contacts (the one not in contact with the threads) to drive mechanism 120. Thus, wiring 192 may be included in both lid 20 and base 60, and may be interrupted only in the transition between lid 20 and base 60, where first electrical contact 207 and second electrical contact 209 (e.g., threads 136) of the power transmitting structure 204 may be configured to selectively transfer current between the wiring in lid 20 and base 60.

Second electrical contact 209 may include at least one second electrical contact 209, at least two second electrical contacts 209, at least three second electrical contacts 209, and/or at least four second electrical contacts 209. As an example, base 60 may include three second electrical contacts 209. Two of the three second electrical contacts may be separated from one another by 180 degrees (and thus may be referred to as the diametrically opposed contacts of the three second electrical contacts) and the other one of the three second electrical contacts is positioned in-between these two electrical contacts (hence it is referred to herein as a middle contact of the three second electrical contacts). As one such example, the middle contact is positioned equidistant between the other two of the three second electrical contacts (i.e., 90 degrees from each of the two of the three second electrical contacts). As another example, base 60 may include two threads 136 that are positioned on opposite sides of top cap 61 (e.g., 180 degrees apart from one another as perhaps best illustrated in FIG. 10 and also as illustrated in FIGS. 3-8), each of which include second electrical contact 209. A third second electrical contact may be included between the two threads and may include its own structure (i.e., it may not be included in a thread). For example, as illustrated in FIG. 4, the middle contact of the three second electrical contacts may include a hemispherical contact that extends through an aperture in top cap 61.

The middle contact (e.g., the hemispherical contact) may be configured to connect to opposite wiring from the other two second electrical contacts of the three second electrical contacts. As an example, the hemispherical contact and the threads may be configured to each connect to opposite wiring. In some such examples, the hemispherical contact may be connected to the negative wiring in the base and may be configured to selectively connect to the negative wiring in the lid (via one of the first electrical contacts in the lid), and the threads may be connected to the positive wiring in the base and may be configured to selectively connect to the positive wiring in the lid (via one or more of the first electrical contacts in the lid).

First electrical contact 207 may include at least one first electrical contact 207, at least two first electrical contacts 207, at least three first electrical contacts 207, and/or at least four first electrical contacts 207. As an example, lid 20 may include three first electrical contacts 207. In some such examples, two of the three first electrical contacts may be configured to connect at least a portion of the negative wiring in the lid to the middle contact of the second electrical contact (e.g., the hemispherical contact) in the base (and thus connecting to the negative wiring in the base). The other first electrical contact may be configured to connect at least a portion of the positive wiring in the lid to at least one of the threads in the base (and thus connecting to the positive wiring in the base). Similar to the second electrical contacts, two of the three first electrical contacts (e.g., the ones configured to selectively connect to the hemispherical contact) may be positioned 180 degrees apart, and the contact in-between these two of the three first electrical contacts (e.g., a middle contact of the three first electrical contacts) may be positioned the same distance from these two of the three first electrical contacts as the middle contact of the three second electrical contacts is positioned from the two diametrically opposed contacts of the three second electrical contacts. In this way, when the lid and the base are adjusted to the closed position, the middle contact of the three first electrical contacts may physically contact one of the two diametrically opposed contacts of the three second electrical contacts (e.g., may physically contact thread 136) and one of the two diametrically opposed contacts of first electrical contacts may physically contact the middle contact (e.g., the hemispherical contact) of the three second electrical contacts.

By including three of the first electrical contacts and/or three of the second electrical contacts, the lid and the base may be adjusted to the closed position in two different orientations. Stated slightly differently, the closed position may include two different orientations between the lid and the base, and the closed position may be achieved in both orientations.

Drive mechanism 120 may include at least one electric motor 121. Electric motor 121 may have any suitable power rating, or output, to drive blending element 22 to blend capsule 300 to form cosmetic liquid 330. For example, electric motor 121 may have a motor constant $K_M$ of at least 0.1 Newton-centimeter per square root watt ($N \cdot cm \cdot W^{-1/2}$), at least 0.2 $N \cdot cm \cdot W^{-1/2}$, at least 0.3 $N \cdot cm \cdot W^{-1/2}$, at least 0.4 $N \cdot cm \cdot W^{-1/2}$, at least 0.45 $N \cdot cm \cdot W^{-1/2}$, at least 0.5 $N \cdot cm \cdot W^{-1/2}$, at least 0.6 $N \cdot cm \cdot W^{-1/2}$, at least 0.7 $N \cdot cm \cdot W^{-1/2}$, at least 0.8 $N \cdot cm \cdot W^{-1/2}$, at least 0.9 $N \cdot cm \cdot W^{-1/2}$, at least 1.0 $N \cdot cm \cdot W^{-1/2}$, at most 3 $N \cdot cm \cdot W^{-1/2}$, at most 2.5 $N \cdot cm \cdot W^{-1/2}$, at most 2 $N \cdot cm \cdot W^{-1/2}$, at most 1.75 $N \cdot cm \cdot W^{-1/2}$, at most 1.5 $N \cdot cm \cdot W^{-1/2}$, at most 1.25 $N \cdot cm \cdot W^{-1/2}$, and/or at most 1 $N \cdot cm \cdot W^{-1/2}$. Thus, positive wires 193 may be connected to a positive terminal of electric motor 121, and negative wires 194 may be connected to a negative terminal of electric motor 121. Electric motor 121 may be configured to convert electric energy supplied by controller 172 and/or batteries 167 into mechanical rotation (torque output). Torque output by electric motor 121 may be transmitted to blending element 22 via mechanical linkage 122. Mechanical linkage 122 may include a belt 124, worm gear 126, and helical gear 128. Belt 124 may be stretched around an output gear of electric motor 121 and worm gear 126 and may be configured to rotate worm gear 126 when electric motor 121 spins. Worm gear 126, in turn, may be configured to rotate helical gear 128, except the axis of rotation of worm gear 126 and helical gear 128 may be orthogonal to one another. That is, worm gear 126 may rotate along a rotational axis that is parallel to lateral axis 252, and helical gear may rotate along a rotational axis that is parallel to vertical axis 250. In this way, torque output by electric motor 121 may be converted to a vertical orientation when electric motor 121 is oriented in a horizontal position.

Helical gear 128 may be configured to co-rotate with blending element 22 such that blending element 22 spins whenever helical gear spins. As examples, helical gear 128 may be integrally formed with blending element 22 (i.e., they may form a unitary piece) and/or may be coupled to blending element 22 (specifically, shaft 24 of blending element 22). For example, helical gear 128 may be bonded to blending element 22 and/or fastened to blending element 22, such as via a threaded engagement. Thus, helical gear 128 and blending element 22 may be rotationally fixed relative to one another, such that they do not rotate relative to one another. That is, they may rotate together (i.e., at the same rate and direction). Electric motor 121 and mechanical linkage 122 may be physically and/or mechanically supported by a motor mount 48. Motor mount 48 may be positioned above bottom cap 38 of lid 20, between bottom cap 38 and electric motor 121 and mechanical linkage 122.

In some examples, a blending element seal 32 (shown in FIG. 10) may be included between helical gear 128 and bottom cap 38 of lid 20 to provide a fluid seal between blending element 22 and lid 20. Thus, blending element seal 32 may fluidly seal blending chamber 100 from the internal component of lid 20 (elements positioned above bottom cap 38 of lid 20). Additionally or alternatively, example cosmetic blending device 11 may include a seal 78 in cavity 42 of bottom cap 38. Seal 78 may be coupled to bottom cap 38 in the cavity and may help fluidly seal blending chamber 100 from the internal components of lid 20.

As illustrated in FIGS. 3, 9, and 11, blending element 22 may include three cutting edges 28, although a greater or lesser number of cutting edges may be utilized as discussed herein. The cutting edges may be spaced apart from one another and may curve upwards, towards helical gear 128. In some examples, the cutting edges may include the same geometry, size, shape, angle of curvature, pitch, and/or dimensions. Additionally or alternatively, the cutting edges may be positioned at the same height on shaft 24. For example, the cutting edges may be flush with bottom 26 of blending element 22 and may angle upwards along shaft 24 at a designated pitch. In another example, the cutting edges may be spaced above the bottom of blending element 22 at a common height. However, in other examples, the cutting edges may be different geometries, sizes, shapes, pitches, and/or dimensions, and/or may be positioned at different heights along shaft 24.

Focusing on FIG. 11, three examples of blending elements 22 are shown and generally indicated at 23. The left-most example of blending element 23 comprises a forked cutting surface, effectively including two cutting edges 28. The middle example of blending elements 23 is the same as the example blending element shown in FIGS. 3 and 9-10 and includes three cutting edges 28. The right-most example of blending element 23 does not comprise cutting edges 28 and may comprise one or more blunt projections and a flat bottom. As illustrated in FIG. 11, blending elements 22 optionally may include one or more voids 30 that may be configured to reduce a weight of blending element 22. The one or more voids 30 also may be referred to as hollow regions 30, apertures 30, and/or cavities 30. The voids 30 may reduce the weight of the blending element 22 and may therefore reduce the power consumption of electric motor 121. In this way, the energy efficiency of example cosmetic blending device 11 may be increased. Voids 30, when present, also may provide more turbulent and/or efficient blending of capsule 300 to produce cosmetic liquid 330, such as by permitting portions of capsule 300 and/or cosmetic liquid 330 to flow through the voids during operation of device 11.

Figure 12:
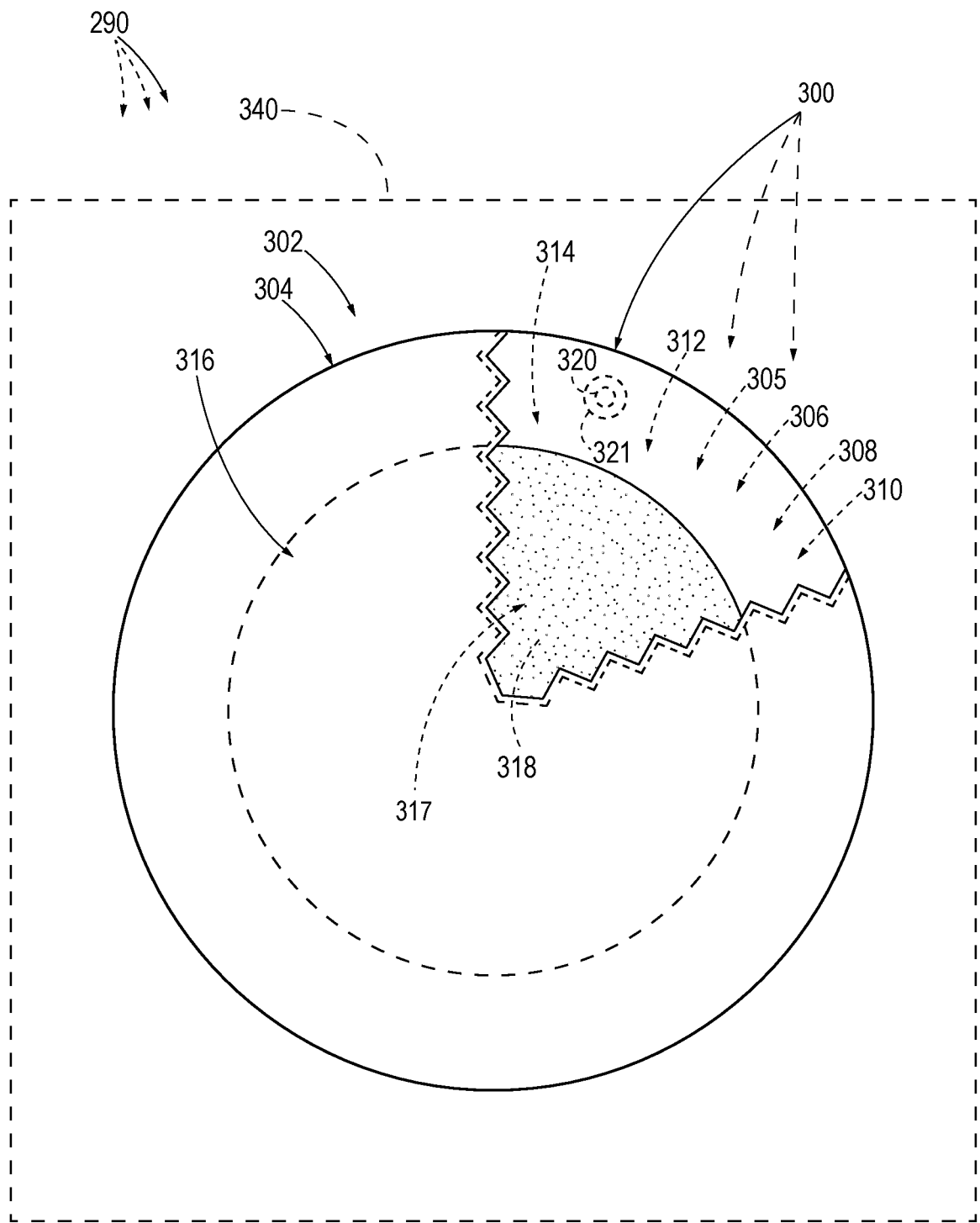
FIG. 12 is a schematic representation of examples of solid-shell cosmetic ingredient capsules according to the present disclosure.
Figure 13:
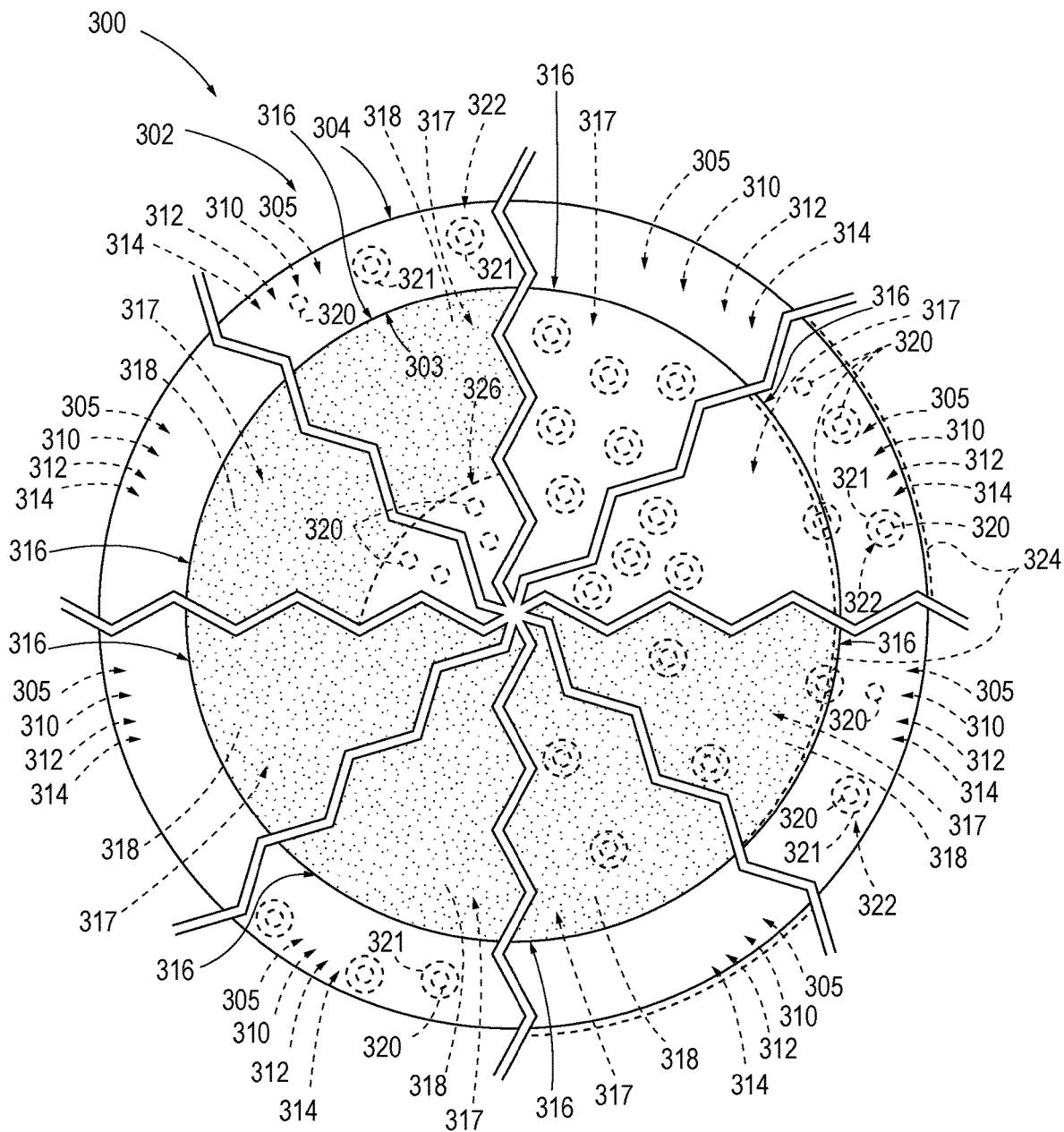
FIG. 13 is a schematic representation of additional examples of solid-shell cosmetic ingredient capsules according to the present disclosure.

FIGS. 12 and 13 schematically illustrate examples of solid-shell cosmetic ingredient capsule 300, according to the present disclosure. For brevity's sake, solid-shell cosmetic ingredient capsule 300 (also referred to as packageless cosmetic ingredient capsule 300, single-use cosmetic ingredient capsule 300, unblended cosmetic product 300, to-be-blended cosmetic product 300, cosmetic liquid precursor 300, not-skin-ready cosmetic product 300, and/or blendable non-homogenous cosmetic product 300) may be referred to as simply capsule 300 in the discussion of the solid-shell cosmetic ingredient capsule herein. FIG. 12 schematically illustrates how solid-shell cosmetic ingredient capsule 300 may be shipped and/or sold in packaging 340, which as discussed herein, is removed from the solid-shell cosmetic ingredient capsule prior to insertion of the solid-shell cosmetic ingredient capsule into cosmetic blending device 10. FIG. 13 schematically illustrates more detailed cross-sections of various examples of solid-shell cosmetic ingredient capsules 300 according to the present disclosure.

More specifically, FIG. 12 illustrates solid-shell cosmetic ingredient capsule 300 schematically, with a portion of shell 302 cut away, revealing optional components of the solid-shell cosmetic ingredient capsule 300, such as personal care ingredient 318. FIG. 13 illustrates cross-sections of eight example configurations of solid-shell cosmetic ingredient capsule 300. The eight example configurations are separated by broken lines and illustrate various example combinations of optional components of the solid-shell cosmetic ingredient capsule 300. However, it should be appreciated that other combinations of the optional components are possible. Additional optional examples are disclosed in U.S. Patent Application Publication No. 2019/0070078, the disclosure of which is incorporated herein by reference.

As illustrated in FIGS. 12 and 13, solid-shell cosmetic ingredient capsule 300 includes a shell 302 defining an enclosed inner volume 316. The enclosed inner volume 316 may be, may form, and/or may define a hollow cavity that may be at least partially, and optionally completely, filled with a cosmetic material 317. Cosmetic material 317 may include at least one of a personal care ingredient 318 and an active ingredient 320. Thus, the personal care ingredient and/or the active ingredient may be included in enclosed inner volume 316. Additionally or alternatively, active ingredient 320 may be included in the shell.

Shell 302 may be configured to one or more of form, define, enclose, encapsulate, confine, surround, encase, protect, retain, hold, fluidly seal, and/or otherwise provide a barrier between enclosed inner volume 316 and the exterior of solid-shell cosmetic ingredient capsule 300 (i.e., the outside environment). In particular, shell 302 may be configured to be sufficiently rigid to define enclosed inner volume 316 and/or to maintain the shape, integrity, and/or volume of enclosed inner volume 316 prior to insertion of solid-shell cosmetic ingredient capsule 300 into the blending chamber of cosmetic blending device 10. In particular, shell 302 may be configured to be a solid (i.e., not a liquid) prior to being heated and blended in cosmetic blending device 10

(e.g., from when manufacturing of solid-shell cosmetic ingredient capsule 300 is complete, to when solid-shell cosmetic ingredient capsule 300 is placed into the blending chamber of cosmetic blending device 10). Thus, shell 302 may be configured to be a solid during transportation, sale/purchase, and/or storage of solid-shell cosmetic ingredient capsule 300, and shell 302 may not melt, leak, and/or otherwise deform prior to being inserted into the blending chamber of cosmetic blending device 10. As such, solid-shell cosmetic ingredient capsule 300 may be referred to herein as being "shelf stable," meaning that it may be configured to remain solid and/or not oxidize, such as during transportation and/or prior to use in cosmetic blending device 10 to form cosmetic liquid 330. When shell 302 is below its melting point (also referred to as its melting temperature), and is therefore a solid (i.e., in a solid phase or state), shell 302 may be configured to withstand a threshold compressive load that is applied to shell 302 or only deform when a compressive load greater than the threshold compressive load is applied to shell 302. Stated differently, when shell 302 is below its melting point, shell 302 may be configured to possess a threshold minimum compressive strength. In other words, when shell 302 is below its melting point, shell may be configured to sealably enclose inner volume 316 under compressive loads up to at least the threshold compressive load. Examples of the threshold compressive load and/or threshold minimum compressive strength include at least 1724 Newton per meter squared ($N/m^2$), at least 3447 $N/m^2$, at least 5,200 $N/m^2$, at least 5400 $N/m^2$, at least 9,890 $N/m^2$, at least 6,900 $N/m^2$, at least 8,600 $N/m^2$, at least 10,300 $N/m^2$, at least 12,000 $N/m^2$, at least 13,700 $N/m^2$, at least 15,400 $N/m^2$, at least 17,100 $N/m^2$, at least 18,800 $N/m^2$, at least 19,500 $N/m^2$, at least 21,200 $N/m^2$, at least 24,000 $N/m^2$, at least 27,000 $N/m^2$, at least 30,000 $N/m^2$, at least 33,000 $N/m^2$, at least 36,000 $N/m^2$, at least 39,000 $N/m^2$, at least 42,000 $N/m^2$, at least 45,000 $N/m^2$, at least 48,000 $N/m^2$, at least 51,000 $N/m^2$, at least 54,000 $N/m^2$, at least 57,000 $N/m^2$, at least 60,000 $N/m^2$, at least 63,000 $N/m^2$, at least 66,000 $N/m^2$, at least 69,000 $N/m^2$, at least 72,000 $N/m^2$, at most 110,000 $N/m^2$, at most 105,000 $N/m^2$, at most 100,000 $N/m^2$, at most 95,000 $N/m^2$, at most 90,000 $N/m^2$, at most 85,000 $N/m^2$, at most 80,000 $N/m^2$, at most 75,000 $N/m^2$, at most 70,000 $N/m^2$, at most 65,000 $N/m^2$, and/or at most 60,000 $N/m^2$ are applied to shell 302. Additionally or alternatively, when shell 302 is below its melting point, shell 302 may be configured to withstand a threshold crush force applied to shell 302, or only deform when a crush force greater than the threshold crush force is applied to the shell. Stated differently, shell 302 may comprise a threshold minimum crush resistance. In other words, when shell 302 is below its melting point, shell 302 may be configured to sealably enclose inner volume 316 under crush forces up to at least the threshold crush force. Examples of the threshold crush force and/or the crush resistance include at least 0.5 Newton (N), at least 1 N, at least 1.5 N, at least 2 N, at least 3 N, at least 3.5 N, at least 4 N, at least 4.5 N, at least 5 N, at least 5.5 N, at least 6 N, at least 6.5 N, at least 7 N, at least 7.5 N, at least 8 N, at least 8.5 N, at least 9 N, at least 9.5 N, at least 10 N, at least 11 N, at least 12 N, at least 13 N, at least 14 N, at most 14 N, at most 20 N, at most 21 N, at most 19 N, at most 18 N, at most 17 N, at most 16 N, at most 15 N, at most 14 N, at most 12 N, and/or at most 10 N. Further, shell 302 may have a melting point of at least 27° C., at least 28° C., at least 29° C., at least 30° C., at least 31° C., at least 32° C., at least 32.2° C., at least 33° C., at least 34° C., at least 35° C., at least 36° C., at least 37° C., at least 38° C., at least 39° C., at least 40° C., at most 52° C., at most 50° C., at most 48° C., at most 46° C., at most 44° C., at most 43° C., at most 42° C., at most 41° C., at most 40° C., at most 39° C., and/or at most 38° C. The compressive load and/or crush force at which shell 302 begins to deform may be referred to as the load-bearing capacity of shell 302. Thus, at compressive loads and/or crush forces below the load-bearing capacity of shell 302, shell 302 may not deform, but at compressive forces above the load-bearing capacity of shell 302, shell 302 may begin to deform.

Shell 302 may be described as being solid when shell 302 stably encloses, or seals, cosmetic material 317 within inner volume 316. Stated differently, shell 302 may be described as being solid within temperatures in which shell 302 is dimensionally stable, or at least substantially dimensionally stable, for example at least under its own weight and optionally the weight of the cosmetic material that is enclosed within the shell. Thus, shell 302 should be solid when its temperature is below its melting point, or melting point range. As shell 302 is heated to or above its melting point, shell 302 may soften or possess a lower load-bearing capacity when heated to temperatures close to its melting point range even though shell 302 is still solid.

As described above, shell 302 may deform prior to the heating and blending because blending element 22 may crush the shell when lid 20 and base 60 are adjusted to the closed position, after capsule 300 has been inserted into the blending chamber of the cosmetic blending device. That is, when lid 20 and base 60 are adjusted to the closed position, blending element 22 may apply a compressive force to shell 302 that is greater than the load-bearing capacity of the shell and/or otherwise sufficient to deform the shell (i.e., greater than the compressive load above which shell 302 may be configured to deform). However, shell 302 still may be solid after the lid and the base are adjusted to the closed position, before the heating and blending cycle commences. Shell 302 only may be deformed at this point. Thus, although shell 302 may be crushed, squished, and/or otherwise deformed by blending element 22, shell 302 may not melt to a liquid until the heating and blending cycle commences. That is, shell 302 may only melt and become a liquid after the heating and blending cycle commences. Shell 302 may have any suitable thickness to provide these properties. As examples, shell 302 may have a thickness of at least 0.5 mm, at least 0.75 mm, at least 1 mm, at least 1.25 mm, at least 1.5 mm, at least 2 mm, at least 2.25 mm, at least 2.5 mm, at least 2.75 mm, at least 3 mm, at least 3.25 mm, at least 3.5 mm, at least 3.75 mm, at least 4 mm, at most 10 mm, at most 9 mm, at most 8 mm, at most 7 mm, at most 6 mm, at most 5.5 mm, at most 5 mm, at most 4.5 mm, and/or at most 4 mm.

Shell 302 additionally or alternatively may be configured to restrict and/or prevent fluid transfer between enclosed inner volume 316 and the exterior of the solid-shell cosmetic ingredient capsule, such as when enclosed inner volume 316 includes liquids and/or when the capsule is exposed to humid environments. For example, shell 302 may be configured to be, and/or may be constructed from ingredients such that shell 302 is, one or more of hydrophobic, water-resistant, waterproof, and/or otherwise impervious to water. Shell 302 also or alternatively may be configured to not dissolve when exposed to water. In this way, shell 302 may be configured to retain, hold, and/or keep one or more water-based liquids (e.g., when the personal care ingredient and/or active ingredient is water-based) within enclosed inner volume 316, and/or to prevent escape, leakage, and/or spilling of the liquids out of solid-shell cosmetic ingredient capsule 300. Thus, shell 302 may be configured not only to define enclosed inner volume 316, but also to fluidly seal enclosed inner volume 316 from the outside environment. In this way, when cosmetic material 317 includes liquids, shell 302 may be configured to hold, retain, and/or otherwise keep the liquids within enclosed inner volume 316 and prevent them from leaking and/or spilling to the outside environment. Further, shell 302 may be configured to remain solid when in contact with cosmetic material 317 of enclosed inner volume 316. In this way, shell 302 may be configured to not dissolve and/or otherwise deform when exposed to cosmetic material 317 of enclosed inner volume 316. Thus, shell 302 may be configured to maintain its shape and/or the shape of enclosed inner volume 316 even when the cosmetic material of enclosed inner volume 316 includes various liquids and/or other fluids.

Shell 302 may be constructed and/or formed so that it does not absorb water from the atmosphere at a rate or quantity that would alter or impair the structural, crystalline, mechanical, and/or chemical properties of shell 302. Put in slightly different terms, shell 302 may possess limited water permeability, limited water sorption capacity, and/or a low water activity such that shell 302 does not absorb atmospheric water to a detrimental extent, does not absorb water from cosmetic material 317 within enclosed inner volume 316 to a detrimental extent, and/or limits migration of water between cosmetic material 317 and the environment (i.e., the atmosphere) surrounding shell 302. As more specific examples, shell 302 may be configured to possess a water activity ($a_w$) that is at least 0.1 $a_w$, at least 0.2 $a_w$, at least 0.3 $a_w$, at least 0.4 $a_w$, at least 0.5 $a_w$, at least 0.6 $a_w$, at most 0.1 $a_w$, at most 0.2 $a_w$, at most 0.3 $a_w$, at most 0.4 $a_w$, at most 0.5 $a_w$, and/or at most 0.6 $a_w$.

In view of the above, cosmetic material 317 may be configured to possess a low water activity and/or a water activity that is compatible with the water activity of shell 302. For example, particularly for compositions in which when cosmetic material 317 includes non-incidental amounts of water, cosmetic material 317 may include one or more humectants that are configured to lower the water activity of cosmetic material 317 by binding and/or deactivating at least some of and/or at least a substantial portion of the water component of cosmetic material 317. Stated in more general terms, cosmetic material 317 may include one or more humectants to reduce the propensity of water contained within cosmetic material 317 to permeate into, absorb into, permeate through, and/or leave through shell 302. As examples, cosmetic material 317 may be configured to possess a water activity ($a_w$) of at least 0.3 $a_w$, at least 0.4 $a_w$, at least 0.5 $a_w$, at least 0.6 $a_w$, at least 0.7 $a_w$, at most 0.3 $a_w$, at most 0.4 $a_w$, at most 0.5 $a_w$, at most 0.6 $a_w$, at most 0.7 $a_w$, and/or at most 0.8 $a_w$. Examples of suitable humectants that may be included in cosmetic material 317 include water soluble sugars, glycerin, propylene glycol, butylene glycol, propanediol, polyhydroxy acids, alpha-hydroxy acids, beta-hydroxy acids, hyaluronic acid, urea, lactates, and/or panthenol. Shell 302 also may include one or more humectants, such as any of the above-listed humectants, to reduce the water activity of shell 302 and/or reduce the propensity for water migration through and/or into shell 302. In particular, shell 302 may include humectants for lowering water activity when shell 302 and/or cosmetic material include non-incidental amounts of water.

Limiting or reducing the water activity of outer shell 302 and/or cosmetic material 317 also may improve the shelf life of solid-shell cosmetic ingredient capsule 300. For example, limiting or reducing the water activity of shell 302 and/or cosmetic material 317 may prevent, limit, or preclude the growth of microbes within solid-shell cosmetic ingredient capsule 300. As examples, a water activity of 0.9 $a_w$ or less typically prevents the growth of most bacteria, a water activity of 0.8 $a_w$ or less typically prevents growth of most yeasts, and a water activity of 0.6 $a_w$ or less typically prevents the growth of most fungi or molds. In addition to the above, limiting or reducing the water activity of outer shell 302 and/or cosmetic material 317 may prevent, reduce, or limit oxidation of oxidation-sensitive components or oxidation-sensitive ingredients (e.g., vitamin C, oxidation-sensitive lipids, and/or unsaturated lipids) that may be included in outer shell 302 and/or cosmetic material 317 by reducing or removing a medium in which redox reactions may occur.

Shell 302 may be configured to have the opposite polarity as personal care ingredient 318. For example, shell 302 may be configured to be hydrophobic, lipophilic, and/or nonpolar when personal care ingredient 318 is configured to be hydrophilic, lipophobic, and/or polar. Such an opposite polarity may improve the ability of shell 302 to retain cosmetic material 317, and/or personal care ingredient 318 or active ingredient 320 thereof, within enclosed inner volume 316. In particular, shell 302 may include one or more nonpolar molecules that may be hydrophobic and/or may not be water-soluble. As one such example, shell 302 may include one or more lipids 305, such as one or more of fats 306 (butters and/or oils), waxes 308, and/or phospholipids. As examples, the lipids may include one or more fatty acids and/or one or more fatty acids chemically combined with one or more alcohols (e.g., glycerol) to form one or more fatty acid esters. As an example, three fatty acids, which may be the same or different from one another, may combine with glycerol (a chemical compound having three alcohol groups) to form a triglyceride (a type of fat), in which the three fatty acid residues are ester linked to the glycerol backbone to form a fatty acid triester. Similarly, phospholipids may include phosphoric esters and/or phosphoric diesters. Butters, oils, and waxes typically include complex mixtures of fatty acid esters. Typically, butters primarily are comprised of triglycerides of various fatty acids, but also may include minor components of glyceryl monoesters, glyceryl diesters, and/or free fatty acids.

Shell 302 may include only one type of triglyceride, or shell 302 may include various combinations/blends of two or more triglycerides. Additionally or alternatively, shell 302 may include one or more triglycerides in combination with various other lipids, such as other butters, oils, waxes, and/or phospholipids. Shell 302 also may include one or more emulsifiers in combination with one or more triglycerides, and optionally one or more butters, oils, waxes, phospholipids and/or combinations thereof. Examples of suitable emulsifiers that may be included in shell 302 include glyceryl monoesters, glyceryl diesters, sorbitan monoesters, sorbitan diesters, sorbitan triesters, lactic acid esters, citric acid esters, sucrose esters, fatty acid esters (e.g., stearyl behenate, behenyl behenate, and stearyl stearate), phospholipid emulsifiers, and/or combinations thereof. In the description herein, butters are used to refer to fats that are solid at room temperature (20° C.), and oils are used to refer to fats that are liquid at room temperature. Thus, butters and oils are both fats, but butters have a higher melting point than oils (i.e., they may have a higher concentration of saturated fatty acids and/or a lower concentration of unsaturated fatty acids as compared to oils). Examples of suitable oils may include one or more of avocado oil, grape seed oil, hemp oil, primrose oil, bergamot oil, argan oil, and/or olive oil. Examples of suitable butters include one or more of shea butter, coconut-derived fats that are solid at room temperature (e.g., coconut oil), cocoa butter, kokum butter, palm-derived fats that are solid at room temperature (e.g., palm oil), Illipe butter, Murumuru butter, Babassu butter, and/or mango butter. Fats 306, and in some examples, the triglycerides, may comprise at least 30%, at least 35%, at least 40%, at least 45%, at least 50%, at least 55%, at least 60%, at least 65%, at least 70%, at least 75%, at most 99%, at most 95%, at most 90%, at most 85%, at most 80%, at most 75%, at most 70%, at most 65%, at most 60%, at most 55%, and/or at most 50% by weight of shell 302.

Waxes 308, when present, may include one or more types of waxes. As examples, the waxes may include naturally derived waxes (e.g., plant waxes and/or animal waxes), synthetic waxes, and/or partially synthetic waxes. More specific examples of waxes 308 include one or more of carnauba wax, rice bran wax, beeswax, soy wax, lanolin, jojoba wax, and/or paraffin wax. The waxes may be present in shell 302 in any particulate form, such as in bead form, and optionally may include purified or other chemical fractions of such waxes. As an example, waxes 308 may include jojoba wax beads and/or other types of wax beads. When included in shell 302, waxes 308 may comprise at least 2%, at least 5%, at least 10%, at least 15%, at least 20%, at least 25%, at least 30%, at least 35%, at most 45%, at most 40%, at most 35%, at most 30%, at most 25%, at most 20%, at most 15%, and/or at most 10% by weight of shell 302.

Additionally or alternatively, shell 302 may include other nonpolar molecules, such as resins 310. The resins, when present, may include one or more terpenes and/or terpenoids. As an example, the resins may include shellac. When included in shell 302, resins 310 may comprise at least 2.5%, at least 5%, at least 7.5%, at least 10%, at least 12.5%, at least 15%, at least 17.5%, at least 20%, at least 25%, at most 40%, at most 35%, at most 30%, at most 25%, at most 20%, at most 17.5%, at most 15%, at most 12.5%, and/or at most 10% by weight of shell 302.

Shell 302 additionally or alternatively may include one or more crystal promoters 312 that may be configured to promote and/or stabilize crystallization in shell 302 (i.e., the formation of crystals in shell 302). Thus, the crystal promoters may be configured to form and/or stabilize crystalline and/or lattice structures in shell 302. As examples, the crystal promoters may include one or more of saturated fats, hydrogenated oils, stearin, interestified fats (and in particular interestified triglycerides), fatty acids, fatty alcohols, fatty acid esters, and/or emulsifiers. When included in shell 302, crystal promoters 312 may comprise at least 0.25%, at least 0.5%, at least 1.0%, at least 1.5%, at least 2%, at least 2.5%, at least 3%, at least 4%, at least 6%, at least 8%, at least 10%, at least 12%, at least 14%, at most 25%, at most 24%, at most 22%, at most 20%, at most 18%, at most 16%, at most 14%, at most 12% and/or at most 10% by weight of shell 302.

Shell 302 additionally or alternatively may include one or more chemically inert materials 314 that may be configured to not chemically react with other components of shell 302, such as the fats, waxes, preservatives, and/or resins, when included. As examples, the chemically inert materials may include one or more of silica, alginate, starches, sugars, minerals, and/or gelatin. When included, chemically inert materials 314 may comprise at least 2%, at least 5%, at least 10%, at least 15%, at least 20%, at least 25%, at least 30%, at least 35%, at most 60%, at most 55%, at most 50%, at most 45%, at most 40%, at most 35%, at most 30%, at most 25%, at most 20%, at most 15%, and/or at most 10% by weight of shell 302. Including the chemically inert materials in the shell may reduce the amount of lipids 305 included in the shell. That is, the chemically inert materials may dilute the lipids in shell 302. In this way, the chemically inert materials may be included to alter one or more of the strength, rigidity, and/or melting point of capsule 300. In particular, the amount of chemically inert materials in shell 302 may be increased to increase the strength, rigidity, and/or melting point of capsule 300. Additionally or alternatively, inclusion of chemically inert materials in the shell 302 may alter the physical properties of the cosmetic liquid. For example, the amount of chemically inert materials in shell 302 may be adjusted to alter one or more characteristics such as texture, color, sheen, skin feel and/or viscosity of cosmetic liquid 330.

Shell 302 additionally or alternatively may include active ingredient 320. Active ingredient 320 may be configured to provide, and at least contribute to, the desired and/or purported effect of capsule 300 and/or cosmetic liquid 330. In particular, capsule 300 may be advertised and/or otherwise described to provide one or more purported skin, hair, and/or nail benefits for a user or consumer. As an example, a label may be included with solid-shell cosmetic ingredient capsule 300 that describes the desired effect(s) of the solid-shell cosmetic ingredient capsule 300. The desired and/or purported effects may include treatment for the underlying causes of one or more skin, hair and/or nail issues/conditions (dryness, wrinkles, acne, pigmentation issues, rosacea, psoriasis, eczema, keratosis pilaris, seborrheic dermatitis etc.), treatment for the symptoms of the one or more skin, hair, and/or nail issues/conditions, anti-aging benefits, anti-wrinkle benefits, lightening, darkening, strengthening, protection, nourishment, and/or other changes to the physical and/or chemical structure of the skin, hair, and/or nails.

Additionally or alternatively, active ingredient 320 may be configured to be one or more of pain relieving, antibacterial, anti-inflammatory, antispasmodic, disinfecting, astringent, hypoallergenic, regenerating, hydrating, moisturizing, conditioning, and/or relaxing. As examples, active ingredient 320 may include one or more of alpha-hydroxy acids (e.g., glycolic, lactic, tartaric, and citric acids), polyhydroxy acids, beta-hydroxy acids (e.g., salicylic acid), botanical derivatives (e.g. kojic acid), vitamins (e.g., retinoids, Vitamin A, Vitamin C, Vitamin E, etc.), minerals, silicas, acrylate, essential oils, prescription ingredients, proteins, peptides (e.g., copper peptide), anti-aging agents (e.g., hyaluronic acid, allantoin), antioxidants (e.g., alpha-lipoic acid), anti-wrinkle agents (e.g., dimethylaminoethanol or DMAE), sunscreen agents (e.g. titanium dioxide, zinc oxide), hair repair agents, humectants (e.g., propylene glycol, glycerin, water soluble sugars, butylene glycol, propanediol, polyhydroxy acids, alpha-hydroxy acids, beta-hydroxy acids, hyaluronic acid, urea, lactates, and/or panthenol), rejuvenating and soothing agents, skin lightening agents (e.g., hydroquinone), skin darkening agents, astringents, disinfectants, and/or liposomes.

In some examples, active ingredient 320 may be included by itself in shell 302 without an encapsulating coating 321. However, in other examples, active ingredient 320 may be included in shell 302 with an encapsulating coating 321. Examples of encapsulating coating 321 include one or more of a gelatin, wax, fats, lipids, phospholipids, triglycerides, and/or cellulose coating. When coated with encapsulating coating 321, active ingredient 320 may be discrete and/or non-homogenous with the rest of shell 302. However, when encapsulating coating 321 is not included, active ingredient 320 may form a homogenous or non-homogenous mixture with the rest of shell 302. Encapsulating coating 321 also may be referred to as active ingredient coating 321 and/or protective coating 321. When coated with active ingredient coating 321, active ingredient 320 may be referred to as a microcapsule 322. Thus, the microcapsule may include the active ingredient and the active ingredient coating. The protective coating may be configured to prevent dissolution of the microcapsule and/or active ingredient within the solid-shell cosmetic ingredient capsule. Additionally or alternatively, the protective coating may be configured to only dissolve when the solid-shell cosmetic ingredient capsule is heated and blended by cosmetic blending device 10 to produce the cosmetic liquid. For example, a water-soluble or humectant-soluble active ingredient coated with encapsulating coating 321 may dissolve with a water-containing or humectant-containing cosmetic material 317 when cosmetic ingredient capsule 300 is heated and blended by cosmetic blending device 10. Thus, the protective coating may have a melting point of at least the melting point of shell 302 and/or the components of shell 302, and/or the protective coating may be configured to dissolve into shell 302 and/or dissolve into cosmetic material 317 upon heating and blending by cosmetic blending device 10.

However, because the shell 302 is designed to remain solid prior to insertion into cosmetic blending device 10, when active ingredient 320 is included in shell 302 without protective coating 321, the active ingredient nonetheless may not dissolve within shell 302. Additionally or alternatively, the active ingredient may not oxidize in shell 302 at least in part because of the chemical composition of the shell. In particular, shell 302 may be substantially anhydrous (i.e., at most 4%, at most 2% and/or at most 1% by weight water) and/or completely anhydrous (i.e., may not contain any water), may not contain any gaseous oxygen, and/or may possess limited oxygen permeability, and may therefore not oxidize and/or prevent oxidation of active ingredient 320 when the active ingredient is included in the shell. Thus, by including the active ingredient in the shell, not only may the concentration of the active ingredient in the solid-shell cosmetic ingredient capsule be increased, but also the efficacy of the active ingredient may be increased because the shell may significantly reduce and/or prevent oxidation of the active ingredient compared to the amount that the active ingredient may oxidize in the enclosed inner volume. That is, the active ingredient may oxidize less in the shell than in the enclosed inner volume, particularly in examples where the enclosed inner volume includes air and/or water.

Further, by including the active ingredient in the shell, protective coating 321 may be omitted, therefore reducing the cost and complexity of solid-shell cosmetic ingredient capsule 300. And, as mentioned above, by including the active ingredient in the shell in addition to, and/or instead of, in the enclosed inner volume, the amount (e.g., concentration) of active ingredient in the solid-shell cosmetic ingredient capsule may be increased relative to the amount that may be included when the active ingredient is included only in the enclosed inner volume. In particular, active ingredient 320 may have a saturation concentration in the personal care ingredient or the cosmetic material, and active ingredient 320 may precipitate out of the personal care ingredient or the cosmetic material at concentrations greater than the saturation concentration. With this in mind, solid-shell cosmetic ingredient capsule 300 may include a first amount of active ingredient 320 within shell 302 and a second amount of active ingredient 320 in the cosmetic material or personal care ingredient. The total amount of active ingredient 320 in solid-shell cosmetic ingredient capsule 300, which in includes the first amount in the shell and the second amount in the enclosed inner volume, may be greater than the amount of active ingredient 320 that can be dissolved the volume of cosmetic material and/or personal care ingredient in inner volume 316. In other words, the total amount of active ingredient 320 may exceed the solubility limit of the active ingredient in the total volume of the cosmetic material or cosmetic care ingredient while the concentration of the active ingredient in the cosmetic material or cosmetic care ingredient may be less than its solubility limit therein.

Additionally or alternatively, active ingredient 320 may have a higher stable solubility in shell 302 than in personal care ingredient and/or cosmetic material, in that active ingredient 302 may begin to precipitate (i.e., out of the personal care ingredient and/or cosmetic material) at lower concentrations than it will tend to precipitate out of the shell. Thus, by including the active ingredient in the shell, the active ingredient may be included at higher concentrations in the shell than in the enclosed inner volume, without precipitating, thereby increasing the effective dosage of the active ingredient. In view of the above, solid-shell cosmetic ingredient capsule 300 and/or a cosmetic liquid 330 formed therefrom may have a concentration of active ingredient 320 that is greater than the saturation concentration of active ingredient 320 in the cosmetic material and/or the personal care ingredient, thereby increasing the effective dosage of the active ingredient in solid-shell cosmetic ingredient capsule 300.

In examples where active ingredient 320 is included in shell 302, active ingredient 320 may comprise at least 0.05%, at least 0.1%, at least 0.2%, at least 0.3%, at least 0.4%, at least 0.5%, at least 0.6%, at least 0.7%, at least 0.8%, at least 0.9%, at least 1%, at least 1.1%, at least 1.2%, at least 1.3%, at least 1.4%, at least 1.5%, at least 1.7%, at least 2%, at least 2.25%, at least 2.5%, at least 2.75%, at least 3%, at most 10%, at most 9%, at most 8%, at most 7%, at most 6%, at most 5%, at most 4.5%, at most 4.25%, at most 4%, at most 3.75%, at most 3.5%, at most 3.25%, at most 3%, at most 2.75%, at most 2.5%, at most 2.25%, at most 2%, at most 1.75%, at most 1.5%, at most 1.25% and/or at most 1% by weight of shell 302.

When included in shell 302, active ingredient 320 may be embedded in the shell. As an example, active ingredient 320 may be fully embedded in shell 302, such that the shell 302 fully surrounds the active ingredient 320. Additionally or alternatively, the active ingredient may be partially embedded in shell 302, such that at least a portion of the active ingredient 320 and/or its encapsulating coating 321 (when included) protrude into and/or, are directly exposed to, enclosed inner volume 316, as illustrated in FIG. 13.

Shell 302 optionally may be formed in, or with, one or more layers, which may have the same or different properties, components, thicknesses, etc. Additionally or alternatively, a shell coating 324 may be applied to shell 302 as illustrated in FIG. 13. In particular, shell coating 324 may be applied to an interior surface 303 and/or an exterior surface 304 of shell 302. The shell coating may be configured to provide one or more of added structural integrity to shell 302, added resistance to oxidation of the shell, and/or added resistance to water penetration into the shell, and/or a barrier between the interior surface of the shell and the contents of the shell's enclosed internal volume prior to blending of the capsule in the cosmetic blending device. When present, shell coating 324 additionally or alternatively may be configured to increase the melting point of the shell. As examples, coating 324 may include a gum (e.g., xanthan gum), starch, resin, proteins (e.g. gelatin, zein) and/or cellulose.

The exterior surface 304 of shell 302 may interface directly with the external environment (e.g., packaging 340, ambient air, bowl-shaped depression 64 of cosmetic blending device 10, etc.). In some examples, shell 302, and in particular exterior surface 304 of shell 302, may directly interface with ambient air. In particular, when being placed into cosmetic blending device 10 by a user, solid-shell cosmetic ingredient capsule 300 may not be covered by anything (e.g., packaging, lining, wrappings, etc.) and may interface directly with only ambient air and/or a user's fingers. Correspondingly, when placed in cosmetic blending device 10, the exterior surface 304 of shell 302 may directly interface with only ambient air and/or cosmetic blending device 10 (e.g., bowl-shaped depression 64 and/or cosmetic ingredient receptacle 150). Thus, when heated and blended by cosmetic blending device 10, the solid-shell cosmetic ingredient capsule 300 may be devoid of all packaging, wrappings, and/or linings, hence the reference herein to the capsule as packageless cosmetic ingredient capsule 300.

As introduced above, enclosed inner volume 316 may be formed, enclosed, and/or otherwise defined by shell 302. Thus, enclosed inner volume 316 may define and/or form a hollow enclosed volume, space, and/or cavity that may be configured to be fluidly sealed from the exterior environment. Enclosed inner volume 316 may be configured to comprise, contain, include, and/or otherwise be filled with cosmetic material 317, such as personal care ingredient 318 and/or active ingredient 320. Thus, cosmetic material 317 may at least partially, and optionally fully, fill enclosed inner volume 316. As examples, cosmetic material 317 may fill at least 50%, at least 60%, at least 70%, at least 75%, at least 80%, at least 85%, at least 90%, at least 95%, at least 97%, at least 98%, at least 99%, 100%, at most 100%, at most 99%, at most 95%, at most 90%, at most 85%, at most 80%, at most 75%, and/or at most 70% of the total volume of enclosed inner volume 316.

Since active ingredient 320 already has been discussed (in the context of shell 302), for the sake of brevity, the composition of active ingredient 320 is not discussed again herein. When active ingredient 320 is included in cosmetic material 317 and in shell 302, the active ingredient(s) in cosmetic material 317 may be the same as or different from the active ingredient(s) in shell 302. By including different actives in shell 302 and cosmetic material 317, solid-shell cosmetic ingredient capsule 300 may contain two different actives that may otherwise be incompatible with one another. That is, by segregating the two different actives in separate and discrete portions of the solid-shell cosmetic ingredient capsule, the two different actives may not interact prior to the heating and/or blending. In this way, chemically incompatible actives may still be contained in the same solid-shell cosmetic ingredient capsule.

Like in shell 302, active ingredient 320 optionally may include encapsulating coating 321. When active ingredient 320 is included, encapsulating coating 321 may be configured to prevent dissolution of the active ingredient within the enclosed inner volume 316, and more specifically to prevent dissolution of the active ingredient in personal care ingredient 318, when personal care ingredient 318 is included in enclosed inner volume 316. The encapsulating coating may be configured to provide a fluid seal/barrier between the personal care ingredient and the active ingredient. In this way, the active ingredient may be suspended in and/or fluidly sealed off from personal care ingredient 318 when included in enclosed inner volume 316. Encapsulating coating 321 thus may prevent and/or restrict oxidation of active ingredient 320, thereby increasing the efficacy of the active ingredient when solid-shell cosmetic ingredient capsule 300 is applied to a user's body. However, in other examples, active ingredient 320 may not include the protective coating when it is included in the enclosed inner volume 316.

In other examples, such as illustrated in FIG. 13, active ingredient 320 may be included in an optional compartment, or subcapsule, 326. That is, solid-shell cosmetic ingredient capsule 300 may include a compartment 326 that may include the active ingredient. The compartment 326 may be larger than coating 321 and may be configured to hold, contain, and/or include a larger amount (e.g., weight) of the active ingredient. The compartment 326 may comprise similar materials to active ingredient coating 321, and/or may include other materials that are configured to be waterproof, water-resistant, nonpolar, hydrophobic, and/or otherwise impervious to water. Thus, the compartment 326, protective coating 321, shell coating 324, and/or shell 302 may be configured to be the opposite polarity of personal care ingredient 318 (e.g., hydrophilic vs. hydrophobic, nonpolar vs. polar) so that they do not dissolve and/or otherwise break down when exposed to personal care ingredient 318.

When included in enclosed inner volume 316, active ingredient 320 may comprise at least 0.05%, at least 0.1%, at least 0.2%, at least 0.3%, at least 0.4%, at least 0.5%, at least 0.6%, at least 0.7%, at least 0.8%, at least 0.9%, at least 1%, at least 1.1%, at least 1.2%, at least 1.3%, at least 1.4%, at least 1.5%, at least 1.7%, at least 2%, at least 2.25%, at least 2.5%, at least 2.75%, at least 3%, at least 5%, at least 10%, at least 20%, at least 30%, at least 40%, at least 50%, at least 55%, at least 60%, at most 50%, at most 45%, at most 40%, at most 30%, at most 25% at most 20%, at most 15%, at most 10%, at most 5%, at most 4.5%, at most 4.25%, at most 4%, at most 3.75%, at most 3.5%, at most 3.25%, at most 3%, at most 2.75%, at most 2.5%, at most 2.25%, at most 2%, at most 1.75%, at most 1.5%, at most 1.25%, and/or at most 1% by weight of cosmetic material 317.

Personal care ingredient 318, when present, may be configured to serve as a base for cosmetic liquid 330 and/or a carrier for active ingredient 320. Thus, personal care ingredient 318 may be configured to be compatible for application to one or more of a user's skin, nails, hair, and/or other external body surfaces, but may not actively treat one or more skin, hair, and/or nail issues like, or may not treat to the same degree as, active ingredient 320. As examples, personal care ingredient 318 may include water, oil, one or more humectants, and/or combinations thereof and/or may include one or more thickening agents, emollients, emulsifiers, surfactants, and/or other elements that may modify the texture and/or viscosity of cosmetic liquid 330. Because the personal care ingredient 318 may include water and/or oil, personal care ingredient 318 may be configured to one or more of moisten, or moisturize, a user's skin, hair, nails, and/or other external body surfaces. As examples, the personal care ingredient may include one or more of a cream, water, oil, gel, serum, mousse, sunscreen, shampoo, conditioner, facemask, lipstick, blemish balm, pigment, emollient (stearyl alcohol), thickening agents (cetyl alcohol, xanthan gum) chemically inert substance (e.g., silica, silicone, dry water, etc.), surfactant, emulsifier, gelatin, and/or cellulose.

Personal care ingredient 318 may be in one or more phases, such as solid, liquid, and/or gas. When in liquid form, personal care ingredient 318 may include water, one or more humectants, one or more lipids, butters, oils, humectants, and/or combinations thereof. In some examples, personal care ingredient 318 may be water-based and/or may include water. Additionally or alternatively, personal care ingredient 318 may include water, but at least some and/or all of the water may be fully encapsulated in a coating, such as a silica-based coating (e.g., dry water). In other examples, personal care ingredient 318 may be lipid-based, such as oil-based and/or butter-based and may be lipophilic and/or may include lipids. Further, when personal care ingredient 318 comprises a liquid, it may include suspended solids, such as the microcapsule. Thus, the microcapsule and/or other solids may be suspended in the personal care ingredient, such as when personal care ingredient 318 is in liquid form. However, in other examples, personal care ingredient 318 may not include any water and/or may be completely anhydrous (i.e., 0% by weight water) and/or substantially anhydrous (i.e., at most 4%, at most 2%, and/or at most 1% by weight water). When personal care ingredient 318 and/or active ingredient 320 include liquid water, the cosmetic material may include a preservative. Additionally or alternatively, when personal care ingredient 318 and/or active ingredient 320 include water, cosmetic material 317 may include one or more humectants to lower the water activity of cosmetic material 317 below the threshold of permitting microbial growth, such as discussed herein. However, when the cosmetic material is substantially anhydrous and/or otherwise does not include liquid water, cosmetic material 317 and/or the entire solid-shell cosmetic ingredient capsule 300 may be free of preservatives. Additionally or alternatively, personal care ingredient 318 may include a solid phase. As an example, personal care ingredient 318 may include a dry powder.

When included in enclosed inner volume 316, personal care ingredient 318 may comprise at least 50%, at least 70%, at least 75%, at least 80%, at least 85%, at least 90%, at least 95%, at least 96%, at least 97%, at least 98%, at least 99%, at most 100%, at most 99%, at most 98%, at most 97%, at most 96%, at most 95%, at most 90%, at most 80%, at most 70%, and/or at most 60% by weight of cosmetic material 317.

As discussed above in the description of FIG. 1, solid-shell cosmetic ingredient capsule 300 may be sized and/or otherwise configured to fit and/or be received in cosmetic blending device 10, and more specifically, in bowl-shaped depression 64 of the base of cosmetic blending device 10. As examples, the solid-shell cosmetic ingredient capsule may have a total volume of at least 0.5 ml, at least 0.75 ml, at least 1.0 ml, at least 1.25 ml, at least 1.5 ml, at least 1.75 ml, at least 2 ml, at least 2.25 ml, at least 2.5 ml, at least 2.75 ml, at least 3 ml, at least 3.25 ml, at least 3.5 ml, at least 4 ml, at least 4.5 ml, at least 5 ml, at least 6 ml, at least 7 ml, at least 8 ml, at least 9 ml, at least 10 ml, at most 20 ml, at most 18 ml, at most 16 ml, at most 14 ml, at most 13 ml, at most 12 ml, at most 11 ml, at most 10 ml, at most 9 ml, at most 8 ml, at most 7 ml, at most 6 ml, at most 5 ml, at most 4 ml, and/or at most 3 ml. Enclosed inner volume 316 may comprise a volume of at least 0.4 ml, at least 0.5 ml, at least 0.6 ml, at least 0.7 ml, at least 0.8 ml, at least 0.9 ml, at least 1.0 ml, at least 1.25 ml, at least 1.5 ml, at least 1.75 ml, at least 2 ml, at least 2.25 ml, at least 2.5 ml, at least 2.75 ml, at least 3 ml, at least 3.25 ml, at least 3.5 ml, at least 3.75 ml, at least 4 ml, at least 4.5 ml, at least 5 ml, at most 10 ml, at most 9 ml, at most 8 ml, at most 7 ml, at most 6 ml, at most 5 ml, at most 4 ml, at most 3 ml, at most 2.5 ml, at most 2 ml, and/or at most 1.5 ml.

Shell 302 may comprise at least 40%, at least 42%, at least 44%, at least 45%, at least 46%, at least 47%, at least 48%, at least 49%, at least 50%, at least 60%, at least 65%, at least 70%, at least 75%, at least 80%, at least 85%, at most 90%, at most 85%, at most 80%, at most 75%, at most 70%, at most 60%, at most 58%, at most 56%, at most 55%, at most 54%, at most 53%, at most 52%, at most 51%, and/or at most 50% by weight of solid-shell cosmetic ingredient capsule 300. Cosmetic material 317 may comprise the remaining weight of the solid-shell cosmetic ingredient capsule. For example, the cosmetic material 317 may comprise at least 10%, at least 15%, at least 20%, at least 25%, at least 30%, at least 35% at least 40%, at least 42%, at least 44%, at least 45%, at least 46%, at least 47%, at least 48%, at least 49%, at least 50%, at most 60%, at most 58%, at most 56%, at most 55%, at most 54%, at most 53%, at most 52%, at most 51%, at most 50%, at most 45%, at most 40%, at most 35%, at most 30%, at most 25%, at most 20%, at most 15%, and/or at most 10% by weight of solid-shell cosmetic ingredient capsule 300. It should be appreciated that the percentage weight of the various components of the solid-shell cosmetic ingredient capsule relative to the entire weight of the solid-shell cosmetic ingredient capsule may be calculated based on their percentage weight in the shell and/or cosmetic material 317, since the total weight of the solid-shell cosmetic ingredient capsules may be equal to the sum of the weights of the cosmetic material and the shell. For example, when enclosed inner volume 316 only includes personal care ingredient 318 (i.e., where personal care ingredient 318 comprises 100% by weight of the cosmetic material 317 and/or the cosmetic material does not include active ingredient 320), the weight ratio of the shell to the personal care ingredient may be at least 2:3 and at most 3:2. In other embodiments, the weight ratio of the shell to the personal care ingredient may be 1:1, at least 0.8:1, at least 1.2:1, at least 1:2, at least 1:3, at least 1:4, at most 9:1, at most 8:1, at most 7:1, at most 6:1, at most 5:1, at most 4:1, at most 3:1, and/or at most 2:1.

As illustrated in FIG. 13, solid-shell cosmetic ingredient capsule 300 may include various combinations of the above described components. As illustrated in the eight examples of FIG. 13, shell 302 may include one or more of active ingredients 320, with and/or without active ingredient coating 321, lipids 305 (including one or more of fats 306 and waxes 308), resins 310, crystal promoters 312, chemically inert materials 314, and/or shell coating 324. Additionally or alternatively, enclosed inner volume 316 may include one or more of personal care ingredient 318, active ingredient 320 (with and/or without active ingredient coating 321), and/or compartment 326. Although eight different examples are illustrated showing various combinations of the above components, other combinations of the above components also are within the scope of the present disclosure, as discussed herein.

Solid-shell cosmetic ingredient capsule 300 may be configured to include an identity characteristic and/or the unique identifier that may identify the identity characteristic. As discussed above, the unique identifier may include a QR code, barcode, RFID tag, image, and/or any other identifying letter, number, image or indicia that may be recognized and/or read by cosmetic blending device 10. Thus, cosmetic ingredient capsule 300 may include one or more of a QR code, RFID tag, barcode, and/or other identifying letter, number, symbol, image, pattern, or other indicia. When included, the barcode, QR code, letter, number, symbol, image, pattern, and/or other indicia may be printed on the exterior of shell 302. The RFID tag, when included, may be embedded in shell 302 and/or coupled to the exterior surface of shell 302. As described above, the entirety of the solid-shell cosmetic ingredient capsule may be heated and/or blended to produce cosmetic liquid 330. Thus, in such examples, the unique identifier may be heated and/or blended and may become part of cosmetic liquid 330.

Solid-shell cosmetic ingredient capsule 300 may include one or more of decorations, designs, etchings, and/or other ornamentations that may be configured to increase the aesthetics of the solid-shell cosmetic ingredient capsule.

As described above, the contents of enclosed inner volume 316 may be confined, retained, secured, kept, and/or otherwise held within enclosed inner volume 316 by shell 302. However, when placed into cosmetic blending device 10 and heated and/or blended by cosmetic blending device 10, solid-shell cosmetic ingredient capsule 300 may be configured to transform (e.g., melt and/or mix) to cosmetic liquid 330. In particular, when heated to above its melting point and/or blended by cosmetic blending device 10, shell 302 may melt to a liquid and may mix with the contents of enclosed inner volume 316. In some examples, solid-shell cosmetic ingredient capsule 300 may require the heat and blending forces provided by cosmetic blending device 10 in order to transform to cosmetic liquid 330. For example, solid-shell cosmetic ingredient capsule 300 may not melt, blend, and/or form cosmetic liquid 330 when rubbed, squeezed, or otherwise manipulated by a user's hand. That is, friction and/or compressive forces applied by a user's hands alone may not be sufficient to form cosmetic liquid 330. As examples, shell 302 may be configured to withstand a compressive force of, and/or possess a compressive strength of, at least 33,000 $N/m^2$, at least 36,000 $N/m^2$, at least 39,000 $N/m^2$, at least 42,000 $N/m^2$, at least 45,000 $N/m^2$, at least 48,000 $N/m^2$, at least 51,000 $N/m^2$, at least 54,000 $N/m^2$, at least 57,000 $N/m^2$, at least 60,000 $N/m^2$, at least 63,000 $N/m^2$, at least 66,000 $N/m^2$, at least 69,000 $N/m^2$, at least 72,000 $N/m^2$, at most 110,000 $N/m^2$, at most 105,000 $N/m^2$, at most 100,000 $N/m^2$, at most 95,000 $N/m^2$, and/or withstand a crush force of, and/or possess a crush resistance of, at least at least 7 N, at least 7.5 N, at least 8 N, at least 8.5 N, at least 9 N, at least 9.5 N, at least 10 N, at least 11 N, at least 12 N, at least 13 N, at least 14 N, at most 14 N, at most 20 N, at most 21 N, at most 19 N, at most 18 N, at most 17 N, at most 16 N, at most 15 N, at most 14 N, at most 12 N, and/or at most 10 N.

As additional examples, solid-shell cosmetic ingredient capsule 300 may only form cosmetic liquid 330 when blended with a threshold rotational speed of at least 300 revolutions per minute (RPM), at least 350 RPM, at least 400 RPM, at least 450 RPM, at least 500 RPM, at most 1500 RPM, at most 1400 RPM, at most 1300 RPM, at most 1250 RPM, at most 1200 RPM, at most 1150 RPM, at most 1100 RPM, at most 1050 RPM, at most 1000 RPM, at most 950 RPM, at most 900 RPM, at most 800 RPM, and/or at most 750 RPM, such as while being heated above at least the melting point of the shell.

The physical properties of shell 302 that may permit solid-shell cosmetic ingredient capsule 300 to transform to cosmetic liquid 330 only when operated upon (i.e., heated and blended) within cosmetic blending device 10 (or to not form cosmetic liquid 330 when manually manipulated by a user's hand, such as by the user rubbing the capsule on the user's body or squeezing the capsule with the user's hand) may be afforded by at least one chemical component, or the combination of chemical components, that make up shell 302. As examples, shell 302 may include at least one lipid with a melting point of at least 40° C., and/or at least one lipid with a compressive strength of at least 51,000 $N/m^2$ and/or a crush resistance of 10 N. As another example, shell 302 may include one or more crystal promoters that may stabilize, increase the size of, and/or increase the amount of stable crystal domains within shell 302, which may strengthen, increase the crush resistance of, and/or increase the melting point of shell 302 relative to an equivalent shell composition that does not include the one or more crystal promoters, and/or such that shell 302 only transforms to cosmetic liquid 330 when operated upon by cosmetic blending device 10.

Additionally or alternatively, shell 302 may include a physical structure, a chemical microstructure, and/or a crystal structure that is configured to permit solid-shell cosmetic ingredient capsule 300 to transform to cosmetic liquid 330 only when operated upon by cosmetic blending device 10. For example, as discussed in more detail herein, shell 302 may be prepared by a method that includes one or more processing steps that strengthen, or increase the melting point of, shell 302 by producing stable crystal types, stable crystal phases, and/or a strengthened extended structure within shell 302. As examples, shell 302 may be a heat-treated shell, such as a tempered shell, a conditioned shell, and/or a tempered and conditioned shell. As discussed in more detail herein, in such examples, the one or more components, or mixture thereof, that make up shell 302 may have been subjected to a heat-treating process, such as a tempering process, a conditioning process, and/or a combination thereof, during production of shell 302. Such process(es) may strengthen shell 302 and/or increase the melting point of shell 302. In some instances, a heat-treated shell, a tempered shell, a conditioned shell, and/or a tempered and conditioned shell may possess a greater melting point, a higher compressive strength, and/or a lower solubility or rate of dissolution in water or the cosmetic material 317 relative to an otherwise equivalent shell (i.e., a shell that includes the same chemical components and is prepared according to an otherwise equivalent method) that is not tempered, conditioned, and/or tempered and conditioned. As discussed above in the description of FIG. 1, because the solid-shell cosmetic ingredient capsule 300 may not include any packaging, wrapping, and/or lining when it is placed into cosmetic blending device 10, the entirety of the solid-shell cosmetic ingredient capsule 300, including the shell 302 and at least one of the personal care ingredient 318 and the active ingredient 320, may form cosmetic liquid 330. Cosmetic liquid 330 thus will be in a liquid phase when produced by the cosmetic blending device. In some examples, cosmetic liquid 330 may be warm to a user's touch when produced by cosmetic blending device 10, such as at room temperature or warmer than room temperature (i.e., warmer than ~22° C.) or warmer than a user's body temperature (37° C.). Additionally or alternatively, cosmetic liquid 330 may be frothy when produced by the cosmetic blending device, as discussed herein.

However, even in a liquid phase, cosmetic liquid 330 optionally may be designed to still contain suspended solids. For example, when shell 302 comprises wax beads (e.g., jojoba wax beads), the wax beads may remain in a solid phase, even after heating and blending in cosmetic blending device 10. Thus, cosmetic blending device 10 may not be configured to melt all of solid-shell cosmetic ingredient capsule 300. That is, some components of solid-shell cosmetic ingredient capsule 300 may be selected to have melting temperatures that are higher than the maximum blending temperature of cosmetic blending device 10. Such suspended solids may provide a desired texture and/or feeling to a user, and/or may encourage exfoliation.

As defined herein, cosmetic liquid 330 may be described as forming an at least substantially homogenous mixture when the cosmetic liquid comprises suspended solids, emulsions, foams and/or other phase-separated mixtures. In such a case, however, the heating and blending of cosmetic liquid 330 may evenly distribute the suspended solids, emulsions, foams, and/or other phase-separated components evenly throughout cosmetic liquid 330. In other words, cosmetic liquid 330 may be at least substantially homogeneous and possess an at least substantially even or consistent composition of phase-separated components. Additionally, when cosmetic liquid 330 comprises suspended solids, the suspended solids may have at least substantially similar particle sizes or a narrow range of particle sizes such that the mixture comprises an at least substantially homogenous distribution and/or composition of the suspended solids.

Shell 302 and/or cosmetic material 317 may be configured or formulated to produce a cosmetic liquid 330 that remains stable or is a stable liquid mixture subsequent to heating and blending within blending device 10, such as for at least a threshold duration of time. More specifically, shell 302 and/or cosmetic material 317 may be configured or formulated such that cosmetic liquid 330 remains a liquid, remains flowable, and/or does not at least partially, or completely, harden (or reharden), such as for at least the threshold duration of time. Additionally or alternatively, shell 302 and/or cosmetic material may be configured and/or formulated such that cosmetic liquid 330 does not separate, sediment, or crystalize such as for at least the threshold duration of time. For example, shell 302 and/or cosmetic material 317 may be formulated to produce a cosmetic liquid that has a lower melting point, or melting point range, than shell 302. As a more specific example, humectants, water, emulsifiers, and solubilizing lipids and/or fats may be added to cosmetic material 317 and/or shell 302 to prevent cosmetic liquid 330 from (re)hardening or reduce the rate of (re)hardening subsequent to being produced, such as in blending device 10.

Additionally or alternatively, the lipids that comprise shell 302 and the lipids that comprise the cosmetic material 317 may be selected to be compatible with one another, prevent recrystallization of the shell material(s) within the cosmetic liquid, and/or prevent oil migration within the cosmetic liquid, such as at least for the threshold duration of time. As a more specific example, when cosmetic material 317 is anhydrous, or lipid-based, hydrogenated triglycerides, softened fats, and various other triglycerides and lipids, such as the same butters and/or triglycerides that make up shell 302, may be added to cosmetic material 317 to prevent cosmetic liquid 330 from separating, such as for at least the threshold duration of time. Examples of the threshold duration of time include at least 5 minutes, at least 10 minutes, at least 30 minutes, at least 1 hour, at least 3 hours, at most 1 hour, at most 5 hours, at most 10 hours, at most 1 day, and/or at most 7 days.

Cosmetic blending device 10 and solid-shell cosmetic ingredient capsule 300, or a kit comprising a plurality of solid-shell cosmetic ingredient capsules, may be referred to as a system, or a cosmetic blending system, that is configured to store and provide the cosmetic liquid to a user. Similarly, cosmetic liquid 317 and solid-shell cosmetic ingredient capsule 300 collectively may be referred to as a cosmetic article or a cosmetic product that has a first state in the form of solid-shell cosmetic ingredient capsule 300, and a second state in the form of cosmetic liquid 330. The first state additionally or alternatively may be referred as a storage state, a cosmetic liquid precursor state, an unblended state, and/or a handling state. The second state additionally or alternatively may be referred to as a heated and blended state, a liquid state, and/or a ready-to-use state. FIGS. 14 and 15 illustrate examples of methods according to the present disclosure. In particular, FIG. 14 illustrates examples of methods 400 that may be performed by a user to operate and/or use cosmetic blending device 10 to prepare and/or apply cosmetic liquid 330 from at least one solid-shell cosmetic ingredient capsule 300. FIG. 15 illustrates examples of methods 450 that may be performed to form and/or manufacture solid-shell cosmetic ingredient capsule 300.

To operate a cosmetic blending device (e.g., cosmetic blending device 10) a user optionally may open a blending chamber (e.g., blending chamber 100) of the device at 402. In particular, a user may adjust a lid (e.g., lid 20) and a base (e.g., base 60) of the device to an open position to provide access to the blending chamber. A user may open the blending chamber by moving the lid relative to the base. As examples, a user may rotate, translate, and/or pivot the lid relative to the base. In some examples, the opening the blending chamber may include decoupling the lid from the base.

At 404, a user may place a capsule (e.g., solid-shell cosmetic ingredient capsule 300) into the blending chamber. As described previously, the user may place the capsule in a bowl-shaped depression (e.g., bowl-shaped depression 64) of the base. Optionally, the user may place the capsule into a cosmetic ingredient receptacle (cosmetic ingredient receptacle 150) that may line the bowl-shaped depression and/or may be selectively removed from bowl-shaped depression. The user may insert a single capsule in the blending chamber, or may place more than one capsule in the blending chamber, such as two, three, four, and/or five capsules in the blending chamber. A user optionally may utilize the cosmetic blending device to prepare cosmetic liquid 330 and subsequently add another solid-shell cosmetic ingredient capsule 300 and/or other ingredient to the blending chamber and then repeat or perform a different blending cycle to form a modified cosmetic liquid.

A user may close the blending chamber at 406. In particular, the closing the blending chamber may comprise adjusting the lid and the base to the closed position. As discussed previously, this may include rotating, translating, and/or pivoting lid 20 relative to base 60. The closing the blending chamber optionally may comprise crushing the capsule at 408. In particular, when adjusting the lid and the base to the closed position, a blending element (e.g., blending element 22) of the lid may crush the capsule. The crushing may include squashing, crushing, breaking, and/or otherwise deforming the capsule. In particular, the crushing may include crushing a shell (e.g., shell 302) of the capsule to permit leakage and/or spillage of a cosmetic material (e.g., cosmetic material 317) to the bowl-shaped depression.

Optionally at 410, methods 400 may include identifying a characteristic and/or identity of the capsule. As discussed, the physical characteristic and/or identity characteristic of the capsule may be identified by a controller (e.g., controller 172) based on input from the user and/or based on measured parameters. For example, the controller may determine a weight of the capsule via a weight sensor and/or may determine an identity characteristic of the capsule based on a unique identifier (e.g., RFID tag, barcode, etc.) of the capsule. Additionally or alternatively, a user may input one or more characteristics of the capsule via a user input device (e.g., user input device 210).

At 412, methods 400 may include heating and blending the capsule to produce a cosmetic liquid (e.g., cosmetic liquid 330). In particular, methods 400 optionally may include initiating the heating and blending at 414. As discussed, the heating and blending may be initiated by a user via input from user input device 210 and/or may be initiated autonomously by the controller based on sensed conditions (e.g., the lid and the base being adjusted to the closed position and the capsule being positioned in the bowl-shaped depression). During the heating and blending, methods 400 optionally may include adjusting the heating and blending. As described, the controller may adjust the heating and blending, as indicated at 416, based on feedback from one or more sensors. For example, the controller may reduce electric power to a thermal element (e.g., thermal element 110) when the sensed temperature is too hot (greater than a threshold/set point or range) and/or increase electric power to the thermal element when the sensed temperature is too low (lower than a threshold/set point or range). As another example, controller 172 may increase electric power to an electric motor (e.g., electric motor 121) when a rotational speed of the electric motor and/or the blending element is too low and/or when a measured static torque applied to the blending element is too high (greater than a threshold/set point or range) and/or decrease electric power to the electric motor when the rotational speed of the electric motor and/or the blending element is too high and/or when the measured static torque on the blending element is too low (less than the threshold/set point or range). As described, the heating and blending process may be referred to as a blending cycle.

Additionally or alternatively, the set points/thresholds may be adjusted throughout the course of a blending cycle such that the heating and/or blending during a blending cycle may not be uniform and/or may vary throughout the course of the blending cycle. In some examples, and as described above, at the beginning of a blending cycle, only heating may be performed and the drive mechanism may be powered off. Additionally or alternatively, when the drive mechanism is powered on (e.g., after the initial heating-only period), the speed of the drive mechanism may be gradually increased in power until it reaches a maximum rotational speed. Additionally or alternatively, at the end of a blending cycle, the drive mechanism may be powered off and cooling may be performed before the blending cycle terminates.

When the heating and blending is complete, and the cosmetic liquid has been produced (the capsule has been melted and blended to form a homogenous liquid mixture), the blending cycle may be over. The user optionally may open the blending chamber at 418 and apply the cosmetic liquid at 420. For example, the user may apply the cosmetic liquid to one or more of the user's skin, hair, and/or nails.

Methods 400 may include adding one or more auxiliary cosmetic materials to personalize cosmetic liquid 330. As examples, the one or more auxiliary cosmetic materials may include one or more liquids, powders, and/or oils that may be configured to add a desired effect to cosmetic liquid 330, such as to add and/or change a pigmentation, texture, viscosity, fragrance, etc., of cosmetic liquid 330. In some examples, the auxiliary cosmetic materials may include one or more of a pigment, dye, and/or fragrance. One specific example of an auxiliary cosmetic material includes dry water. The one or more auxiliary cosmetic materials may be added to the blending chamber by a user before the heating and blending (e.g., such as at 404 when a user places a capsule into the blending chamber) and/or after the heating and blending (e.g., such as when the user opens the blending chamber to reveal cosmetic liquid 330 at 418, but before the user extracts the cosmetic liquid).

Turning to methods 450, at 451, the methods 450 may comprise forming a portion of the shell. Forming the portion of the shell optionally includes preparing a liquid shell material at 452 (e.g., melting the components of shell 302), tempering the liquid shell material at 454, and/or dispensing the liquid shell material into a mold at 456. Preparing the liquid shell material may include melting the components of the shell (e.g., fats 306, waxes 308, resins 310, crystal promoters 312, chemically inert materials 314, and/or active ingredient 320) and blending them together in a vat or other container. In some examples, the active ingredient may be melted and blended together with the other components prior to the dispensing. Additionally or alternatively, the active ingredient may be added after the liquid shell material is dispensed into the mold at 456, as discussed below with respect to step 460. As the melted shell material will solidify to form the solid shell of a solid-shell cosmetic ingredient capsule, liquid shell material additionally or alternatively may be referred to as melted shell material and/or liquefied shell material.

Methods 450 may include forming a stable crystal structure from the liquid shell material, which may include promoting, facilitating, initiating, and/or selecting for desired crystal growth and/or crystal formation within the liquid shell material, and/or promoting, facilitating, initiating, and/or creating stable interfacing or interconnection between crystal domains within the liquid shell material and/or the solidified liquid shell material. The forming the stable crystal structure may include increasing the melting point of the shell, the compressive strength of the shell, and/or the crush resistance of the shell and/or decreasing the solubility of the shell in water and/or in the cosmetic material, and/or decreasing the dissolution rate (the kinetic parameter) of the shell in water and/or in the cosmetic material.

As examples, the forming the stable crystal structure from the liquid shell material may include increasing the melting point of the shell to be any of the shell melting points discussed herein. As more examples, the forming the stable crystal structure may include increasing the compressive strength or crush resistance of the shell to be any of the shell compressive strengths or crush resistances discussed herein. In some examples, the forming the stable crystal structure comprises forming a shell that possesses a sufficiently high melting point, compressive strength, and/or crush resistance, and/or a sufficiently low water solubility, low solubility in the cosmetic material, and/or low dissolution rate in the cosmetic material and/or water such that the shell only melts, dissolves, substantially deforms, and/or forms the cosmetic liquid when operated upon by cosmetic blending device 10, and/or when operated upon according to methods 400.

As referred to herein, a particular method step that "increases," or "decreases" a physical property of the shell may refer to the physical property being increased or decreased relative to an otherwise equivalent shell. Further as referred to herein, an "otherwise equivalent shell" may be described as a shell that is formed from the same chemical components and prepared according to an otherwise equivalent method that does not include the particular method step.

In some examples, the forming the stable crystal structure may include heat treating the liquid shell material, which may include tempering the liquid shell material at 454. Tempering the liquid shell material may include repeatedly alternating between heating and cooling the liquid shell material, and optionally stirring during the heating and cooling the liquid shell material. Tempering the liquid shell material may facilitate or initiate formation of desired crystal phases and/or crystal types, while consuming undesirable crystal phases and/or crystal types that may be formed during the initial cooling. Stated differently, tempering may include selectively forming one or more desired crystal phases and/or crystal types in the solidified liquid shell material. Tempering the liquid shell additionally or alternatively may include precluding the formation of one or more undesired crystal phases and/or crystal types in the solidified liquid shell material. In other words, the tempering may include melting out the one or more undesired crystal phases and/or crystal types (e.g., by heating the liquid shell material to above the melting point of the one or more undesired crystal phases and/or crystal types) and forming the desired crystal phases and/or crystal types from the melted undesired crystal phase(s) and/or crystal type(s). With this in mind, the tempering also may include increasing the crystal size of the one or more desired crystal phases and/or crystal types. In some examples, the one or more desired crystal phases and/or crystal types selectively formed during the tempering are more stable or more thermodynamically favored than the one or more undesired crystal phases and/or crystal types.

In view of the above, the tempering the liquid shell material is performed to form a stable crystal structure from the liquid shell material, which may include increasing the melting point of the shell, increasing the compressive strength of the shell, decreasing the solubility of the shell in water and/or in the cosmetic material, and/or decreasing the dissolution rate of the shell in water and/or in the cosmetic material. Stated differently, at least for some shell compositions, the shell produced by methods 450 that include the tempering may include a higher melting point, a greater compressive strength, a lower water solubility, a lower dissolution rate in water, a lower solubility in the cosmetic material, and/or a lower dissolution rate in the cosmetic material relative to an otherwise equivalent shell. As discussed, such an otherwise equivalent shell means a shell that consists of the same shell composition and is formed by an otherwise equivalent method, but which is not tempered and may include the undesirable crystal phases or types.

The tempering the liquid shell material at 454 may be performed for shell compositions that may not form stable crystal structures or desired crystal phases when cooled directly from a liquid. As examples, the tempering at 454 may be performed for shell compositions that include, or are primarily, at least substantially, or completely formed from individual triglycerides, triglyceride blends, butters that are low in lauric-based fats or that do not include lauric acid, shea butter, Illipe butter, mango butter, and/or Kokum butter.

Additionally or alternatively, the forming the stable crystal structure may include adding, incorporating, or including crystal promoters and/or crystal stabilizers to the liquid shell material to facilitate, enhance, and/or promote the formation of the one or more desired crystal phases within the liquid shell material, to stabilize the one or more desired crystal phases within the liquid shell material, and/or to form a stable crystal structure within and/or from the liquid shell material. With this in mind, incorporating the crystal promoters and/or crystal stabilizers may include increasing the melting point of the shell, increasing the compressive strength or crush resistance of the shell (such as to be greater than that of an otherwise equivalent shell that does not include the crystal promoters and/or crystal stabilizers), and/or decreasing the solubility of and/or decreasing the dissolution rate of the shell in water and/or the cosmetic material to be less than that of an otherwise equivalent shell that does not include the crystal promoters and/or crystal stabilizers. The incorporating the crystal promoters and/or crystal stabilizers may be performed during the preparing at 452, prior to the tempering at 454, prior to the conditioning at 455, at least substantially simultaneously with the tempering at 454, at least substantially simultaneously with the conditioning at 455, and/or prior to the dispensing at 456.

Methods 450 additionally or alternatively may include conditioning the liquid shell material at 455. The conditioning at 455 may be performed for shell compositions that form a stable crystal structure readily when cooled directly from a liquid, do not require tempering to form a stable crystal structure, and/or form a stable crystal structure quickly upon cooling directly from the liquid shell material. As more specific examples, the conditioning at 455 may be performed for shell compositions that include, or are primarily, at least substantially, or completely formed from waxes, hydrogenated fats, partially hydrogenated fats, hydrogenated oils, partially hydrogenated oils, unsaturated oils, unsaturated fats, lauric acid-based triglyceride blends, lauric acid-based triglyceride butters, lauric acid-based triglyceride oils, palm oil, and/or coconut oil.

The conditioning the liquid shell material at 455 may include maintaining the liquid shell material at a conditioning temperature, optionally while stirring the liquid shell material, monitoring the liquid shell material to detect the formation of crystals within the liquid shell material, and cooling and/or dispensing the liquid shell material into the mold once a desired quantity, concentration, and/or composition of crystals are detected in the liquid shell material. As an example, the monitoring the liquid shell material may include monitoring or measuring the viscosity of the liquid shell material during the maintaining the liquid shell material at the conditioning temperature.

The conditioning temperature may be selected based upon the melting point or melting point range of the shell material. As examples, the conditioning temperature may be within the melting point range of the shell material, at the lower end of the melting point range of the shell material, and/or at least 0.5° C. below, at least 1° C. below, at least 2° C. below, at least 3° C. below, at least 4° C. below, at least 5° C. below, at least 6° C. below, at least 7° C. below, at least 8° C. below, at least 9° C. below at least 10° C. below, at most 1° C. below, at most 2° C. below, at most 3° C. below, at most 4° C. below, at most 5° C. below, at most 6° C. below, at most 7° C. below, at most 8° C. below, at most 9° C. below, at most 10° C. below, at most 20° C. below, and/or at most 30° C. below the melting point or the lower end of the melting point range of the shell material.

The conditioning at 455 may be performed such that the liquid shell material may be solidified to produce a desired shell thickness and/or a stable or strengthened extended structure during the dispensing at 456 and/or during the cooling and hardening at 464. More specifically, the conditioning at 455 may facilitate or initiate the formation of stabilizing interactions between and/or stable interfacing between discrete crystal domains within the shell material during the dispensing at 456 and/or the cooling and hardening at 464. In other words, the conditioning at 455 may be performed to impart desired physical or microstructural properties on the liquid shell material, such as a desired viscosity or desired temperature, for forming the shell therefrom. As examples, without the conditioning at 455, the liquid shell material solidified from too high or too low of a temperature may possess a weakened crystalline lattice or extended structure if stresses are applied during the solidification and/or may possess an undesirable thickness. Thus, the conditioning at 455 also may include increasing the compressive strength and/or crush resistance of the shell.

The conditioning the liquid shell material and/or the tempering the liquid shell material may be performed prior to, or at least substantially simultaneously with the dispensing the liquid shell material at 456.

As referred to herein, the liquid shell material may be completely liquid, liquefied, or only comprise melted or liquid shell materials. As indicated above, the liquid shell material alternatively may include one or more solids, such as the crystals discussed herein or insoluble shell ingredients discussed herein, which may be evenly or stably dispersed in the liquefied shell materials, such that the liquefied and solid shell materials may flow and/or possess a desired viscosity.

A shell formed according to methods 450 that comprise the tempering at 454 and/or the conditioning at 455 may be referred to as a heat-treated shell. A shell formed according to methods 450 that include the tempering at 454 may be referred to as a tempered shell. A shell formed according to methods 450 that include the conditioning at 455 may be referred to as a conditioned shell, and a shell formed according to methods 450 that include the conditioning at 455 and the tempering at 454 may be referred to as a tempered and conditioned shell.

Dispensing the liquid shell material at 456 may include injecting, pouring, and/or otherwise dispensing the liquid shell material into the mold. The mold may include a plurality of depressions configured to produce a plurality of the capsules at a time. The dispensing may include dispensing the liquid shell material into all of the depressions simultaneously, or sequentially dispensing the liquid shell material into a predetermined number (i.e., a subset) of the depressions until all of the depressions are filled with the liquid shell material. In some examples, the forming the portion of the shell additionally or alternatively may include hardening, solidifying, and/or otherwise cooling the liquid shell material after it has been poured into the mold.

More specifically, the dispensing at 456 may include solidifying and/or hardening at least a portion of the dispensed liquid shell material along the walls or the surfaces of the mold until a desired thickness of the shell material is solidified along the walls or inner surfaces of the mold. The dispensing at 456 subsequently may include removing the remaining or unsolidified portion of the dispensed liquid shell material from within the mold and/or from within the solidified shell material. In this way, the dispensing at 456 may include forming a shell with the desired shell thickness, such as discussed herein. A properly conditioned and/or tempered shell may spontaneously separate from the mold after the liquid shell material is solidified, and/or during the cooling and hardening at 464.

Alternatively, the dispensing at 456 may include dispensing the liquid shell material into the mold, positioning an auxiliary mold member into the mold to displace a desired volume and/or a desired shape of liquid shell material from within the mold, and solidifying the liquid shell material with the auxiliary mold member positioned within the mold. The auxiliary mold member may be dimensioned and/or shaped relative to the mold such that dispensing produces the shell portion with the desired shell thickness and/or internal shape. At 460, methods 450 include adding a cosmetic material (e.g., cosmetic material 317) to the portion of the shell. The cosmetic material may be poured, injected, and/or otherwise dispensed into the portion of the shell formed at 451. The cosmetic material may be added in any suitable state, including a liquid state, semi-liquid state, and/or solid state. An example of a solid state is a frozen state, such as if the cosmetic material is preformed into a desired size and shape and then frozen prior to being inserted or otherwise added to the portion of the shell. Further, the adding the cosmetic material may include adding the personal care ingredient and/or the active ingredient into all of the shell portions concurrently (at the same time), or sequentially adding the personal care ingredient and/or active ingredient into a predetermined number (i.e., a subset) of the shell portions until all of the shell portions are filled with, or filled with a predetermined amount of, the personal care ingredient and/or active ingredient.

As described, the active ingredient also may be added to the portion of the shell at 460. In some examples, the active ingredient may be added to all of shell portions in the mold. However, in other examples, the active ingredient may be added to only a subset of the shell portions in the mold. Additionally or alternatively, the same and/or different amounts of the active ingredient may be added to the shell portions for which active ingredients are added. In this way, some of the shell portions may not include any of the active ingredient, and even the shell portions that include the active ingredient may include varying concentrations and/or amounts of the active ingredient. However, in other examples, the same amount of the active ingredient may be added to all of the shell portions. The active ingredient may be added concurrently with the personal care ingredient, or sequentially before or after the personal care ingredient.

At 462, the methods 450 include forming the remaining portion of the shell. The remaining portion of the shell may be a bottom portion of the shell. Thus, the portion of the shell formed at 451 may include a top and sidewalls that are sufficient to hold the cosmetic material, and the remaining portion may be a bottom portion of the shell. Other options are within the scope of the present disclosure, such as in which the portion formed at 451 includes a bottom and sidewalls, and with the remaining portion being a top portion of the shell. The remaining portion of the shell may cover the cosmetic material and/or fully enclose and fluidly seal the cosmetic material. The remaining portion of the shell may be formed in the same and/or similar manner to the portion of the shell at 451. The forming the remaining portion of the shell also may include forming a plurality of additional shell portions which may be joined with the portion of the shell to form the remaining portion of the shell. Stated differently, the forming at 451 may include forming a first portion of the shell, and the forming at 462 may include forming at least a second portion of the shell, and optionally a plurality of additional portions that form the remainder of the shell.

The forming the remaining portion of the shell may include interconnecting the portion of the shell formed at 451 with the remaining portion of the shell formed at 462, which may include fluidly sealing and/or enclosing the interior of the shell and/or fluidly isolating and/or enclosing the cosmetic material added to the interior of the portion of the shell at 460.

Methods 450 optionally include cooling and/or hardening the shell at 464. The cooling and/or hardening may include actively cooling the shell, such as with a refrigerator or other refrigerating device, and/or passively cooling the shell, such as by leaving the shell to cool at ambient (i.e., room) temperature. The cooling and/or hardening at 464 and/or the tempering at 454 may include forming crystals in the shell. Forming crystals in the shell may shrink the shell slightly, which may help release the shell from the mold at 466.

At 466, methods 450 may include removing the solid-shell cosmetic ingredient capsule from the mold. Methods 450 may include forming a unique identifier on the capsule and/or decorating the capsule at 468. Decorating may include etching images and/or designs on the surface of the capsule, and/or coupling auxiliary decorations to the outside of the capsule (e.g., ribbons, glitter, etc.). Additionally or alternatively, the forming at 468 may be performed during the dispensing at 456. As more specific examples, unique identifiers may be embossed and/or debossed in the mold to create an opposite effect on the shell (e.g., a mold that is embossed would create raised features on the shell and vice versa). Utilizing a mold with embossed and/or debossed features may allow the shell thickness to be selectively varied across the shell, such that specific areas of the shell may be provided with a greater thickness to selectively strengthen the shell.

As described, when the unique identifier comprises a barcode, QR code, or other optical indicia, forming the unique identifier may comprise printing, etching, or otherwise impregnating the unique identifier on the surface of the capsule. In some such examples, the unique identifier may include pigmented shell material. When the unique identifier comprises an RFID tag or other electromagnetic tag, the forming the unique identifier may comprise inserting and/or implanting the unique identifier into the capsule and/or otherwise coupling the unique identifier to the capsule. At 470, methods 450 optionally include packaging the capsule in packaging (e.g., packaging 340). One or more (e.g., a plurality) of the capsules may be packaged together in the packaging to form a kit (e.g., kit 290), as will be described in greater detail herein. The kit may include varying proportions of capsules having the active ingredient (e.g., 100%, 50%, 25%, etc., of the capsules may include the active ingredient) and/or capsules having varying concentrations of the active ingredient (i.e., of the capsules in the kit that include the active ingredient, some may include higher or lower concentrations of the active ingredients than others).

As illustrated in FIG. 12, one or more of the solid-shell cosmetic ingredient capsules may be packaged together in packaging 340 to form a kit 290. Thus, kit 290 may include packaging 340 and one or more solid-shell cosmetic ingredient capsules 300. Kit 290 may be configured to provide a regimented dosage schedule for active ingredient 320. Kit 290 may also be referred to as cosmetic kit 290, capsule-containing kit 290, tolerance building kit 290, and/or dosage scheduler 290. Packaging 340 may be configured to receive, contain, support and/or otherwise hold a single solid-shell cosmetic ingredient capsule 300 or a plurality of solid-shell cosmetic ingredient capsules 300. As an example, and as illustrated in FIG. 12, in addition to solid-shell cosmetic ingredient capsule 300, packaging 340 may include a second solid-shell cosmetic ingredient capsule 300, a third solid-shell cosmetic ingredient capsule 300, etc.

However, the packaging may include more than three solid-shell cosmetic ingredient capsules in other examples. In particular, the packaging 340 may be configured to include at least two solid-shell cosmetic ingredient capsules 300, at least four solid-shell cosmetic ingredient capsules 300, at least six solid-shell cosmetic ingredient capsules 300, at least eight solid-shell cosmetic ingredient capsules 300, at least twenty solid-shell cosmetic ingredient capsules 300, and/or at least thirty solid-shell cosmetic ingredient capsules 300. As further examples, the packaging may include a week's, two weeks', or a month's supply of solid-shell cosmetic ingredient capsules 300 (e.g., 7, 14, or 28, 29, 30 and/or 31 solid-shell cosmetic ingredient capsules for a one-a-day dosage).

Capsules 300 may be precisely arranged and/or ordered in packaging 340, or capsules 300 may be randomly positioned within packaging 340. As examples, capsules 300 may be arranged in rows and/or columns in packaging 340. Additionally or alternatively, packaging 340 and/or capsules 300 may include numbering or other ordering schemes that are configured to indicate to a user the order in which to utilize the capsules of packaging 340 and/or a frequency with which to consume the capsules (e.g., one a day, two a day, three a day, etc.).

Packaging 340 may include the unique identifier of capsule 300 and/or other identity and/or physical characteristics of the capsules in packaging 340.

As described above, packaging 340 may include multiple capsules 300 to form kit 290. Kit 290 may include at least one kit 290, at least two kits 290, at least three kits 290, at least four kits 290, at least five kits 290, and/or at least six kits 290. When kit 290 includes more than one kit, the kits may be referred to as regimented dosage scheduler 290. Additionally or alternatively, when kit 290 includes more than one kit, the kits may be packaged together or separately. In some examples, one kit 290 may comprise a single discrete packaging 340, such that different kits 290 are physically distinct packages. Additionally or alternatively, capsules 300 may be included in packaging 340 of each kit 290 in different orders, combinations, numbers, and/or types to form different kits 290. As an example, the capsules in different kits 290 may include different dosages of the active ingredient. In this way, a user may increase their intake of the active ingredient by purchasing kits 290 including capsules 300 having increasingly higher dosages of the active ingredient and/or by purchasing kits 290 containing a greater number of capsules that include the active ingredient (so that the user applies the active ingredient more frequently).

Thus, kit 290 may be configured to provide a regimented dosage schedule for active ingredient 320. In some examples, the concentration of active ingredient 320 in each kit 290 may be different. As one such example, a first kit may include a lower first concentration of the active ingredient, a second kit may include an intermediate second concentration of the active ingredient, and a third kit may include a higher third concentration of the active ingredient. However, in other examples, kits 290 may include more or less than three tiers of active ingredient concentrations. For example, a set of kits 290 designed for monthly use may include four kits 290, one for each week of the month. A user may first consume the solid-shell cosmetic ingredient capsules of the first kit containing the lower first concentration of the active ingredient, and after finishing the solid-shell cosmetic ingredient capsules of the first kit, then may transition to using the second kit containing the intermediate second concentration of the active ingredient, and then after finishing the solid-shell cosmetic ingredient capsules of the second kit, may transition to using the third kit containing the higher third concentration of the active ingredient. In this way, a user may build up the user's tolerance to the active ingredient over time, and the user may periodically increase the dosage of the active ingredient by purchasing kits 290 containing increasingly higher concentrations of the active ingredient. Thus, kits 290 may provide a regimented dosage schedule that may allow a user to gradually increase or decrease the dosage of the active ingredient over time. For example, capsule 300 with retinol, acne medication (e.g., salicylic acid), steroids, or another prescription ingredient as an active ingredient may be packaged in such a manner. Additionally or alternatively, the kits may permit a user to taper off an active ingredient by, for example, purchasing kits having successively lower dosages of the active ingredient. As an illustrative example, a kit containing salicylic acid (SA) and/or retinol may include solid-shell ingredient capsules containing 0.5-2% SA and/or 0.025-3% retinol, by weight, with a subsequent kit in a series of kits optionally including greater concentrations of SA and/or retinol than a prior kit in the series, (with some of the capsules not having any SA and/or retinol, and instead configured to calm the skin), and with the last kit in the series optionally including the same or a lower concentration of SA and/or retinol than the first kit in the series.

Additionally or alternatively when kit 290 contains one or more capsules 300 having the active ingredient, not all of the capsules in the kit may contain the active ingredient, and/or the capsules in the kit may contain different concentrations of the active ingredient. Thus, not all of the capsules in kit 290 may contain the active ingredient. Stated slightly different, the capsules containing the active ingredient may be spaced out in a kit, with capsules devoid of the active ingredient (i.e., active-free capsules) interspersed in-between the active-containing capsules. Thus, kit 290 may include one or more of a first subset of capsules that contain the active ingredient, a second subset of capsules that do not contain the active ingredient, and/or a third subset of capsules that contain a different active ingredient than the first subset of capsules.

When active-free capsules are included in kit 290, these active-free capsules may be configured to minimize and/or mitigate the side effects of the active ingredient. In particular, they may be configured to nourish, hydrate, calm, replenish, moisturize, soothe, and/or otherwise provide a break from the active ingredient. In this way, the kits may help a user build up a tolerance to the active ingredient, while minimizing the side effects of the active ingredient. For example, if kit 290 contains an active ingredient that may cause redness, dryness, or irritation of a user's skin, such as may be caused by retinol and/or some acne medicines, a kit may include a series of solid-shell cosmetic ingredient capsules that include this active ingredient, and one or more solid-shell cosmetic ingredient capsules that do not include this active ingredient. As a further example, the solid-shell cosmetic ingredient capsule(s) may include different active ingredients that may be configured to calm, reduce inflammation, reduce redness, hydrate the user's skin, and/or otherwise offset the side effects of the other active ingredients.

As examples, at least 10%, at least 15%, at least 20%, at least 25%, at least 30%, at least 35%, at least 40%, at least 50%, at least 75%, at most 100%, at most 80%, at most 75%, at most 70%, at most 65%, at most 60%, at most 55%, at most 50%, at most 45%, at most 40%, at most 35%, and/or at most 30% of the capsules in kit 290 may not include the active ingredient. When the kit includes a mixture of active-ingredient-containing capsules and active-free capsules, the capsules may be arranged and/or ordered in an alternating pattern/order. That is, the active-free capsules may be interspersed between the capsules containing the active ingredient. In particular, the capsules containing the active ingredient may be spaced apart from one another at regular intervals in packaging 340 by the capsules not containing the active ingredient. As examples, the capsules containing the active ingredient may be every second, every third, every fourth, every fifth, and/or every sixth capsule in packaging 340. In between each active-ingredient-containing capsule 300, a cleansing capsule and/or a calming capsule may be included. These capsules not containing the active ingredient may include only personal care ingredient 318. Thus, different capsules that serve different purposes and/or provide different desired effects may be included within the same kit. By including capsules without the active ingredient in between the capsules with the active ingredient (i.e., by spacing out the capsules with the active ingredient), undesirable side effects of the active ingredient may be reduced, providing a more soothing, less irritating user experience if the particular active ingredient has a propensity for causing an undesirable side effect.

In some such examples, the capsules of a given kit having the active ingredient may comprise at least approximately the same concentration of the active ingredient. Specifically, the relative concentrations of active ingredient 320 in the solid-shell cosmetic ingredient capsules 300 of a given kit may vary by no more than 10%. As an example, when the average concentration of active ingredient 320 in the solid-shell cosmetic ingredient capsules of a kit is 2% by mass, the percent by mass of the active ingredient in each solid-shell cosmetic ingredient capsule 300 may vary between 1.9% and 2.1% (plus or minus 5% of the average 2% by mass) amongst the various solid-shell cosmetic ingredient capsules of the kit. However, in other examples, the capsules of a given kit having the active ingredient may have different concentrations of the active ingredient. Specifically, the dosage of the active ingredient within a given kit may increase, rather than, or in addition to, increasing between different kits.

Illustrative, non-exclusive examples of cosmetic blending devices, of solid-shell cosmetic ingredient capsules, and/or of methods according to the present disclosure are presented in the following enumerated paragraphs.

A. A cosmetic blending device for producing a cosmetic liquid from a solid-shell cosmetic ingredient capsule, the cosmetic blending device comprising:

a lid comprising a blending element configured to blend the solid-shell cosmetic ingredient capsule;

a base, wherein the lid and the base are configured to be selectively adjusted between an open position and a closed position, and wherein in the closed position, the base and the lid define an enclosed blending chamber;

a thermal element configured to change a temperature within the enclosed blending chamber; and a drive mechanism configured to actuate the blending element.

A1. The cosmetic blending device of paragraph A, wherein the cosmetic blending device is configured to produce the cosmetic liquid entirely from a shell and an enclosed inner volume of the solid-shell cosmetic ingredient capsule.

A2. The cosmetic blending device of any of paragraphs A-A1, wherein the lid defines an upper portion of the enclosed blending chamber, wherein the base defines a lower portion of the enclosed blending chamber, and wherein in the open position, the lower portion of the enclosed blending chamber is accessible to a user.

A3. The cosmetic blending device of any of paragraphs A-A2, wherein the cosmetic blending device further comprises an internal electrical energy source.

A4. The cosmetic blending device of paragraph A3, wherein the internal electrical energy source comprises a battery.

A5. The cosmetic blending device of paragraph A4, wherein the battery comprises a rechargeable battery.

A6. The cosmetic blending device of paragraph A5, wherein the internal electrical energy source is included in the base.

A7. The cosmetic blending device of paragraph A5, wherein the internal electrical energy source is included in the lid.

A8. The cosmetic blending device of any of paragraphs A-A2, wherein the cosmetic blending device is connected to an external electrical power source.

A9. The cosmetic blending device of any of paragraphs A-A8, wherein the drive mechanism is configured to drive the blending element in a plurality of directions, wherein the plurality of directions comprises two or more of a clockwise rotational direction, a counterclockwise rotational direction, and a translational direction.

A9.1. The cosmetic blending device of any of paragraphs A-A9, wherein the drive mechanism is configured to drive the blending element at a plurality of speeds, wherein the plurality of speeds includes two or more of, slower speeds during ramp-up periods, slower speeds during cool-down periods, higher speeds during a primary blending period, and oscillating speeds.

A9.2. The cosmetic blending device of any of paragraphs A-A9.1, wherein the drive mechanism comprises an electric motor.

A10. The cosmetic blending device of paragraph A9.2, wherein the drive mechanism comprises a mechanical linkage configured to transfer torque output from the electric motor to the blending element.

A11. The cosmetic blending device of paragraph A10, wherein the mechanical linkage comprises one or more of a helical gear, a worm gear, and a belt.

A12. The cosmetic blending device of paragraph A10, wherein the mechanical linkage comprises a planetary gear and a shaft.

A13. The cosmetic blending device of any of paragraphs A9.2-A12, wherein the drive mechanism is included in the lid.

A14. The cosmetic blending device of paragraph A13 when depending from any of paragraphs A10-A12, wherein the mechanical linkage extends from the base to the lid.

A15. The cosmetic blending device of any of paragraphs A9.2-A12, wherein the drive mechanism is included in the base.

A16. The cosmetic blending device of any of paragraphs A9.2-A15, wherein the drive mechanism is mounted vertically in the cosmetic blending device.

A17. The cosmetic blending device of any of paragraphs A9.2-A15, wherein the drive mechanism is mounted horizontally in the cosmetic blending device.

A18. The cosmetic blending device of any of paragraphs A-A17, further comprising a power transmitting structure that is configured to transmit electrical power to the drive mechanism.

A19. The cosmetic blending device of paragraph A18, wherein the power transmitting structure includes an interlock configured to transmit electrical power between the base and the lid.

A20. The cosmetic blending device of paragraph A19, wherein the interlock is configured to only permit power to be transmitted from the base to the lid when the base and the lid are in the closed position.

A21. The cosmetic blending device of any of paragraphs A19-A20, wherein the interlock comprises a first electrical contact that is included in the lid and a second electrical contact that is included in the base.

A22. The cosmetic blending device of paragraph A21, wherein the first electrical contact and the second electrical contact physically contact one another when the base and the lid are in the closed position, and do not physically contact one another when the base and the lid are in the open position.

A23. The cosmetic blending device of any of paragraphs A-A22, further comprising a control system configured to adjust operation of the cosmetic blending device.

A24. The cosmetic blending device of paragraph A23, wherein the control system comprises a controller, and wherein the controller is in electrical communication with one or more actuators of the cosmetic blending device, and is configured to adjust operation of the one or more actuators.

A25. The cosmetic blending device of paragraph A24, wherein the controller is in electrical communication with one or more sensors of the cosmetic blending device, and wherein the controller is configured to adjust operation of the one or more actuators based on feedback from the one or more sensors.

A26. The cosmetic blending device of paragraph A25, wherein the one or more sensors comprises one or more of a torque sensor and a rotational speed sensor, wherein the one or more actuators comprise the drive mechanism, and wherein the controller is programmed to adjust operation of the drive mechanism based on feedback from the sensor.

A27. The cosmetic blending device of paragraph A26, wherein the controller is programmed to adjust an electrical signal supplied to the drive mechanism based on a difference between a measured torque and/or rotational speed of the drive mechanism and a threshold torque and/or threshold rotational speed of the drive mechanism.

A28. The cosmetic blending device of paragraph A27, wherein the controller is programmed to increase an amount of electrical power supplied to the drive mechanism when one or more of the measured torque and the measured rotational speed of the blending element is less than the threshold torque and the threshold rotational speed, and to decrease the amount of electrical power supplied to the drive mechanism when one or more of the measured torque and the measured rotational speed of the blending element is greater than the threshold torque and the threshold rotational speed.

A29. The cosmetic blending device of any of paragraphs A27-A28, wherein the controller is programmed to set/determine the threshold torque and/or threshold rotational speed based on a characteristic of the solid-shell cosmetic ingredient capsule.

A30. The cosmetic blending device of any of paragraphs A27-A28, wherein the controller is programmed to set/determine the threshold torque and/or the threshold rotational speed based on user inputs.

A31. The cosmetic blending device of any of paragraphs A27-A28, wherein the threshold torque and/or the threshold rotational speed are predetermined and stored in non-transitory memory of the controller.

A32. The cosmetic blending device of any of paragraphs A27-A31, wherein the controller is configured to adjust the threshold torque and/or the threshold rotational speed during a blending cycle.

A32.1. The cosmetic blending device of paragraph A32, wherein the controller is configured to adjust the threshold torque and/or threshold rotational speed linearly, non-linearly, and/or in a step-wise manner during the blending cycle.

A32.2. The cosmetic blending device of any of paragraphs A24-A32.1, wherein the controller is configured to prevent opening of the blending chamber when a/the temperature of the cosmetic liquid is above a threshold temperature.

A32.3. The cosmetic blending device of any of paragraphs A24-A32.2, wherein the device produces the cosmetic liquid from at least one solid-shell cosmetic ingredient capsule by performing a/the blending cycle on the at least one solid-shell cosmetic ingredient capsule.

A32.4. The cosmetic blending device of paragraph A32.3, wherein the blending cycle comprises blending the at least one solid-shell cosmetic ingredient capsule, and further wherein the blending cycle comprises heating the at least one solid-shell cosmetic ingredient capsule or heating and cooling the at least one solid-shell cosmetic ingredient capsule.

A33. The cosmetic blending device of any of paragraphs A-A32.2, wherein at least a portion of a bottom of the lid defines a/the upper portion of the enclosed blending chamber.

A34. The cosmetic blending device of paragraph A33, wherein the bottom of the lid comprises a cavity, and wherein the blending element extends below at least a portion of the cavity.

A35. The cosmetic blending device of any of paragraphs A33-A34, wherein the lid further comprises a blending chamber seal that is configured to prevent fluid transfer between the enclosed blending chamber and an inside of the lid.

A36. The cosmetic blending device of any of paragraphs A-A35, wherein the blending element is configured to blend the entirety of the solid-shell cosmetic ingredient capsule.

A37. The cosmetic blending device of any of paragraphs A-A36, wherein the blending element is configured to both rotate and translate within the enclosed blending chamber.

A38. The cosmetic blending device of any of paragraphs A-A37, wherein the blending element comprises one or more cutting edges.

A38.1. The cosmetic blending device of any of paragraphs A38, wherein the one or more cutting edges comprises a forked cutting edge.

A38.2. The cosmetic blending device of any of paragraphs A38-A38.1, wherein the one or more cutting edges each are angled relative to the base at an angle, wherein the angle of the one or more cutting edges is selected to urge the solid-shell cosmetic ingredient capsule against the bottom of the blending chamber when the blending element is rotationally driven in a first direction and urge the capsule away from the bottom of the blending chamber when the blending element is rotationally driven in a second direction that opposes the first direction.

A39. The cosmetic blending device of any of paragraphs A38-A38.2, wherein the blending element comprises a substantially flat bottom.

A40. The cosmetic blending device of any of paragraphs A38-A39, wherein the one or more cutting edges include one or more curved cutting edges.

A40.1. The cosmetic blending device of paragraph A40, when depending from paragraph A39, wherein the one or more curved cutting edges extend upwards from the substantially flat bottom, towards a top of the lid.

A41. The cosmetic blending device of any of paragraphs A40-A40.1, wherein the one or more curved cutting edges comprise at least three curved cutting edges. A42. The cosmetic blending device of any of paragraphs A-A41, wherein at least a portion of a top of the base defines a/the lower portion of the enclosed blending chamber, wherein the top of the base comprises a bowl-shaped depression sized to contain the cosmetic liquid.

A43. The cosmetic blending device of paragraph A42, wherein the bowl-shaped depression is constructed from a heat conductive material.

A44. The cosmetic blending device of paragraph A43, wherein the bowl-shaped depression is constructed from aluminum.

A45. The cosmetic blending device of any of paragraphs A42-A44, wherein the bowl-shaped depression is configured to receive the solid-shell cosmetic ingredient capsule prior to adjusting the cosmetic blending device to the closed position.

A46. The cosmetic blending device of paragraph A45, wherein the bowl-shaped depression is at least 1 ml in volume and at most 25 ml in volume.

A47. The cosmetic blending device of any of paragraphs A45-A46, wherein a height of the bowl-shaped depression is at least 0.5 cm and at most 6 cm.

A48. The cosmetic blending device of any of paragraphs A45-A47, wherein the bowl-shaped depression comprises sidewalls and a bottom.

A49. The cosmetic blending device of paragraph A48, wherein the sidewalls are angled outward from the bottom of the bowl-shaped depression.

A50. The cosmetic blending device of any of paragraphs A48-A49, wherein a diameter of the bottom of the bowl-shaped depression is at least 0.4 cm and at most 6 cm.

A51. The cosmetic blending device of any of paragraphs A48-A50, wherein the bottom of the bowl-shaped depression is substantially flat and/or planar.

A52. The cosmetic blending device of any of paragraphs A48-A50, wherein the bottom of the bowl-shaped depression is concave.

A53. The cosmetic blending device of any of paragraphs A48-A52, wherein the bottom of the bowl-shaped depression comprises at least one indentation and/or concavity.

A54. The cosmetic blending device of any of paragraphs A48-A53, wherein the sidewalls and the bottom of the bowl-shaped depression have a thickness of at least 0.05 cm and at most 0.125 cm.

A55. The cosmetic blending device of any of paragraphs A48-A54, wherein the blending element is spaced above the bottom of the bowl-shaped depression when the lid and the base are in the closed position.

A56. The cosmetic blending device of paragraph A55, wherein the blending element is spaced above the bottom of the bowl-shaped depression by at least 0.5 mm and at most 10 mm.

A57. The cosmetic blending device of any of paragraphs A-A56, wherein the blending element is configured to at least puncture the solid-shell cosmetic ingredient capsule when the lid and the base are in the closed position.

A58. The cosmetic blending device of any of paragraphs A-A57, further comprising a cosmetic ingredient receptacle that is configured to receive the solid-shell cosmetic ingredient capsule when the solid-shell cosmetic ingredient capsule is placed in the enclosed blending chamber, and to hold the cosmetic liquid after the blending element blends the solid-shell cosmetic ingredient capsule to produce the cosmetic liquid.

A59. The cosmetic blending device of paragraph A58, wherein the base is configured to retain the cosmetic ingredient receptacle, and wherein the cosmetic ingredient receptacle is configured to be selectively removed from the base.

A60. The cosmetic blending device of paragraph A59, when depending from any of paragraphs A42-56, wherein the bowl-shaped depression is configured to receive the cosmetic ingredient receptacle, and wherein the cosmetic ingredient receptacle is configured to be selectively removed from the bowl-shaped depression.

A61. The cosmetic blending device of any of paragraphs A-A60, wherein the thermal element is configured to increase the temperature within the enclosed blending chamber.

A62. The cosmetic blending device of paragraph A61, wherein the thermal element is configured to heat the solid-shell cosmetic ingredient capsule in the enclosed blending chamber to at least 31.8° C. and at most 61.8° C.

A63. The cosmetic blending device of any of paragraphs A61-A62, wherein the thermal element is configured to increase the temperature of the blending element.

A64. The cosmetic blending device of any of paragraphs A61-A63, wherein the thermal element comprises a flex circuit.

A65. The cosmetic blending device of any of paragraphs A61-A63, wherein the thermal element comprises electrically resistive wire.

A66. The cosmetic blending device of any of paragraphs A-A65, wherein the thermal element is configured to decrease the temperature within the enclosed blending chamber.

A66.1. The cosmetic blending device of paragraph A66, wherein the thermal element is configured to cool the cosmetic liquid within the enclosed blending chamber to form a cooled cosmetic liquid.

A66.2. The cosmetic blending device of paragraph A66.1, wherein the thermal element is configured to produce the cooled cosmetic liquid with a temperature of at least 10° C. and at most 33° C.

A67. The cosmetic blending device of any of paragraphs A66-A66.2, wherein the thermal element comprises a cooling jacket.

A68. The cosmetic blending device of any of paragraphs A-A67, wherein the thermal element is included in one or more of the base and the lid.

A69. The cosmetic blending device of any of paragraphs A-A68, wherein the thermal element is positioned adjacent to a/the bowl-shaped depression.

A70. The cosmetic blending device of paragraph A69, when depending from any of paragraphs A42-A56, wherein the thermal element is coupled to an internal surface of one or more of a/the bottom and a/the sidewalls of the bowl-shaped depression.

A71. The cosmetic blending device of any of paragraphs A-A70, when depending from any of paragraphs A25-A32.2, wherein the one or more sensors comprise a temperature sensor, and wherein a/the controller is programmed to adjust operation of the thermal element based on feedback from the temperature sensor.

A72. The cosmetic blending device of paragraph A71, wherein the controller is programmed to adjust heat output of the thermal element based on a difference between a measured temperature and a threshold temperature.

A73. The cosmetic blending device of paragraph A72, wherein the controller is programmed to increase the amount of heat output by the thermal element when the measured temperature is less than the threshold temperature and to decrease the amount of heat output by the thermal element when the measured temperature is greater than the threshold temperature.

A74. The cosmetic blending device of any of paragraphs A72-A73, wherein the controller is programmed to actively cool the enclosed blending chamber by circulating a fluid having a lower temperature than the enclosed blending chamber through a/the cooling jacket.

A75. The cosmetic blending device of any of paragraphs A72-A74, wherein the controller is programmed to set/ determine the threshold temperature based on a characteristic of the solid-shell cosmetic ingredient capsule.

A76. The cosmetic blending device of any of paragraphs A72-A74, wherein the controller is programmed to set/ determine the threshold temperature based on user inputs.

A77. The cosmetic blending device of any of paragraphs A72-A74, wherein the threshold temperature is predetermined and stored in non-transitory memory of the controller.

A78. The cosmetic blending device of any of paragraphs A72-A77, wherein the controller is configured to adjust the threshold temperature during a blending cycle.

A79. The cosmetic blending device of any of paragraphs A-A78, wherein in the open position, the lid and the base decouple from one another.

A80. The cosmetic blending device of any of paragraphs A-A79, further comprising a coupling structure that is configured to selectively permit the lid and the base to adjust between the open and the closed positions.

A81. The cosmetic blending device of paragraph A80, wherein the coupling structure comprises a permanent coupling structure that is configured to permanently couple the lid and the base while permitting the lid and the base to be selectively adjusted between the open position and the closed position.

A82. The cosmetic blending device of paragraph A81, wherein the permanent coupling structure comprises a hinge.

A83. The cosmetic blending device of any of paragraphs A80-A82, wherein the coupling structure comprises a releasable locking structure that is configured to restrict relative movement between the lid and the base.

A84. The cosmetic blending device of paragraph A83, wherein the releasable locking structure comprises a threaded engagement between the lid and the base.

A85. The cosmetic blending device of paragraph A84, wherein the threaded engagement is configured to tighten in a first rotational direction, and wherein the blending element rotates in a second rotational direction, wherein the first rotational direction is opposite the second rotational direction.

A85.1. The cosmetic blending device of any of paragraphs A-A85, wherein the threaded engagement comprises threads disposed on the lid and the base that engage with one another to adjust the lid and the base between the open position and the closed position, and wherein the threads are configured to transmit electricity between the lid and the base in the closed position.

A85.2. The cosmetic blending device of paragraph A85.1, wherein one or more of the base and the lid comprise a resilient member that is compressed when the lid and the base are in the closed position, and wherein the resilient member is configured to urge the threads of the lid remain in electrical contact with the threads of the base during operative use of the cosmetic blending device to produce the cosmetic liquid and/or while the lid and the base are in the closed position.

A86. The cosmetic blending device of any of paragraphs A80-A85.2, wherein the coupling structure comprises a magnetic assembly configured to bias the lid and the base to the closed position.

A87. The cosmetic blending device of any of paragraphs A82-A86, when depending from any of paragraphs A18-A22, wherein the coupling structure comprises the power transmitting structure. A88. The cosmetic blending device of any of paragraphs A-A87, wherein the enclosed blending chamber is configured to receive the solid-shell cosmetic ingredient capsule.

A89. The cosmetic blending device of paragraph A88, wherein the enclosed blending chamber comprises a volume of at least 2 ml and at most 50 ml.

A90. The cosmetic blending device of any of paragraphs A-A89, further comprising an identification sensor configured to identify a characteristic of the solid-shell cosmetic ingredient capsule.

A91. The cosmetic blending device of paragraph A90, wherein the identification sensor comprises an RFID scanner.

A92. The cosmetic blending device of paragraph 90, wherein the identification sensor comprises a barcode scanner.

A93. The cosmetic blending device of any of paragraphs A-A92, wherein the blending element is a removable blending element.

A94. The cosmetic blending device of any of paragraphs A-A93, wherein the cosmetic blending device comprises a plurality of the removable blending elements, wherein the cosmetic blending device is configured to selectively and interchangeably utilize a selected one removable blending element of the plurality of removable blending elements to perform a/the blending cycle.

B. A solid-shell cosmetic ingredient capsule configured to be heated and blended to produce a cosmetic liquid, the solid-shell cosmetic ingredient capsule comprising: a shell defining an enclosed inner volume, the shell comprising a combination of oil and wax; and a cosmetic material at least partially filling the enclosed inner volume.

B1. The solid-shell cosmetic ingredient capsule of paragraph B, wherein when melted and blended, the solid-shell cosmetic ingredient capsule forms the entirety of the cosmetic liquid.

B2. The solid-shell cosmetic ingredient capsule of any of paragraphs B-B1, wherein the solid-shell cosmetic ingredient capsule is packageless, such that when melted and blended, the entirety of the solid-shell cosmetic ingredient capsule forms the cosmetic liquid.

B3. The solid-shell cosmetic ingredient capsule of any of paragraphs B-B2, wherein the cosmetic liquid includes the shell and at least one of a personal care ingredient and a microcapsule from the enclosed inner volume of the solid-shell cosmetic ingredient capsule.

B4. The solid-shell cosmetic ingredient capsule of any of paragraphs B-B3, wherein the shell has a melting temperature of at least 27° C. and/or at most 49° C.

B5. The solid-shell cosmetic ingredient capsule of any of paragraphs B-B4, wherein the inner volume is at least 0.5 ml and at most 2 ml.

B6. The solid-shell cosmetic ingredient capsule of any of paragraphs B-B5, wherein the shell has a thickness of at least 0.5 mm and at most 5 mm.

B7. The solid-shell cosmetic ingredient capsule of any of paragraphs B-B6, wherein the shell is hydrophobic.

B8. The solid-shell cosmetic ingredient capsule of paragraph B7, wherein the shell is a fluid barrier that is configured to prevent fluid flow between the inner volume and an outside of the shell.

B9. The solid-shell cosmetic ingredient capsule of any of paragraphs B-B8, wherein an exterior surface of the shell directly interfaces with ambient air.

B10. The solid-shell cosmetic ingredient capsule of any of paragraphs B-B9, wherein the shell is configured to withstand a threshold compressive load applied to the shell when the shell is below its melting temperature.

B10.1. The solid-shell cosmetic ingredient capsule of paragraph B10, wherein the threshold compressive load is at least 6890 N/m$^2$.

B10.1.1. The solid-shell cosmetic ingredient capsule of any of paragraphs B10-10.1, wherein the threshold compressive load is at least 54,000 N/m$^2$ and at most 110,000 N/m$^2$.

B10.2. The solid-shell cosmetic ingredient capsule of any of paragraphs B-B10.1.1, wherein the shell configured to be solid and sealably enclose the inner volume when the shell is below its melting temperature.

B10.2.1. The solid-shell cosmetic ingredient capsule of any of paragraphs B-B10.2, wherein the shell is configured to be solid and sealably enclose the enclosed inner volume under a threshold crush force.

B10.2.2. The solid shell cosmetic ingredient capsule of paragraph B10.2.1, wherein the threshold crush force is 10 Newton (N).

B10.3. The solid-shell cosmetic ingredient capsule of any of paragraphs B-B10.2.2, wherein the shell comprises a threshold minimum compressive strength.

B10.3.1. The solid-shell cosmetic ingredient capsule of paragraph B10.3, wherein the threshold minimum compressive strength is 6890 N/m$^2$.

B10.3.2. The solid-shell cosmetic ingredient capsule of any of paragraphs B10.3-B10.3.1, wherein the threshold minimum compressive strength is at least 54,000 N/m$^2$ and at most 110,000 N/m$^2$.

B10.4. The solid-shell cosmetic ingredient capsule of any of paragraphs B-B10.3.2, wherein the solid-shell cosmetic ingredient capsule comprises a threshold minimum crush resistance.

B10.4.1. The solid-shell cosmetic ingredient capsule of paragraph B10.4, wherein the threshold minimum crush resistance is 10 Newton (N).

B10.4.2. The solid-shell cosmetic ingredient capsule of paragraph B10.4, wherein the threshold minimum crush resistance is at least 9 Newton (N), and at most 12 N.

B11. The solid-shell cosmetic ingredient capsule of any of paragraphs B-B10.4.2, wherein the shell comprises at least 35% and at most 90% by weight of fat and oil. B12. The solid-shell cosmetic ingredient capsule of any of paragraphs B-B11, wherein the shell comprises at least 10% and at most 50% by weight of chemically inert materials.

B13. The solid-shell cosmetic ingredient capsule of any of paragraphs B-B12, wherein the shell comprises one or more crystal promoters.

B13.1 The solid-shell cosmetic ingredient capsule of paragraph B13 wherein the shell comprises at least 0.25% % and at most 25% by weight of the one or more crystal promoters.

B13.2. The solid-shell cosmetic ingredient capsule of any of paragraphs B13-B13.1, wherein at least one of the one or more crystal promoters increase the melting point of the shell relative to an otherwise equivalent shell that does not include the one or more crystal promoters, and the one or more crystal promoters increase the crush resistance of the shell relative to an otherwise equivalent shell that does not include the one or more crystal promoters.

B14. The solid-shell cosmetic ingredient capsule of any of paragraphs B-B13.2, wherein the cosmetic material includes a personal care ingredient.

B15. The solid-shell cosmetic ingredient capsule of paragraph B14, wherein a weight of the personal care ingredient is at least 25% and at most 110% of the weight of the shell.

B16. The solid-shell cosmetic ingredient capsule of any of paragraphs B14-B15, wherein the personal care ingredient comprises one or more of a cream, oil, gel, serum, mousse, pigment, emollient, sunscreen, shampoo, preservative, conditioner, facemask, lipstick, blemish balm, emulsifier, chemically inert substance, and thickener.

B17. The solid-shell cosmetic ingredient capsule of any of paragraphs B-B16, wherein the solid-shell cosmetic ingredient capsule comprises an active ingredient.

B17.1 The solid-shell cosmetic ingredient capsule of paragraph B17, wherein cosmetic material comprises the active ingredient.

B17.2 The solid-shell cosmetic ingredient capsule of any of paragraphs B17-B17.1, wherein the shell comprises the active ingredient.

B17.3 The solid-shell cosmetic ingredient capsule of any of paragraphs B17-B17.2 wherein the shell and the cosmetic material comprise the active ingredient.

B17.3.1 The solid shell cosmetic ingredient capsule of paragraph B17.3, wherein the shell comprises a first amount of the active ingredient and the cosmetic material comprises a second amount of the active ingredient;
wherein the active ingredient is present in the shell at a first concentration that includes the first amount of the active ingredient in a total volume of the shell, wherein the active ingredient is present in the cosmetic material at a second concentration that includes the second amount of the active ingredient in a total volume of the cosmetic material, and wherein the second concentration is less than a saturation concentration of the active ingredient in the cosmetic material; and
wherein a total amount of the active ingredient in the solid-shell cosmetic ingredient capsule includes the first amount of the active ingredient and the second amount of the active ingredient, and wherein the total amount of the active ingredient the solid-shell cosmetic ingredient capsule exceeds a solubility limit of the active ingredient in the total volume of the cosmetic material.

B17.3.1.1. The solid-shell cosmetic ingredient capsule of paragraph B17.3.1, wherein the second concentration of the active ingredient is greater than the saturation concentration of the active ingredient in the cosmetic material, and wherein when the cosmetic material and the shell are heated and mechanically blended to form the cosmetic liquid, the cosmetic liquid comprises an active ingredient concentration that is greater than the saturation concentration of the active ingredient in the cosmetic material.

B17.3.1.2. The solid-shell cosmetic ingredient capsule of paragraph B17.3.1.1, wherein the active ingredient has a higher solubility in the shell than in the cosmetic material.

B18. The solid-shell cosmetic ingredient capsule of any of paragraphs B17-B17.3.1.2, wherein the solid-shell cosmetic ingredient capsule comprises at least 0.025% and at most 20% by weight of the active ingredient.

B19. The solid-shell cosmetic ingredient capsule of any of paragraphs B17-B18, wherein the active ingredient comprises at least 0.05% and at most 20% by weight of the shell.

B20. The solid-shell cosmetic ingredient capsule of any of paragraphs B17-B18, wherein the enclosed inner volume includes at least 0.05% and at most 50% by weight of the active ingredient.

B21. The solid-shell cosmetic ingredient capsule of any of paragraphs B17-B20, wherein the active ingredient comprises one or more of alpha-hydroxy acids, polyhydroxy acids, beta-hydroxy acids, botanical derivatives (e.g. kojic acid), skin lightening agents, vitamins (e.g. retinoids), essential oils, prescription ingredients, proteins, peptides, anti-aging agents, antioxidants, anti-wrinkle agents, hair repair agents, humectants, rejuvenating and soothing agents, skin darkening agents, liposomes, and/or sunscreen agents.

B21.1 The solid-shell cosmetic ingredient capsule of paragraph B21, wherein the humectants include at least one of propylene glycol, glycerin, water soluble sugars, butylene glycol, propanediol, polyhydroxy acids, alpha-hydroxy acids, beta-hydroxy acids, hyaluronic acid, urea, lactates, and/or panthenol.

B22. The solid-shell cosmetic ingredient capsule of any of paragraphs B17-B21.1, further comprising one or more microcapsules, wherein the one or more microcapsules comprise a protective coating and the active ingredient.

B23. The solid-shell cosmetic ingredient capsule of paragraph B22, wherein the protective coating is configured to prevent dissolution of the one or more microcapsules within the solid-shell cosmetic ingredient capsule.

B24. The solid-shell cosmetic ingredient capsule of paragraph B23, wherein the protective coating comprises one or more of gelatin, cellulose, resins, fats, lipids, phospholipids, triglycerides, and wax.

B25. The solid-shell cosmetic ingredient capsule of any of paragraphs B22-B24, wherein the protective coating is configured to dissolve when the solid-shell cosmetic ingredient capsule is heated and blended to produce the cosmetic liquid.

B25.1 The solid-shell cosmetic ingredient capsule of any of paragraphs B22-B25, wherein the protective coating is configured to dissolve into the shell when the solid-shell cosmetic ingredient capsule is heated and blended to produce the cosmetic liquid.

B26. The solid-shell cosmetic ingredient capsule of any of paragraphs B22-B25.1, wherein at least one of the one or more microcapsules is embedded in the shell.

B27. The solid-shell cosmetic ingredient capsule of any of paragraphs B22-B26, wherein at least one of the one or more microcapsules is included in the inner volume.

B28. The solid-shell cosmetic ingredient capsule of any of paragraphs B22-B27, wherein the solid-shell cosmetic ingredient capsule further comprises a central compartment that includes the active ingredient.

B29. The solid-shell cosmetic ingredient capsule of any of paragraphs B-B28, further comprising a unique identifier configured to identify a characteristic of the solid-shell cosmetic ingredient capsule.

B30. The solid-shell cosmetic ingredient capsule of paragraph B29, wherein the characteristic of the solid-shell cosmetic ingredient capsule includes one or more of a type, a name, a symbol, a pattern, and a serial number of the solid-shell cosmetic ingredient capsule.

B31. The solid-shell cosmetic ingredient capsule of any of paragraphs B29-B30, wherein the unique identifier comprises an RFID tag.

B32. The solid-shell cosmetic ingredient capsule of any of paragraphs B29-B30, wherein the unique identifier comprises a barcode.

B32.1 The solid-shell cosmetic ingredient capsule of any of paragraphs B29-B30, wherein the unique identifier comprises a QR code.

B33. The solid-shell cosmetic ingredient capsule of any of paragraphs B-B32.1, wherein, wherein the shell comprises a water activity ($a_w$) of at least 0.1 $a_w$ and at most 0.6 $a_w$.

B33.1 The solid-shell cosmetic ingredient capsule of paragraph B33, wherein the shell comprises water, and wherein the shell comprises at least one humectant to reduce the water activity ($a_w$) of the shell to be at most 0.6 $a_w$.

B33.2 The solid-shell cosmetic ingredient capsule of any of paragraphs B-B32.1, wherein the cosmetic material comprises a water activity ($a_w$) of at least 0.5 $a_w$ and at most 0.7 $a_w$.

B33.2.1 The solid-shell cosmetic ingredient capsule of paragraph B33.2, wherein the cosmetic material comprises water, and wherein the cosmetic material comprises at least one humectant to reduce the water activity ($a_w$) of the shell to be at most 0.7 $a_w$.

B34. The solid-shell cosmetic ingredient capsule of any of paragraphs B-B33.2.1, wherein the shell is formed in one or more layers, and wherein the one or more layers possess the same or different properties, components, and/or thicknesses.

B35. The solid-shell cosmetic ingredient capsule of any of paragraphs B-B34, wherein the shell comprises at least 40% and at most 90% by weight of the cosmetic ingredient capsule.

B36. The solid-shell cosmetic ingredient capsule of any of paragraphs B-B34, wherein the cosmetic material comprises at least 10% and at most 60% by weight of the cosmetic ingredient capsule.

B37. The solid-shell cosmetic ingredient capsule of any of paragraphs B-B36, wherein the cosmetic liquid is formed from the solid-shell cosmetic ingredient capsule only when the solid-shell cosmetic ingredient capsule blended with a threshold rotational speed.

B37.1 The solid-shell cosmetic ingredient capsule of paragraph B37, wherein the threshold rotational speed is at least 400 revolutions per minute.

B37. 2. The solid-shell cosmetic ingredient capsule of any of paragraphs B-B37.1, wherein the cosmetic liquid is formed from the solid-shell cosmetic ingredient capsule only when the solid-shell cosmetic ingredient capsule is heated to at least 38° C.

B38. The solid-shell cosmetic ingredient capsule of any of paragraphs B1-B37.2, wherein the shell comprises a stable crystal structure resulting from at least one of:
 heat treatment of one or more components that form the shell;
 selective formation of one or more desired crystal phases or crystal types within the shell;
 selective exclusion of one or more undesired crystal phases or crystal types within the shell; and
 selective growth of one or more desired crystal phases or crystal types within the shell.

B39. The solid-shell cosmetic ingredient capsule of any of paragraphs B-B38, wherein the shell is a tempered shell.

B39,1. The solid-shell cosmetic ingredient capsule of paragraph B39, and wherein at least one of:
 the tempered shell comprises a higher melting point than an otherwise equivalent shell that is not tempered; and
 the tempered shell comprises a higher compressive strength or a higher crush resistance relative to the otherwise equivalent shell that is not tempered.

B40. The solid-shell cosmetic ingredient capsule of any of paragraphs B-B38, wherein the shell is a conditioned shell.

B40.1. The solid-shell cosmetic ingredient capsule of paragraph B40, wherein at least one of:
 the conditioned shell comprises a higher compressive strength relative to an otherwise equivalent shell that is not conditioned; and
 the conditioned shell comprises a higher compressive strength or a higher crush resistance relative to the otherwise equivalent shell that is not conditioned.

B41. The solid-shell cosmetic ingredient capsule of any of paragraphs B-B40, wherein the shell and the cosmetic material are formulated such that the cosmetic liquid forms a stable liquid mixture for at least a threshold duration of time subsequent to the heating and blending, B41.1 The solid-shell cosmetic ingredient capsule of paragraph B41, wherein the threshold duration of time is at least one of at least 5 minutes, at least 10 minutes, at least 30 minutes, at least 1 hour, at least 3 hours, at most 1 hour, at most 5 hours, at most 10 hours, and at most 1 day.

B42. A system for storing and providing a cosmetic liquid, the system comprising:
 the solid-shell cosmetic ingredient capsule of any of paragraphs B-B41.1 or a plurality solid shell cosmetic ingredient capsules each being the solid-shell cosmetic capsule recited in any of paragraphs B-B41.1; and
 a blending device configured to heat and blend the solid-shell cosmetic ingredient capsule to produce the cosmetic liquid.

B43 The solid-shell cosmetic ingredient capsule of any of paragraphs B-B42, formed by performing the methods of any of paragraphs F-F6.

C. A cosmetic blending system, comprising:
 the cosmetic blending device of any of paragraphs A-A94; and
 the solid-shell cosmetic ingredient capsule of any of paragraphs B-B43, wherein the enclosed blending chamber is configured to receive the solid-shell cosmetic ingredient capsule.

D. A method for forming a cosmetic liquid from a solid-shell cosmetic ingredient capsule, the method comprising:
 heating the solid-shell cosmetic ingredient capsule beyond its melting point with one or more thermal elements; and
 blending the solid-shell cosmetic ingredient capsule with an overhead blending element.

D1. The method of paragraph D, further comprising placing the solid-shell cosmetic ingredient capsule into a blending chamber, and closing the blending chamber prior to the heating and the blending.

D2. The method of paragraph D1, wherein the placing comprises placing the solid-shell cosmetic ingredient capsule into the blending chamber without any packaging, such that the entirety of the solid-shell cosmetic ingredient capsule forms the cosmetic liquid when heated and blended.

D3. The method of any of paragraphs D1-D2, wherein the placing comprises placing only a single solid-shell cosmetic ingredient capsule into the blending chamber.

D4. The method of paragraph D3, wherein the single solid-shell cosmetic ingredient capsule forms the entirety of the cosmetic liquid.

D5. The method of any of paragraphs D1-D2, wherein the placing comprises placing the solid-shell cosmetic ingredient capsule and at least one additional solid-shell cosmetic ingredient capsule into the blending chamber.

D6. The method of paragraph D5, wherein the solid-shell cosmetic ingredient capsule and the at least one additional solid-shell cosmetic ingredient capsule form the entirety of the cosmetic liquid.

D7. The method of any of paragraphs D5-D6, wherein the at least one additional solid-shell cosmetic ingredient capsule comprises at most two additional solid-shell cosmetic ingredient capsules.

D8. The method of any of paragraphs D1-D2 and D5-D7, wherein the placing comprises placing the solid-shell cosmetic ingredient capsule and at least one cosmetic ingredient into the blending chamber.

D9. The method of any of paragraphs D5-D8, wherein a/the at least one cosmetic ingredient comprises an oil.

D10. The method of any of paragraphs D1-D9, wherein the closing comprises rotating one or more of a base and a lid of a cosmetic blending device in a first rotational direction.

D11. The method of any of paragraphs D1-D10, wherein the closing comprises locking the base and the lid.

D12. The method of paragraph D11, when depending from paragraph D10, wherein the locking comprises rotating one or more of the base and the lid in the first rotational direction until a spring-loaded pin of the base engages a mating hole in the lid.

D13. The method of any of paragraphs D-D12, wherein the heating and the blending comprise heating and blending the entire solid-shell cosmetic ingredient capsule.

D14. The method of any of paragraphs D-D13, further comprising monitoring one or more blending parameters and adjusting one or more of the heating and the blending based on the monitored blending parameters.

D15. The method of paragraph D14, wherein the monitoring comprises monitoring a temperature of a/the blending chamber and adjusting the one or more thermal elements to maintain the temperature of the blending chamber within a threshold temperature range.

D16. The method of paragraph D15, wherein the threshold temperature range is at least 32.2° C. and at most 60° C.

D17. The method of any of paragraphs D14-D16, wherein the monitoring comprises monitoring a torque of the overhead blending element and adjusting the overhead blending element to maintain the torque within a threshold torque range.

D18. The method of paragraph D17, wherein the method further comprises stopping the blending when the monitored torque decreases below a lower torque threshold.

D19. The method of any of paragraphs D14-D18, wherein the monitoring comprises monitoring a rotational speed of the overhead blending element and adjusting the blending element to maintain the rotational speed within a threshold speed range.

D20. The method of paragraph D19, wherein the threshold speed range is at least 400 revolutions per minute and at most 1,300 revolutions per minute.

D21. The method of any of paragraphs D-D20, wherein the heating comprises heating the solid-shell cosmetic ingredient capsule to at least 90° F. (32.2° C.) and at most 140° F. (60° C.).

D22. The method of any of paragraphs D-D21, wherein the blending comprises rotating the blending element to at least 400 and at most 1,300 revolutions per minute.

D23. The method of paragraph D22 when depending from any of paragraphs D10 and D12, wherein the blending comprises rotating the blending element in a second rotational direction that is opposite the first rotational direction.

D24. The method of any of paragraphs D-D23, wherein the method further comprises, while heating the solid-shell cosmetic ingredient capsule, waiting to commence the blending for a delay duration, and then blending for a blend duration.

D25. The method of paragraph D24, wherein the delay duration is at least 10 seconds and at most 30 seconds.

D26. The method of any of paragraphs D24-D25, wherein the delay duration terminates when the solid-shell cosmetic ingredient capsule is liquefied.

D27. The method of any of paragraphs D24-D26, wherein the blend duration is at least 10 seconds and at most 1 minute.

D28. The method of any of paragraphs D-D27, further comprising determining a characteristic of the solid-shell cosmetic ingredient capsule based on a unique identifier included in the solid-shell cosmetic ingredient capsule and setting threshold blending parameters based on the determined identity.

D29. The method of paragraph D28, wherein the characteristic comprises one or more of an identity, a type, a serial number, and a name of the solid-shell cosmetic ingredient capsule.

D30. The method of any of paragraphs D-D29, further comprising crushing the solid-shell cosmetic ingredient capsule with the overhead blending element prior to blending the solid-shell cosmetic ingredient capsule.

D31. The method of paragraph D30, wherein the crushing comprises deforming a rigid outer shell of the solid-shell cosmetic ingredient capsule.

D32. The method of any of paragraphs D-D31, further comprising, after the heating and blending, cooling the cosmetic liquid to below 120° F. (48.9° C.) before presenting the cosmetic liquid to a user.

D33. The method of any of paragraphs D-D32, wherein the blending includes rotating and axially translating the blending element.

D34. The method of any of paragraphs D-D33, further comprising alerting a user when the cosmetic liquid is ready for extraction.

D35. The method of paragraph D34, wherein the alerting comprises generating an audible notification.

D36. The method of any of paragraphs D34-D35, wherein the alerting comprises generating a visual notification.

D37. The method of paragraph D36, wherein the generating the visual notification comprises illuminating an LED.

D38. The method of any of paragraphs D-D37, further comprising opening a/the blending chamber and extracting the cosmetic liquid.

D39. The method of any of paragraphs D-D38, wherein the solid-shell cosmetic ingredient capsule is the solid-shell cosmetic ingredient capsule of any of paragraphs B-B43.

D40. The method of any of paragraphs D-D39, wherein the heating and blending are performed in the cosmetic blending device of any of paragraphs A-A94.

E. A kit configured to provide a regimented dosage schedule for an active ingredient, the kit comprising:
   a solid-shell cosmetic ingredient capsule comprising the active ingredient; and
   packaging configured to retain the solid-shell cosmetic ingredient capsule.

E1. The kit of paragraph E, wherein the solid-shell cosmetic ingredient capsule is the solid-shell cosmetic ingredient capsule of any of paragraphs B-B43, and wherein the active ingredient is the active ingredient of solid-shell cosmetic ingredient capsule of any of paragraphs B-B43.

E2. The kit of paragraph E1, further comprising a plurality of the solid-shell cosmetic ingredient capsules.

E3. The kit of paragraph E2, wherein at least two or more of the plurality of the solid-shell cosmetic ingredient capsules include different concentrations of the active ingredient.

E4. The kit of any of paragraphs E-E3, further comprising an active-free solid-shell cosmetic ingredient capsules that does not include the active ingredient.

E5. A regimented dosage scheduler comprising two or more of the kits of any of paragraphs E-E4.

E6 The regimented dosage schedule of paragraph E5, wherein the solid-shell cosmetic ingredient capsules of the two or more kits include different concentrations of the active ingredient.

F. A method of forming a solid-shell cosmetic ingredient capsule, the method comprising:
forming a first portion of a shell of the solid-shell cosmetic ingredient capsule, the forming comprising:
preparing a liquid shell material by preparing a mixture of shell components and heating and blending the mixture of shell components;
dispensing the liquid shell material into a mold; and
solidifying at least a portion of the liquid shell material within the mold to form the first portion of the shell, wherein the first portion of the shell at least partially defines an interior of the shell;
adding a cosmetic material to the interior of the shell; and
forming at least a second portion of the shell to enclose the cosmetic material within the interior of the shell.

F1. The method of paragraph F, wherein the forming the first portion of the shell further comprises heat treating the liquid shell material.

F1.1 The method of paragraph F 1, wherein the heat treating the liquid shell material comprises facilitating the formation of a stable crystal structure from the liquid shell material.

F1.2. The method of any of paragraphs F1-F1.1, wherein the heat treating the liquid shell material comprises tempering the liquid shell material.

F1.2.1 The method of paragraph F1.2, wherein the tempering the liquid shell material comprises repeatedly alternating between heating and cooling the liquid shell material, optionally while stirring the liquid shell material.

F1.2.2 The method of paragraph F1.2.1, wherein the repeatedly alternating between heating and cooling the liquid shell material comprises heating the liquid shell material above the melting point of one or more undesired crystal phases or crystal types present in the liquid shell material to melt the one or more undesired crystal phases or crystal types and subsequently cooling the liquid shell material to form one or more desired crystal phases or crystal types from the melted one or more undesired crystal phases or crystal types.

F1.3. The method of any of paragraphs F1-F1.2.2, wherein the heat treating the liquid shell material comprises conditioning the liquid shell material.

F1.3.1. The method of paragraph F1.3, wherein the conditioning the liquid shell material comprises maintaining the liquid shell material at a conditioning temperature, optionally while stirring the liquid shell material.

F1.3.1. The method of paragraph 1.3, wherein the conditioning temperature is at least 0.5° C. below and at most 10° C. below the melting point or the lower end of the melting point range of the liquid shell material.

F.1.4. The method of any of paragraphs F1-F1.3.1, wherein the heat treating the liquid shell material comprises increasing the melting point of the shell, increasing the compressive strength of the shell, increasing the crush resistance of the shell, decreasing the solubility of the shell in water, decreasing the solubility of the shell in the cosmetic material, decreasing the dissolution rate (the kinetic parameter) of the shell in water, and/or decreasing the dissolution rate of the shell in the cosmetic material.

F2. The method of any of paragraphs F-F1.4, wherein the forming the first portion of the shell further comprises adding one or more crystal promoters to the liquid shell material.

F3. The method of any of paragraphs F-F2, wherein the adding the cosmetic material to the interior of the shell comprises adding the cosmetic material in a liquid state, a semi-liquid state, and/or a solid state.

F4. The method of any of paragraphs F-F3, wherein the forming at least the second portion of the shell comprises forming a plurality of additional shell components and joining the plurality of additional shell components with the first portion of the shell to enclose the cosmetic material within the interior of the shell.

F4.1. The method of any of paragraphs F-F4, wherein the forming at least the second portion of the shell comprises repeating one or more of the same steps that are performed to form the first portion of the shell.

F5. The method of any of paragraphs F-F4.1, wherein the cosmetic material comprises a first amount of the active ingredient, and wherein the preparing the liquid shell material comprises adding a second amount of an active ingredient to the mixture of shell components.

F6. The method of any of paragraphs F-F5, wherein the solid-shell cosmetic ingredient capsule is the solid-shell cosmetic ingredient capsule of any of paragraphs B-B43.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities optionally may be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities optionally may be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" may mean A alone, B alone, C alone, A and B together, A and C together, B and C together, A, B, and C together, and optionally any of the above in combination with at least one other entity.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function additionally or alternatively may be described as being configured to perform that function, and vice versa.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

INDUSTRIAL APPLICABILITY

The cosmetic blending devices, solid-shell cosmetic ingredient capsules, and methods disclosed herein are applicable to the cosmetics industry.

The invention claimed is:

1. A solid-shell cosmetic ingredient capsule, comprising:
a shell defining an enclosed inner volume,
a cosmetic material at least partially filling the enclosed inner volume; and
wherein below 27° C., the shell is configured to be solid and sealably enclose the enclosed inner volume under a crush force of 10 Newton (N), wherein the solid-shell cosmetic ingredient capsule is configured to be heated and blended to produce a cosmetic liquid, wherein the cosmetic liquid is an at least substantially homogenous mixture of the shell and the cosmetic material, wherein the shell comprises a water activity ($a_w$) of at least 0.1 $a_w$ and at most 0.6 $a_w$, and wherein the cosmetic material comprises a water activity ($a_w$) of at least 0.5 $a_w$ and at most 0.7 $a_w$.

2. The solid-shell cosmetic ingredient capsule of claim 1, wherein the cosmetic liquid is formed from the solid-shell cosmetic ingredient capsule when the solid-shell cosmetic ingredient capsule is heated to at least 38° C. and blended with a rotational speed of at least 400 revolutions per minute.

3. The solid-shell cosmetic ingredient capsule of claim 1, wherein the shell further comprises one or more crystal promoters, wherein the one or more crystal promoters comprise at least 0.25% and at most 25% by weight of the shell; and wherein the one or more crystal promoters:
stabilize crystal domains within the shell; and/or
increase the size of stable crystal domains within the shell.

4. The solid-shell cosmetic ingredient capsule of claim 3, wherein at least one of the one or more crystal promoters increase a melting point of the shell relative to an otherwise equivalent shell that does not include the one or more crystal promoters, and the one or more crystal promoters increase a crush resistance of the shell relative to an otherwise equivalent shell that does not include the one or more crystal promoters.

5. The solid-shell cosmetic ingredient capsule of claim 1, wherein the shell comprises a stable crystal structure resulting from at least one of:
heat treatment of one or more components that form the shell;
selective formation of one or more desired crystal phases or crystal types within the shell;
selective exclusion of one or more undesired crystal phases or crystal types within the shell; and
selective growth of one or more desired crystal phases or crystal types within the shell.

6. The solid-shell cosmetic ingredient capsule of claim 1, wherein the shell is a tempered shell.

7. The solid-shell cosmetic ingredient capsule of claim 6, and wherein at least one of:
the tempered shell comprises a higher melting point than an otherwise equivalent shell that is not tempered; and
the tempered shell comprises a higher compressive strength or a higher crush resistance relative to the otherwise equivalent shell that is not tempered.

8. The solid-shell cosmetic ingredient capsule of claim 1, wherein the shell is a conditioned shell.

9. The solid-shell cosmetic ingredient capsule of claim 8, wherein the conditioned shell comprises a higher compressive strength relative to an otherwise equivalent shell that is not conditioned.

10. The solid-shell cosmetic ingredient capsule of claim 1, wherein the shell comprises at least one active ingredient.

11. The solid-shell cosmetic ingredient capsule of claim 1, wherein the shell comprises fats, chemically inert materials, and at least one active ingredient, and wherein the fats comprise at least 35% and at most 90% by weight of the shell, the chemically inert materials comprise at least 2% and at most 60% by weight of the shell, and the at least one active ingredient comprises at least 0.05% and at most 10% by weight of the shell.

12. The solid-shell cosmetic ingredient capsule of claim 1, wherein the shell comprises water, and wherein the shell comprises at least one humectant to reduce the water activity ($a_w$) of the shell to be at most 0.6 $a_w$.

13. The solid shell cosmetic ingredient capsule of claim 1, wherein the cosmetic material comprises water, and wherein the cosmetic material comprises at least one humectant to reduce the water activity ($a_w$) of the cosmetic material to be at most 0.7 $a_w$.

14. The solid-shell cosmetic ingredient capsule of claim 1, wherein the shell and the cosmetic material are formulated such that the cosmetic liquid forms a stable liquid mixture for at least a threshold duration of time subsequent to being heated and blended, wherein the threshold duration of time is 30 minutes.

15. A system for storing and providing a cosmetic liquid, the system comprising:
the solid-shell cosmetic ingredient capsule of claim 1; and
a blending device configured to heat and blend the solid-shell cosmetic ingredient capsule to produce the cosmetic liquid.

16. A kit configured to provide a regimented dosage schedule for an active ingredient of the solid-shell cosmetic ingredient capsule of claim 1, the kit comprising:
the solid-shell cosmetic ingredient capsule of claim 1; and
packaging configured to retain the solid-shell cosmetic ingredient capsule.

17. The kit of claim 16, further comprising a plurality of the solid-shell cosmetic ingredient capsules, wherein at least two or more of the plurality of the solid-shell cosmetic ingredient capsules comprise different concentrations of the active ingredient.

18. The kit of claim 16, further comprising at least one active-free solid-shell cosmetic ingredient capsule that does not comprise the active ingredient.

19. A regimented dosage schedule comprising two or more of the kits of claim 18, wherein the solid-shell cosmetic ingredient capsules of the two or more kits comprise different concentrations of the active ingredient.

20. A solid-shell cosmetic ingredient capsule, comprising:
a shell defining an enclosed inner volume, wherein the shell comprises fats, chemically inert materials, and at least one active ingredient, and wherein the fats comprise at least 35% and at most 90% by weight of the shell, the chemically inert materials comprise at least 2% and at most 60% by weight of the shell, and the at least one active ingredient comprises at least 0.05% and at most 10% by weight of the shell;
a cosmetic material at least partially filling the enclosed inner volume; and
wherein below 27° C., the shell is configured to be solid and sealably enclose the enclosed inner volume under a crush force of 10 Newton (N), wherein the solid-shell cosmetic ingredient capsule is configured to be heated and blended to produce a cosmetic liquid, wherein the cosmetic liquid is an at least substantially homogenous mixture of the shell and the cosmetic material.

21. The solid-shell cosmetic ingredient capsule of claim 20, wherein the shell is a tempered shell, and further wherein at least one of:
the tempered shell comprises a higher melting point than an otherwise equivalent shell that is not tempered; and
the tempered shell comprises a higher compressive strength or a higher crush resistance relative to the otherwise equivalent shell that is not tempered.

22. A system for storing and providing a cosmetic liquid, the system comprising:
the solid-shell cosmetic ingredient capsule of claim 20; and
a blending device configured to heat and blend the solid-shell cosmetic ingredient capsule to produce the cosmetic liquid.

23. A kit configured to provide a regimented dosage schedule for an active ingredient of the solid-shell cosmetic ingredient capsule of claim 20, the kit comprising:
the solid-shell cosmetic ingredient capsule of claim 20; and
packaging configured to retain the solid-shell cosmetic ingredient capsule.

* * * * *